US007626030B2

(12) United States Patent
Kim et al.

(10) Patent No.: US 7,626,030 B2
(45) Date of Patent: Dec. 1, 2009

(54) COMPOUNDS AND METHODS OF USE

(75) Inventors: Tae-Seong Kim, Thousand Oaks, CA (US); Jean-Christophe Harmange, Andover, MA (US); David Bauer, Sudbury, MA (US); Shon Booker, Thousand Oaks, CA (US); Yuan Cheng, Newbury Park, CA (US); Shimin Xu, Santa Barbara, CA (US); Ning Xi, Thousand Oaks, CA (US); Joseph L. Kim, Wayland, MA (US); Andrew Tasker, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 399 days.

(21) Appl. No.: 11/042,398

(22) Filed: Jan. 24, 2005

(65) Prior Publication Data

US 2005/0245547 A1 Nov. 3, 2005

Related U.S. Application Data

(60) Provisional application No. 60/538,935, filed on Jan. 23, 2004.

(51) Int. Cl.
*C07D 215/38* (2006.01)
(52) U.S. Cl. ........................................ 546/157; 546/153
(58) Field of Classification Search .................. 546/153, 546/157; 514/312, 313
See application file for complete search history.

(56) References Cited

U.S. PATENT DOCUMENTS

| | | | |
|---|---|---|---|
| 3,755,332 A | 8/1973 | Wasley et al. | |
| 4,916,135 A | 4/1990 | Effland et al. | |
| 5,580,870 A | 12/1996 | Barker et al. | |
| 5,866,572 A | 2/1999 | Barker et al. | |
| 5,965,563 A | 10/1999 | Buzzetti et al. | |
| 6,143,764 A | 11/2000 | Kubo et al. | |
| 6,265,398 B1 | 7/2001 | Braun et al. | |
| 6,288,082 B1 | 9/2001 | Wissner et al. | |
| 6,313,129 B1 | 11/2001 | Uckun et al. | |
| 6,358,962 B2 | 3/2002 | Uckun et al. | |
| 6,399,602 B1 | 6/2002 | Barker et al. | |
| 6,469,013 B2 | 10/2002 | Uckun et al. | |
| 6,495,556 B2 | 12/2002 | Uckun et al. | |
| 6,573,289 B1 | 6/2003 | Tasaka et al. | |
| 7,091,227 B2 * | 8/2006 | Scott et al. | 514/367 |
| 2003/0018029 A1 | 1/2003 | Barker et al. | |
| 2003/0165873 A1 | 9/2003 | Come et al. | |
| 2004/0053908 A1 | 3/2004 | Funahashi et al. | |
| 2004/0242603 A1 | 12/2004 | Fujiwara et al. | |
| 2006/0142570 A1 * | 6/2006 | Herz | 546/153 |

FOREIGN PATENT DOCUMENTS

| | | |
|---|---|---|
| EP | A-0 602 851 | 6/1994 |
| EP | 1 548 008 A1 | 6/2005 |
| WO | WO 96/23774 | 8/1996 |
| WO | WO 96/29301 | 9/1996 |
| WO | WO 96/29305 | 9/1996 |
| WO | WO 97/03069 | 9/1997 |
| WO | WO 99/35132 | 7/1999 |
| WO | WO 99/54309 | 10/1999 |
| WO | WO 99/61428 | 12/1999 |
| WO | WO 00/10981 | 3/2000 |
| WO | WO 00/18761 A | 4/2000 |
| WO | WO 00/47212 | 8/2000 |
| WO | WO 00/56720 | 9/2000 |
| WO | WO 00/61580 | 10/2000 |
| WO | WO 01/70673 | 9/2001 |
| WO | WO 01/70734 | 9/2001 |
| WO | WO 02/22607 | 3/2002 |
| WO | WO 02/22608 | 3/2002 |
| WO | WO 02/30924 | 4/2002 |
| WO | WO 02/076976 | 10/2002 |
| WO | WO 02/092571 A | 11/2002 |
| WO | WO 03/040108 | 5/2003 |
| WO | WO 03/040109 | 5/2003 |
| WO | WO 03/064413 | 8/2003 |
| WO | WO 03/082272 | 10/2003 |
| WO | WO 2004/029045 | 4/2004 |
| WO | WO 2004/078114 | 9/2004 |
| WO | WO 2004/085425 | 10/2004 |
| WO | WO 2004/098604 | 11/2004 |

OTHER PUBLICATIONS

CA 135:152801, abstract only of WO 2001057008, Aug. 2001.*
CA 139:L69281, abstract only of WO 2003053446, Jul. 2003.*
CA 142:176860, abstract only of WO 2005007083, Jan. 2005.*
Anderson et al., Involvement of the protein tyrosine kinase p56$^{lck}$ in T cell signaling and thymocyte development, Advances in Immunology, 56:151-178(1994).
Appleby et al., Defective T cell receptor signaling in mice lacking the thymic isoform of p59$^{fyn}$, Cell, 70:751-763 (1992).
Asami et al., Purification and characterization of hepatocyte growth factor from injured liver of carbon tetrachloride-treated rats, Journal of Biochemistry, 109:8-13 (1991).

(Continued)

*Primary Examiner*—D. Margaret Seaman

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

25 Claims, No Drawings

OTHER PUBLICATIONS

Asano et al., Silver halide color photographic materials, Abstract 113:181318 (1990).
Boehm et al., Antiangiogenic therapy of experimental cancer does not induce acquired drug resistance, Nature, 390:404-407 (1997).
Bolen et al., Leukocyte protein tyrosine kinases: Potential targets for drug discovery, Annu. Rev. Immunology, 15:371-404 (1997).
Brazhko et al., Investigations of the biological activity 4-thioquinolines. Abstract 135:189745.
Bussolino et al., Hepatocyte growth factor is a potent angiogenic factor which stimulates endothelial cell motility and growth, The Journal of Cell Biology, 119(3):629-641 (1992).
Chan et al., Isoforms of human HGF and their biological activities, Hepatocyte Growth Factor-Scatter Factor (HGF-SF) and the C-*Met* Receptor, pp. 67-79, Goldberg and Rosen (Eds.), Birkhauser Verlag Basel, Switzerland (1993).
Chatterjee, A.K., 4-Aminoquinolines. III. Some 4-(quinolylamino)quinolines, Science and Culture 23:195 (1957).
Cockerill et al., Indazolylamino quinazolines and pyridopyrimidines as inhibitors of the EGFr and C-erbB-2, Bioorganic & Medicinal Chemistry Letters, 11:1401-1405 (2001).
Di Renzo et al., Selective expression of the *Met*/HGF receptor in human central nervous system microglia, Oncogene, 8:219-222 (1992).
Gibson et al., Epidermal growth factor receptor tyrosine kinase: Structure-activity relationships and antitumor activity of novel quinazolines, Bioorganic & Medicinal Chemistry Letters, 7(21):2723-2728 (1997).
Giordano et al., Transfer of motogenic and invasive response to scatter factor/hepatocyte growth factor by transfection of human *MET* protooncogene, Proceedings of the National Academy of Sciences, USA, 90:649-653 (1993).
Goldman et al, Defective expression of p56lck in an infant with severe combined immunodeficiency, Journal of Clinical Investigations, 102(2):421-429 (1998).
Han et al., Characterization of the DNF15S2 locus on human chromosome 3: Identification of a gene coding for four kringle domains with homology to hepatocyte growth factor, Biochemistry, 30:9768-9780 (1991).
Igawa et al., Hepatocyte growth factor is a potent mitogen for cultured rabbit renal tubular epithelial cells, Biochemical and Biophysical Research Communications, 174(2):831-838 (1991).
Jeffers et al., Hepatocyte growth factor/scatter factor-Met signaling in tumorigenicity and invasion/metastasis, J. Mol. Med., 74:505-513 (1996).
Kane et al., Signal transduction by the TCR for antigen, Current Opinion in Immunology, 12:242-249 (2000).
Kasai et al., Flexible coordination networks with fluorinated backbones, remarkable ability for induced-fit enclathration of organic molecules, Journal of American Chemical Society, 122:2140-2141 (2000).
Konishi et al., Preparation of thioquinoline derivatives as antibacterial agents for Helicobacter pylori, Chemical Abstracts 125:247631.
Lempert-Sreter et al., The synthesis of di(1-isoquinolinyl) and di(4-quinazolinyl) disulfides from 1(2H)-isoquinolinethiones and 4(3H)-quinazolinethiones, respectively, with tosyl chloride and sodium ethoxide, Acta Chemica Hungarica, 112(1):83-87 (1983).
Makisumi, Yasuo, The Thio-claisen rearrangement of allyl 4-quinolyl sulfides, Tetrahedron Letters, 51:6399-6403 (1966).
Maslankiewicz, M.J., Reactions of β- and γ-quinolinyl sulfides with a nitrating mixture, Polish Journal of Chemistry, 68(12):2545-2552 (1994).
Matsumoto et al., Hepatocyte growth factor is a potent stimulator of human melanocyte DNA synthesis and growth, Biochemical and Biophysical Research Communications, 176(1):45-51 (1991).
Matsunaga et al., $C_{17,20}$-lyase inhibitors. Part 2:Design, synthesis and structure-activity relationships of (2-naphthymethyl-1*H*-imidazoles as novel $C_{17,20}$-lyase inhibitors, Bioorganic & Medicinal Chemistry, 12:4313-4336 (2004).
Maulik et al., Role of the hepatocyte growth factor receptor, c-Met, in oncogenesis and potential for therapeutic inhibition, Cytokine & Growth Factor Reviews, 13:41-59 (2002).
Montesano et al., Induction of epithelial tubular morphogenesis in vitro by fibroblast-derived soluble factors, Cell, 66:697-711 (1991).
Monti et al., IV. Abstract 55:2681.
Moszew et al., Thermal reactions of γ-thiols in pyridine and quinoline series. Abstract 77:164418.
Nakamura et al., Partial purification and characterization of hepatocyte growth factor from serum of hepatectomized rats, Biochemical and Biophysical Research Communications, 122(3):1450-1459 (1984).
Naldini et al., Scatter factor and hepatocyte growth factor are indistinguishable ligands for the *MET* receptor, EMBO Journal, 10:2867-2878 (1991).
Park et al., Sequence of *MET* protooncogene cDNA has features characteristic of the tyrosine kinase family of growth-factor receptors, Proceedings of the National Academy of Sciences, USA, 84:6379-6383 (1987).
Renfrew, Alice G., Studies in the Quinoline Series. IV. Quinolyl Mercaptans and Sulfides, J. American Chemical Society, 1433-1436 (1946).
Di Renzo et al., Overexpression of the *c-MET/HGF* receptor gene in human thyroid carcinomas, Oncogene, 7:2549-2553 (1992).
Rubin et al., A broad-spectrum human lung fibroblast-derived mitogen is a variant of hepatocyte growth factor, Proceedings of the National Academy of Sciences, USA, 88:415-419 (1991).
Sinyak et al., The synthesis and biological properties of the derivatives of 4-heterylmercaptoquinazoline, Khimiko-Farmatsevticheskii Zhurnal, 20(2), 168-171 (1986). Abstract 104:199594.
Solbreux et al., Extrahepatic bile duct growth in mice repeatedly injected with human normal serum, IgA-deficient serum or purified secretory IgA, Hepatology, 13:735-742 (1991).
Soriano et al., Targeted disruption of the c-*src* proto-oncogene leads to osteopetrosis in mice, Cell, 64:693-702 (1991).
Stern et al., Epithelial scatter factor and development of the chick embryonic axis, Development 110:1271-1284 (1990).
Stoker et al., Scatter factor is a fibroblast-derived modulator of epithelial cell mobility, Nature, 327:239-242 (1987).
Thakore, P.V. et al., Studies in the synthesis of quinoline derivatives. Part VIII. Synthesis of 4:3'-methylenebis(2,2'-dichloro-4'-methylquinoline) derivatives, Journal of the Indian Chemical Society, 54(12):1204-1206 (1977).
Turner et al., Signalling through the high-affinity IgE receptor FcεRI, Nature, 402:B24-B30 (1999).
Vicentini et al., Fgr deficiency results in defective eosinophil recruitment to the lung during allergic airway inflammation, The Journal of Immunology, 168:6446-6454 (2002).
Weidner et al., Scatter Factor: Molecular characteristics and effect on the invasiveness of epithelial cells, The Journal of Cell Biology, 111:2097-2108 (1990).
Wyszormirski et al., Conformations of monosubsituted and disubstituted 3,4'-, 3,3'- and 4,4'-diquinolinyl sulfides studied by NMR spectroscopy, Phosphorus, Sulfur, and Silicon, 95-96:415-416 (1994).
Zhang et al., Synthesis and antimalarial activity of 2-dialkylaminomethyl-4-(heterocyclic amino)-5,6,7,8-tetrahydronaphthol derivatives. Abstract 103:87753.
Zhang et al., Synthesis and SAR of potent EGFR/erbB2 dual inhibitors, Bioorganic & Medicinal Chemistry Letters, 14:111-114 (2004).
Breier et al., "The role of vascular endothelial growth factor in blood vessel formation", Trends in Cell Biology, 6:454-456 (1996).
Paolo M. Comoglio, "Structure, biosynthesis and biochemical properties of the HGF receptor in normal and malignant cells", Hepatocyte Growth Factor-Scatter Factor (HGF-SF) and the C-*Met* Receptor, eds. Goldberg and Rosen, Birkhauser Verlag Basel, Switzerland, 131-165 (1993).
Connell et al., "Patent focus on cancer chemotherapeutics. II Angiogenesis agents: Apr. 2000-Sep. 2000", Expert Opinion on Therapeutic Patents, 11(1):77-114 (2001).

* cited by examiner

COMPOUNDS AND METHODS OF USE

This application claims the benefit of U.S. Provisional Application No. 60/538,935 filed Jan. 23, 2004, which is hereby incorporated by reference.

FIELD OF THE INVENTION

This invention is in the field of pharmaceutical agents and specifically relates to compounds, compositions, uses and methods for treating inflammation, angiogenesis and cancer.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-Met (Hepatocyte Growth Factor-Scatter Factor (HGF-SF) and the c-Met Receptor, Goldberg and Rosen, eds., Birkhauser Verlag-Basel, 67-79 (1993)). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. USA, 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met protooncogene have been postulated to play a role in microglial reactions to CNS injuries (Oncogene, 8:219-222 (1993)).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound.

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction is the kinase enzymes Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(-/-) mice have abnormalities in bone remodeling or osteopetrosis (Soriano, P. Cell 1991, 64, 693), suggesting that inhibition of this kinase might be useful in diseases of bone resorption, such as osteoporosis. Lck(-/-) mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

PCT publication WO 03/000660 describes substituted phenyl compounds. Substituted quinolines are described in U.S. Pat. No. 6,143,764. Substituted benzazoles are described in WO 03/82272. Benzimidazoles are described in WO 00/61580. WO 02/32872 describes substituted quinolines. WO 00/47212 describes substituted quinazoline derivatives. WO 96/23774 describes thioquinoline compounds.

Compounds of the current invention have not been described for the treatment of cancer.

DESCRIPTION OF THE INVENTION

A class of compounds useful in treating cancer and angiogenesis is defined by Formula I

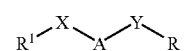

I wherein R is selected from substituted or unsubstituted aryl, substituted or unsubstituted heterocyclyl, substituted or unsubstituted cycloalkyl, substituted or unsubstituted cycloalkenyl, H, substituted or unsubstituted alkyl, and substituted or unsubstituted alkenyl and substituted or unsubstituted alkynyl;

wherein $R^1$ is selected from substituted or unsubstituted 5-14-membered nitrogen containing heterocyclyl;

wherein A is an optionally substituted nine membered bicyclic ring comprising at least one aromatic ring;

wherein X is selected from O, S, $NR^2$ and $CR^3R^4$;

wherein Y is selected from $-NR^b(CR^3R^4)_p-$, $-NR^bC(=O)(CR^3R^4)_p-$, $-NR^bC(=O)NR^b(CR^3R^4)_p-$, $-NR^bC(=O)(CR^3R^4)_pO-$, $-NR^bC(=O)O(CR^3R^4)_p-$, $-NR^bC(=S)(CR^3R^4)_p-$, $-NR^bC(=NR^a)(CR^3R^4)_p-$, $-NR^bSO_2-(CR^3R^4)_p-$, $-OC(=O)(CR^3R^4)_p-$, $-O(CR^3R^4)_p-$, $-(CR^3R^4)_p-S(=O)_t-$, $-(CR^3R^4)_p-$, $-S(=O)_tNR^b(CR^3R^4)_p-$, $-S(=O)_t(CR^3R^4)_p-$, $-C(=O)(CR^3R^4)_p-$, $-C(=NR^a)NH(CR^3R^4)_p-$, $-C(=S)NH(CR^3R^4)_p-$ and $-C(=O)NH(CR^3R^4)_p-$; wherein Y is in either direction;

wherein $R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N-(C=O)-$, and $R^5-(=O)-$; wherein each of $R^a$ and $R^b$ is optionally substituted;

wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;

wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

wherein $R^5$ is selected from H, alkyl, haloalkyl, arylalkyl, heterocyclylalkyl, cycloalkylalkyl, aryl, heterocyclyl, alkenyl, alkynyl and cycloalkyl;

wherein $R^6$ is selected from cyano, $-OR^2$, $-SR^2$, halo, $-SO_2R^2$, $-C(=O)R^2$, $-SO_2NR^2R^5$, $-NR^5C(=O)OR^2$, $-NR^5C(=O)NR^5R^2$, $-NR^5C(=O)R^2$, $-CO_2R^2$, $-C(=O)NR^2R^5$ and $-NR^2R^5$;

wherein p is 0, 1, 2, or 3; and wherein t is 0, 1 or 2;

and pharmaceutically acceptable derivatives thereof.

The invention also relates to compounds of Formula I R is selected from H, 6-10 membered aryl, 4-10 membered heterocyclyl, 4-6 membered cycloalkyl, $C_{1-6}$-alkyl, $C_{2-6}$-alkenyl and $C_{2-6}$-alkynyl; wherein R is substituted or unsubstituted; in conjunction with any of the above or below embodiments.

The invention also relates to compounds of Formula I wherein R is phenyl or naphthyl; in conjunction with any of the above or below embodiments.

The invention also relates to compounds of Formula I R is a substituted or unsubstituted heterocyclyl ring selected from pyrrolidinyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl; in conjunction with any of the above or below embodiments.

The invention also relates to compounds of Formula I wherein R is 4-6 membered cycloalkyl selected from cyclobutyl, cyclopentyl and cyclohexyl; in conjunction with any of the above or below embodiments.

The invention also relates to compounds of Formula I wherein R is selected from methyl, ethyl, propyl, butyl and pentyl; in conjunction with any of the above or below embodiments.

The invention also relates to compounds of Formula I wherein R is selected from ethenyl and propenyl; in conjunction with any of the above or below embodiments.

The invention also relates to compounds of Formula I wherein A is selected from

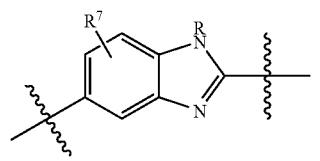

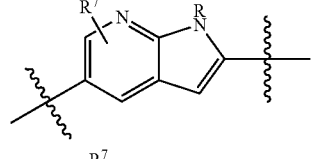

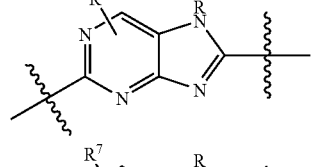

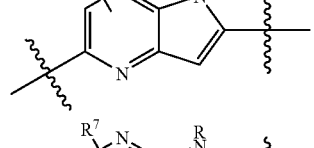

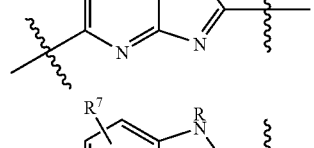

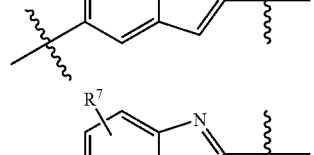

-continued

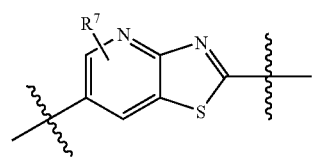

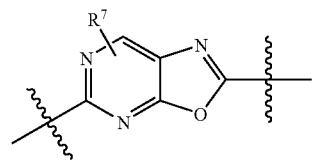

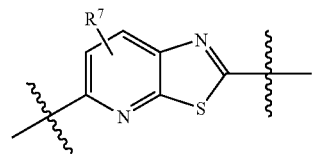

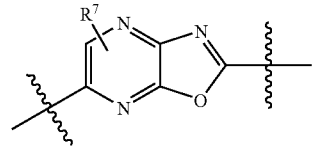

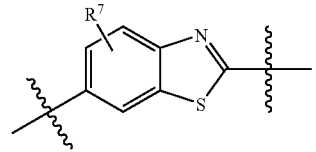

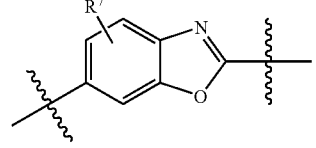

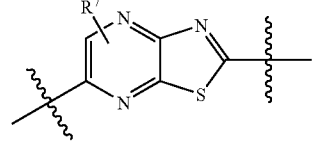

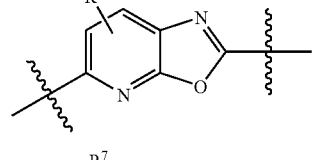

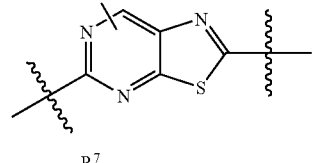

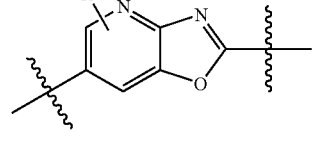

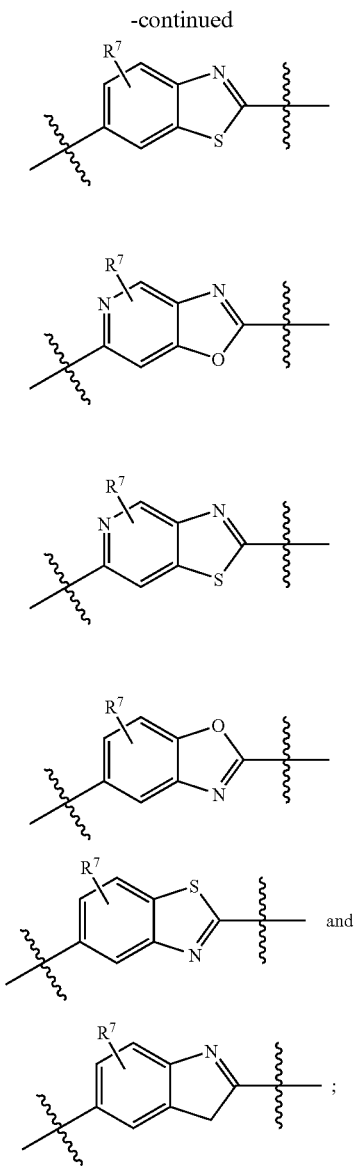

wherein R[7] is selected from H, halo and methyl;

and pharmaceutically acceptable derivatives thereof; in conjunction with any of the above or below embodiments.

The invention also relates to compounds of Formula I wherein A is benzothiazole; and pharmaceutically acceptable derivatives thereof; in conjunction with any of the above or below embodiments.

The invention also relates to compounds of Formula I wherein R[1] is selected from 9-10-membered bicyclic heterocyclyl; in conjunction with any of the above or below embodiments.

The invention also relates to compounds of Formula I wherein R[1] is selected from 9-10-membered bicyclic heteroaryl; in conjunction with any of the above or below embodiments.

The invention also relates to compounds of Formula I wherein R[1] is selected from wherein ring T is selected from phenyl and 5-6-membered heteroaryl; wherein Z is selected from N or CH; wherein R[10] is one or more substituents selected from R[5]O—; and wherein R[5] is selected from $C_{1-6}$-alkyl, $C_{1-6}$-haloalkyl, $C_{1-6}$-alkylamino-$C_{1-6}$-alkyl, aryl-$C_{1-6}$-alkyl, heterocyclyl-$C_{1-6}$-alkyl, cycloalkyl-$C_{1-6}$-alkyl, aryl, heterocyclyl, and cycloalkyl; in conjunction with any of the above or below embodiments.

The invention also relates to compounds of Formula I wherein R[1] is selected from and wherein R[10] is selected from $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy; in conjunction with any of the above or below embodiments.

The invention also relates to compounds of Formula I wherein R[1] is selected from 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl; in conjunction with any of the above or below embodiments.

The invention also relates to compounds of Formula I wherein Y is selected from —NH(CH$_2$)$_p$—, —NHC(=O)(CH$_2$)$_p$—, —NHC(=O)(CH$_2$)$_p$O—, —NHC(=O)O(CH$_2$)$_p$—, CH$_2$)$_p$—NHC(=O)—, —NHC(=O)NH—, —C(=O)O—, —NHSO$_2$—, and —C(=O)NH(CH$_2$)$_p$—; and wherein p is 0, 1, or 2; in conjunction with any of the above or below embodiments.

The invention also relates to compounds of Formula I wherein Y is selected from —NH—, —NHCH$_2$—, —NH(CH$_2$)$_2$—, —NH(CH$_2$)$_3$—, —NHC(=O)CH$_2$—, —NHC(=O)(CH$_2$)$_2$—, —NHC(=O)—, —NHC(=O)CH$_2$O—, —NHC(=O)OCH$_2$—, —NHC(=O)NH—, —(CH$_2$)NHC(=O)—, —C(=O)O—, —NHSO$_2$—, and —C(=O)NHCH$_2$—; in conjunction with any of the above or below embodiments.

The invention also relates to compounds of Formula I wherein R is selected from ethyl, isopropyl, (CH$_3$)$_3$CCH$_2$—, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein A is naphthyl; wherein X is —O— or —CH$_2$—; wherein Y is selected from —NHC(=O)—, —NHC(=O)(CH$_2$)—, —NHC(=O)(CH$_2$)$_2$—, —(CH$_2$)$_p$—NHC(=O)—, —NHC(=O)NH— and —NHSO$_2$—; and wherein R$^1$ is selected from 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl; and pharmaceutically acceptable derivatives thereof; in conjunction with any of the above or below embodiments.

The invention also relates to compounds of Formula I and pharmaceutically acceptable salts thereof selected from N-[6-(6,7-Dimethoxy-quinolin-4-yloxy)-benzothiazol-2-yl]-3-methyl-benzamide;

Thiophene-3-carboxylic acid [6-(6,7-dimethoxy-quinolin-4-yloxy)-benzothiazol-2-yl]-amide;

2-Phenyl-N-[6-(7-trifluoromethyl-quinolin-4-yloxy)-benzothiazol-2-yl]-acetamide;

N-[6-(2-Methyl-pyridin-4-yloxy)-benzothiazol-2-yl]-2-phenyl-acetamide;

4-Chloro-N-[6-(6,7-dimethoxy-quinolin-4-yloxy)-benzothiazol-2-yl]-benzamide;

5-((6,7-bis(methoxy)-4-quinolinyl)oxy)-N-(4-chlorophenyl)-1,3-benzoxazol-2-amine;

N-(6-((7-((2-(dimethylamino)ethyl)oxy)-6-(methoxy)-4-quinolinyl)oxy)-1,3-benzothiazol-2-yl)-2-thiophenecarboxamide;

N-(6-((7-((2-(dimethylamino)ethyl)oxy)-6-(methoxy)-4-quinolinyl)oxy)-1,3-benzothiazol-2-yl)-3-thiophenecarboxamide;

N-(6-((7-((3-(dimethylamino)propyl)oxy)-6-(methoxy)-4-quinolinyl)oxy)-1,3-benzothiazol-2-yl)benzamide; AND N-(6-((6-(methoxy)-7-((3-(4-morpholinyl)propyl)oxy)-4-quinolinyl)oxy)-1,3-benzothiazol-2-yl)-3-thiophenecarboxamide.

The invention also relates to compounds of Formula I'

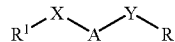

wherein R is selected from
a) substituted or unsubstituted aryl,
b) substituted or unsubstituted heterocyclyl,
c) substituted or unsubstituted cycloalkyl,
d) substituted or unsubstituted cycloalkenyl,
e) H,
f) substituted or unsubstituted alkyl,
g) substituted or unsubstituted alkenyl,
h) substituted or unsubstituted alkynyl,
i) alkylaminocarbonyl,
j) aminocarbonyl, and
k) cyano;

wherein R$^1$ is

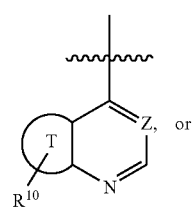

a)

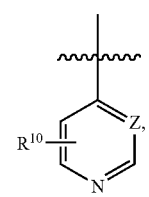

b)

wherein ring T is selected from phenyl and 5-6-membered heteroaryl; wherein Z is selected from N or CR$^x$; wherein R$^x$ is selected from H, CN, NH$_2$, F, alkycarbonyl amino, and alkylaminocarbonyl; wherein R$^{10}$ is one or more substituents selected from C$_{1-6}$-alkoxy, C$_{1-6}$-haloalkoxy, C$_{1-6}$-alkiylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$-(hydroxyalkoxy), C$_{1-6}$-alkoxyalkoxy, aryloxy-C$_{1-6}$-alkoxy, heterocycly-loxy-C$_{1-6}$-alkoxy, cycloalkyloxy-C$_{1-6}$-alkoxy, aryloxy, heterocyclyloxy, and cycloalkyloxy;

wherein A is selected from the following:

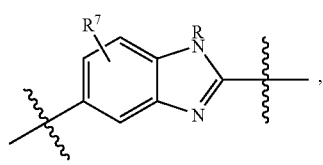

(a)

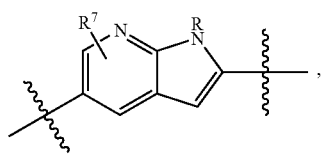

(b)

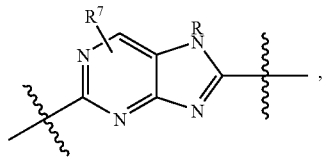

(c)

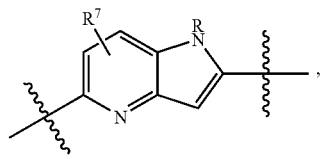

(d)

-continued
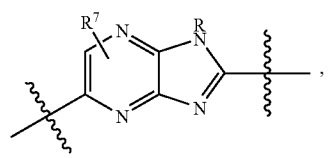 (e)
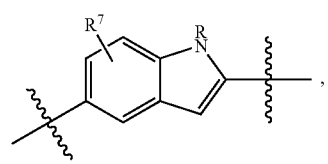 (f)
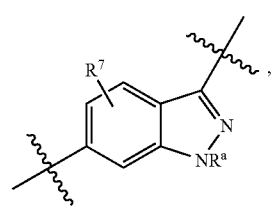 (g)
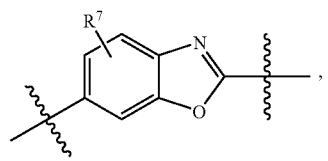 (h)
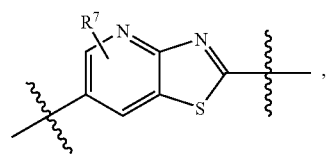 (i)
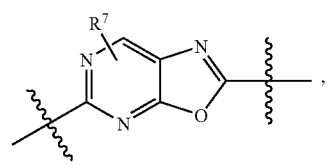 (j)
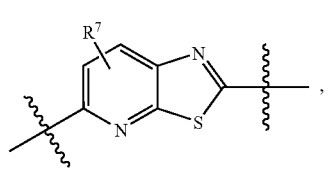 (k)
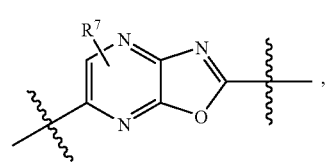 (l)
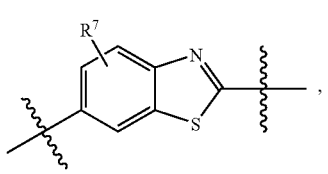 (m)
-continued
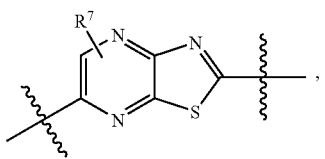 (n)
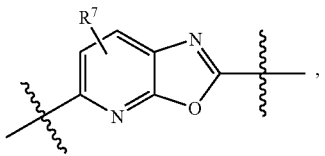 (o)
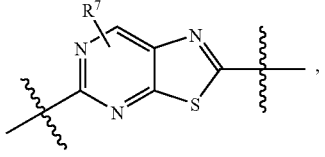 (p)
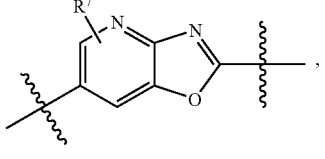 (q)
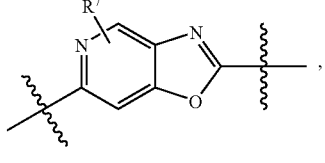 (r)
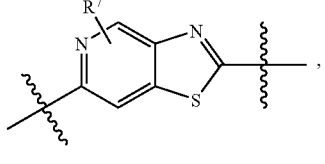 (s)
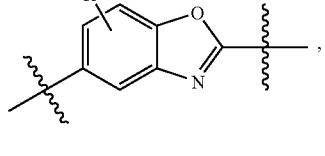 (t)
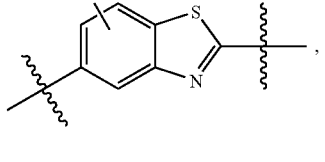 (u)
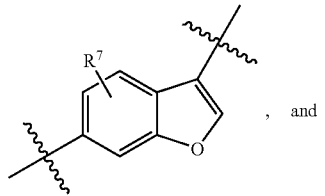, and (v)

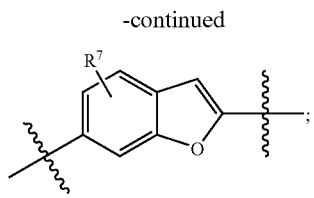

wherein X is selected from O, S, NR² and CR³R⁴;

wherein Y is selected from —NR$^b$(CR³R⁴)$_p$—, —NR$^b$C(=O)(CR³R⁴)$_p$—, —NR$^b$C(=O)NR$^b$(CR³R⁴)$_p$—, —NR$^b$C(=O)(CR³R⁴)$_p$O—, —NR$^b$C(=O)O(CR³R⁴)$_p$—, —NR$^b$C(=S)(CR³R⁴)$_p$—, —NR$^b$C(=NR$^a$)(CR³R⁴)$_p$—, —NR$^b$SO$_2$—(CR³R⁴)$_p$—, —OC(=O)(CR³R⁴)$_p$—, —O(CR³R⁴)$_p$—, —(CR³R⁴)$_p$—S(=O)$_t$—, —(CR³R⁴)$_p$—, —S(=O)$_t$NR$^b$(CR³R⁴)$_p$—, —S(=O)$_t$(CR³R⁴)$_p$—, —C(=O)(CR³R⁴)$_p$—, —C(=NR$^a$)NH(CR³R⁴)$_p$—, —C(=S)NH(CR³R⁴)$_p$— and —C(=O)NH(CR³R⁴)$_p$—; wherein Y is in either direction;

wherein R$^a$ and R$^b$ is each independently selected from H, alkyl, heterocyclyl, aryl, arylalkyl, heterocyclylalkyl, cycloalkyl, cycloalkylalkyl, alkenyl, alkynyl, R⁵R⁵N—(C=O)—, and R⁵—(=O)—; wherein each of R$^a$ and R$^b$ is optionally substituted;

wherein R² is selected from H, alkyl, haloalkyl, aryl, heterocyclyl, arylalkyl, heterocyclylalkyl, cycloalkyl, cycloalkylalkyl, alkenyl, alkynyl and R⁵-carbonyl;

wherein R³ and R⁴ is each independently selected from H, alkyl, aryl, heterocyclyl, arylalkyl, heterocyclylalkyl, haloalkyl, cycloalkyl, cycloalkylalkyl, R⁶ and alkyl substituted with R⁶;

wherein R⁵ is selected from H, alkyl, haloalkyl, arylalkyl, heterocyclylalkyl, cycloalkylalkyl, aryl, heterocyclyl, alkenyl, alkynyl and cycloalkyl;

wherein R⁶ is selected from cyano, —OR², —SR², halo, —SO₂R², —C(=O)R², —SO₂NR²R⁵, —NR⁵C(=O)OR², —NR⁵C(=O)NR⁵R², —NR⁵C(=O)R², —CO₂R², —C(=O)NR²R⁵ and —NR²R⁵;

wherein p is 0, 1, 2, or 3; and
wherein t is 0, 1 or 2;
and pharmaceutically acceptable derivatives thereof;

provided R is not 4-chloro-3-(1-methylpyrrolidin-2-yl)phenyl when Y is NH and A is 2,5-benzoxazolyl and when R¹ is 6,7-dimethoxyquinolinyl; further provided R is not 4-chloro-3-(1-methylpyrrolidin-2-yl)phenyl when Y is NH and A is 2,5-benzoxazolyl and when R¹ is 6,7-dimethoxyquinazolinyl; further provided R is not phenyl when Y is CH₂ and A is 2,5-benzimidazolyl and when R¹ is 6,7-dimethoxyquinolinyl; further provided Y is not —NH— or —NMe— when X is O, S, CH₂ or NH, and A is benzimidazolyl, benzoxazolyl or benzothiazolyl; and further provided R is not methyl when Y is —(CR³R⁴)$_p$—, when p is 0, and A is 2,5-indolyl.

The invention also relates to compounds of Formula I' wherein R is selected from H, 6-10 membered aryl, 4-10 membered heterocyclyl, 3-6 membered cycloalkyl, C$_{1-6}$-alkyl, C$_{2-6}$-alkenyl and C$_{2-6}$-alkynyl; wherein R is substituted or unsubstituted.

The invention also relates to compounds of Formula I' wherein R is optionally substituted phenyl or optionally substituted naphthyl.

The invention also relates to compounds of Formula I' wherein R is a substituted or unsubstituted heterocyclyl ring selected from pyrrolidinyl, pyrrolyl, imidazolyl, pyrazolyl, pyrazinyl, pyrimidinyl, pyridyl, quinolinyl, isoquinolinyl, tetrahydrofuryl, 2,3-dihydrothiazolyl, 2,3-dihydrobenzofuryl, 2,3-dihydro-1,4-benzodioxinyl, 1,3-benzodioxolyl, benzisoxazolyl, benzthiazolyl, benzimidazolyl, benzothiadiazolyl, indolinyl, imidazo[1,2-a]pyridyl, isoxazolyl, isothiazolyl, oxazolyl, thiazolyl, thiadiazolyl, furanyl, and thienyl.

The invention also relates to compounds of Formula I' wherein R is an unsubstituted or substituted ring selected from 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl.

The invention also relates to compounds of Formula I' wherein R is selected from 1-methyl-cyclopropyl, cyclopropyl, 2-fluorocyclopropyl, cyclobutyl, cyclopentyl and cyclohexyl.

The invention also relates to compounds of Formula I' wherein R is selected from methyl, trifluoromethyl, ethyl, propyl, butyl and pentyl.

The invention also relates to compounds of Formula I' wherein R is selected from cyclohexenyl, ethenyl and propenyl.

The invention also relates to compounds of Formula I' wherein R is H.

The invention also relates to compounds of Formula I' wherein R is dimethylamino.

The invention also relates to compounds of Formula I' wherein A is selected from

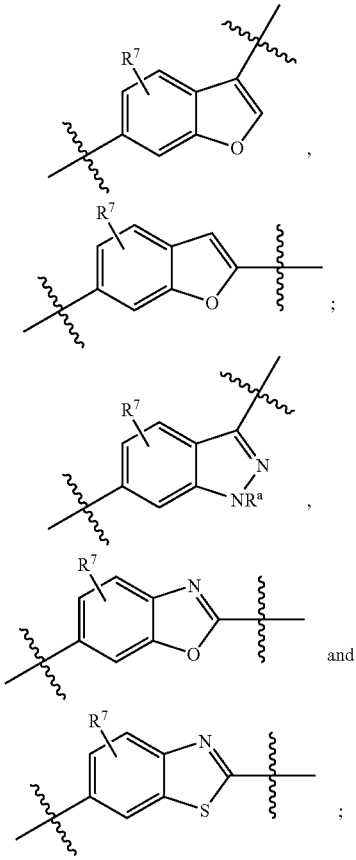

wherein R⁷ is selected from H, halo and methyl.

The invention also relates to compounds of Formula I' wherein A is

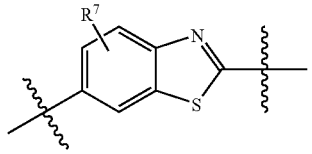

The invention also relates to compounds of Formula I' wherein A is

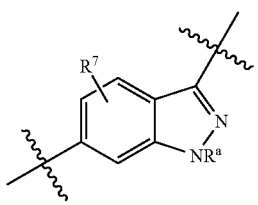

The invention also relates to compounds of Formula I' wherein

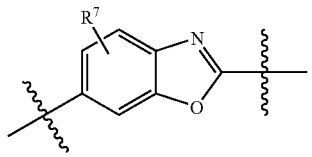

The invention also relates to compounds of Formula I' wherein $R^1$ is

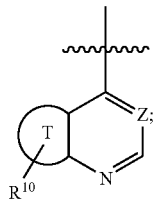

wherein ring T is selected from phenyl and 5-6-membered heteroaryl; wherein Z is selected from N or CH; wherein $R^{10}$ is one or more substituents selected from $R^8O$—; and wherein $R^8$ is selected from $C_{1-6}$-alkyl, $C_{1-6}$-haloalkyl, $C_{1-6}$-alkylamino-$C_{1-6}$-alkyl, aryl-$C_{1-6}$-alkyl, heterocyclyl-$C_{1-6}$-alkyl, cycloalkyl-$C_{1-6}$-alkyl, heterocyclyl-$C_{1-6}$-(hydroxyalkyl), cycloalkyl-$C_{1-6}$-(hydroxyalkyl), aryl-$C_{1-6}$-(hydroxyalkyl), $C_{1-6}$-alkoxyalkyl, aryloxy-$C_{1-6}$-alkyl, heterocyclyloxy-$C_{1-6}$-alkyl, cycloalkyloxy-$C_{1-6}$-alkyl, aryl, heterocyclyl, and cycloalkyl.

The invention also relates to compounds of Formula I' wherein $R^1$ is selected from

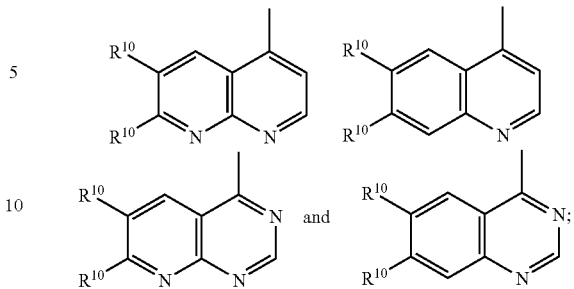

and wherein $R^{10}$ is selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), phenyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy.

The invention also relates to compounds of Formula I' wherein $R^1$ is selected from 6,7-dimethoxy-4-quinolinyl, 6-methoxy-7-(dimethylaminopropoxy)-4-quinolinyl, 6-methoxy-7-(4-morpholinylpropoxy)-4-quinolinyl, 6,7-dimethoxy-4-quinazolinyl, and 6-methoxy-7-(dimethylaminopropoxy)-4-quinazolinyl.

The invention also relates to compounds of Formula I' wherein Y is selected from —NH(CH$_2$)$_p$—, —NHC(=O)(CH$_2$)$_p$—, —NHC(=O)(CH$_2$)$_p$O—, —NHC(=O)O(CH$_2$)$_p$—, —(CH$_2$)$_p$—NHC(=O)—, —NHC(=O)NH—, —C(=O)O—, —NHSO$_2$—, and —C(=O)NH(CH$_2$)$_p$—; and wherein p is 0, 1, or 2.

The invention also relates to compounds of Formula I' wherein Y is selected from —NH—, —NHCH$_2$—, —NH(CH$_2$)$_2$—, —NH(CH$_2$)$_3$—, —NHC(=O)CH$_2$—, —NHC(=O)(CH$_2$)$_2$—, —NHC(=O)—, —NHC(=O)CH$_2$O—, —NHC(=O)OCH$_2$—, —NHC(=O)NH—, —(CH$_2$)NHC(=O)—, —C(=O)O—, —NHSO$_2$—, and —C(=O)NHCH$_2$—.

The invention also relates to compounds of Formula I' wherein R is selected from cyclopropyl, cyclobutyl, cyclopentyl, cyclohexyl, phenyl, 4-methylphenyl, 3-methylphenyl, 2-methylphenyl, 2-ethylphenyl, 4-tert-butyl-phenyl, 2,3-dimethylphenyl, 4-fluorophenyl, 3-fluorophenyl, 2-fluorophenyl, 2,4-difluorophenyl, 3,4-difluorophenyl, 4-bromophenyl, 4-chlorophenyl, 3-chlorophenyl, 2-chlorophenyl, 2,4-dichlorophenyl, 3-chloro-4-fluorophenyl, 2-methoxyphenyl, 3-methoxyphenyl, 4-methoxyphenyl, 4-methylthiophenyl, 3-methylsulfonylphenyl, 2-methylsulfonylphenyl, 4-trifluoromethoxyphenyl, 4-trifluoromethylphenyl, 3-trifluoromethylphenyl, 2-trifluoromethylphenyl, 4-chloro-3-trifluoromethylphenyl, 2-chloro-4-trifluoromethylphenyl, 3,5-di(trifluoromethyl)phenyl, 4-dimethylaminophenyl, 3-(4-methylpiperazin-1-ymethyl)phenyl, 2-(4-methylpiperazin-1-ymethyl)phenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 2-[methyl-(1-methylpyrrolidin-3-yl)amino]-5-trifluoromethylphenyl, 2-pyrrolidinyl, 1-methyl-2-pyrrolidinyl, 4-piperazinyl, 2-pyrrolyl, 1-methyl-2-pyrrolyl, 5-imidazolyl, 3-pyrazolyl, 2-pyrazinyl, 5-methyl-2-pyrazinyl, 4-pyrimidinyl, 2,6-dimethoxy-4-pyrimidinyl, 2-pyridyl, 3-pyridyl, 2-chloro-3-pyridyl, 2-chloro-5-pyridyl, 4-chloro-2-pyridyl, 4-methoxy-5-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 4,5-dichloro-3-isothiazolyl, 5-oxazolyl, 4-thiazolyl, 2-methyl-4-thiazolyl, 2,5-dimethyl-4-thiazolyl, 2-thiazolyl, 2-furanyl, 4,5-dimethyl-2-furyl, 5-methyl-2-trifluoromethyl-3-furyl, 3-furanyl, 3-thienyl, 4-methoxy-5-chloro-3-thienyl, 2-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 5-tert-butyl-isoxazol-3-yl, 5-methyl-isoxazol-3-yl, 3,5-dimethyl-isoxazol-4-yl, 5-tert-butyl-pyrazol-3-yl, and 2-methylbenzothiazol-5-yl.

The invention also relates to compounds of Formula I' wherein X is O.

The invention also relates to compounds of Formula I' selected from
N-[6-(6,7-Dimethoxy-quinolin-4-yloxy)-benzothiazol-2-yl]-3-methyl-benzamide;
Thiophene-3-carboxylic acid [6-(6,7-dimethoxy-quinolin-4-yloxy)-benzothiazol-2-yl]-amide;
2-Phenyl-N-[6-(7-trifluoromethyl-quinolin-4-yloxy)-benzothiazol-2-yl]-acetamide;
N-[6-(2-Methyl-pyridin-4-yloxy)-benzothiazol-2-yl]-2-phenyl-acetamide;
4-Chloro-N-[6-(6,7-dimethoxy-quinolin-4-yloxy)-benzothiazol-2-yl]-benzamide;
5-((6,7-bis(methoxy)-4-quinolinyl)oxy)-N-(4-chlorophenyl)-1,3-benzoxazol-2-amine;
N-(6-((7-((2-(dimethylamino)ethyl)oxy)-6-(methoxy)-4-quinolinyl)oxy)-1,3-benzothiazol-2-yl)-2-thiophenecarboxamide;
N-(6-((7-((2-(dimethylamino)ethyl)oxy)-6-(methoxy)-4-quinolinyl)oxy)-1,3-benzothiazol-2-yl)-3-thiophenecarboxamide;
N-(6-((7-((3-(dimethylamino)propyl)oxy)-6-(methoxy)-4-quinolinyl)oxy)-1,3-benzothiazol-2-yl)benzamide; AND
N-(6-((6-(methoxy)-7-((3-(4-morpholinyl)propyl)oxy)-4-quinolinyl)oxy)-1,3-benzothiazol-2-yl)-3-thiophenecarboxamide.

The invention also relates to compounds of Formula II

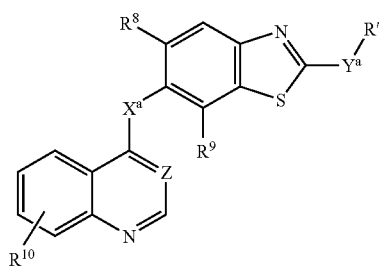

II wherein $X^a$ is O or $CH_2$;
wherein $Y^a$ is selected from —NH(CH$_2$)$_p$—, —NHC(=O)(CH$_2$)$_p$—, —NHC(=O)(CH$_2$)$_p$O—, —CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—;
wherein p is 0, 1, 2, or 3; or Y is a bond if R is thienyl;
wherein Z is CH or N;
wherein R' is selected from H, $C_{1-5}$-alkyl, $C_{2-4}$-alkenyl, and an unsubstituted or substituted ring selected from phenyl, $C_{3-6}$-cycloalkyl, pyrrolidinyl, pyrrolyl, imidazolyl, pyrazolyl, pyrazinyl, pyrimidinyl, pyridyl, quinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl and thienyl;
wherein $R^8$ is selected from H, fluoro, chloro and methyl;
wherein $R^9$ is selected from H, methyl and fluoro; and
wherein $R^{10}$ is one or more substituents selected from 5 or 6-membered heterocyclyl-$C_{1-3}$-alkoxy, $C_{1-2}$-alkylamino-$C_{1-4}$-alkoxy, and $C_{1-4}$-alkoxy;
and pharmaceutically acceptable derivatives thereof;
provided R is not methyl when Y is —CO$_2$—.

The invention also relates to compounds of Formula II wherein $X^a$ is O; wherein $Y^a$ is selected from —NHC(=O)(CH$_2$)$_p$—, —NHC(=O)(CH$_2$)$_p$O—, —CH$_2$)$_p$—NHC(=O)—, —NHC(=O)NH—, —NHC(=O)O(CH$_2$)$_p$—, —NHSO$_2$—, and —C(=O)NH(CH$_2$)$_p$—; wherein p is 0, 1, 2, or 3; wherein R' is selected from ethyl, isopropyl, (CH$_3$)$_3$CCH$_2$—, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein $R^{10}$ is one or more substituents selected from 4-morpholinopropoxy, 1-pyrrolidinylethoxy, dimethylaminoethoxy, dimethylaminopropoxy and methoxy; wherein $R^{10}$ is attached at positions 6 and 7 of the quinolin-4-yl or quinazolin-4-yl ring; wherein $R^8$ is H; and wherein $R^9$ is H, methyl or fluoro; and pharmaceutically acceptable derivatives thereof; in conjunction with any of the above or below embodiments.

The invention also relates to compounds of Formula II wherein $Y^a$ is selected from —NHC(=O)—, —NHC(=O)(CH$_2$)—, —NHC(=O)(CH$_2$)$_2$—, —CH$_2$)$_p$—NHC(=O)—, —NHC(=O)NH— and —NHSO$_2$—; and pharmaceutically acceptable derivatives thereof; in conjunction with any of the above or below embodiments.

The invention also relates to compounds of Formula II wherein $Y^a$ is —NHC(=O)— and —NHC(=O)NH—; and pharmaceutically acceptable derivatives thereof; in conjunction with any of the above or below embodiments.

The invention also relates to compounds of Formula II wherein R' is an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; and pharmaceutically acceptable derivatives thereof; in conjunction with any of the above or below embodiments.

The invention also relates to compounds of Formula II wherein R' is a ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein the ring is substituted with or two substituents selected from methoxymethylthio, 4-methylpiperazin-1-ylmethyl, trifluoromethyl, methyl, bromo, chloro, fluoro and tert-butyl; and pharmaceutically acceptable derivatives thereof; in conjunction with any of the above or below embodiments.

The invention also relates to compounds of Formula II wherein $R^8$ is H; and wherein $R^9$ is H or fluoro; and pharmaceutically acceptable derivatives thereof; in conjunction with any of the above or below embodiments.

The invention also relates to compounds of

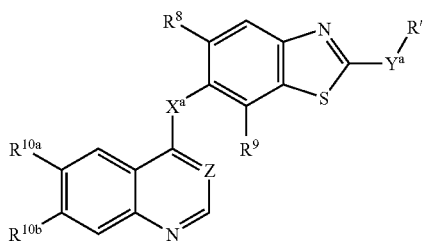

II' wherein $X^a$ is O or $CH_2$;

wherein $Y^a$ is selected from —NH($CH_2$)$_{1-3}$—, —NHC(=O)($CH_2$)$_p$—, —NHC(=O)($CH_2$)$_p$O—, —($CH_2$)$_p$—NHC(=O)—, —NHC(=O)NH—, —NHC(=O)O($CH_2$)$_p$—, and —C(=O)O—;

wherein Z is CH or N;

wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkylaminocarbonyl-$C_{1-5}$-alkyl, amino-$C_{1-5}$-alkyl, $C_{1-5}$-alkylamino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, 2,3-dihydro-1,4-benzodioxinyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, piperidinyl, 1-methyl-oxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^8$ is selected from H, fluoro, chloro and methyl;

wherein $R^9$ is selected from H, methyl and fluoro;

wherein $R^{10a}$ is H or methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

The invention also relates to compounds of wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH($CH_3$)—, phenyl-CH($CH_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, ($CH_3$)$_3$C$CH_2$—, pentafluoroethyl, $CF_3CH_2CH_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N($CH_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ymethyl)phenyl, 2-(4-methylpiperazin-1-ymethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydro-indol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy.

The invention also relates to compounds of wherein $R^8$ is H; and wherein $R^9$ is H, methyl or fluoro.

The invention also relates to compounds of wherein $Y^a$ is selected from —NHC(=O)(CH$_2$)$_p$—, —NHC(=O)(CH$_2$)$_p$O—, —CH$_2$)$_p$—NHC(=O)—, —NHC(=O)NH—, —NHC(=O)O(CH$_2$)$_p$—, —NHSO$_2$—, and —C(=O)NH(CH$_2$)$_p$—; wherein p is 0, 1, 2, or 3.

The invention also relates to compounds of wherein $Y^a$ is selected from —NHC(=O)—, —NHC(=O)(CH$_2$)—, —NHC(=O)(CH$_2$)$_2$—, —CH$_2$)$_p$—NHC(=O)—, —NHC(=O)NH— and —NHSO$_2$—.

The invention also relates to compounds of wherein $Y^a$ is —NHC(=O)— and —NHC(=O)CH$_2$—.

The invention also relates to compounds of wherein X is O.

The invention also relates to compounds of wherein R' is selected from cyclopropyl, cyclobutyl, cyclopentyl, cyclohexyl, phenyl, 4-methylphenyl, 3-methylphenyl, 2-methylphenyl, 2-ethylphenyl, 3-isopropylphenyl, 4-tert-butylphenyl, 2,3-dimethylphenyl, 4-isopropyl-3-methylphenyl, 3-chloro-4-methylphenyl, 4-fluorophenyl, 3-fluorophenyl, 2-fluorophenyl, 2,4-difluorophenyl, 3,4-difluorophenyl, 4-bromophenyl, 4-chlorophenyl, 3-chlorophenyl, 2-chlorophenyl, 2,4-dichlorophenyl, 3,4-dichlorophenyl, 3-chloro-4-fluorophenyl, 2-methoxyphenyl, 3-methoxyphenyl, 4-methoxyphenyl, 4-methylthiophenyl, 3-methylsulfonylphenyl, 2-methylsulfonylphenyl, 4-trifluoromethoxyphenyl, 3-trifluoromethoxyphenyl, 4-trifluoromethylphenyl, 3-trifluoromethylphenyl, 2-trifluoromethylphenyl, 4-chloro-3-trifluoromethylphenyl, 2-chloro-4-trifluoromethylphenyl, 3,5-di(trifluoromethyl)phenyl, 4-dimethylaminophenyl, 3-(4-methylpiperazin-1-ymethyl)phenyl, 2-(4-methylpiperazin-1-ymethyl)phenyl, 2-piperidin-1-yl-5-trifluoromethylphenyl, 2-[(3-dimethylaminopropyl)methylamino]-5-trifluoromethylphenyl, 2-(3-dimethylamino-pyrroldin-1-yl)-5-trifluoromethylphenyl, 2-[methyl-(1-methylpyrrolidin-3-yl)amino]-5-trifluoromethylphenyl, biphenyl, 2-pyrrolidinyl, 1-methyl-2-pyrrolidinyl, 4-piperazinyl, 2-pyrrolyl, 1-methyl-2-pyrrolyl, 5-imidazolyl, 3-pyrazolyl, 2-pyrazinyl, 5-methyl-2-pyrazinyl, 4-pyrimidinyl, 2,6-dimethoxy-4-pyrimidinyl, 2-pyridyl, 3-pyridyl, 2-chloro-3-pyridyl, 2-chloro-5-pyridyl, 4-chloro-2-pyridyl, 4-trifluoromethyl-2-pyridyl, 4-methoxy-5-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 4,5-dichloro-3-isothiazolyl, 5-oxazolyl, 4-thiazolyl, 2-methyl-4-thiazolyl, 2,5-dimethyl-4-thiazolyl, 2-thiazolyl, 2-furanyl, 4,5-dimethyl-2-furyl, 5-methyl-2-trifluoromethyl-3-furyl, 3-furanyl, 3-thienyl, 4-methoxy-5-chloro-3-thienyl, 2-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 5-tert-butyl-isoxazol-3-yl, 5-methyl-isoxazol-3-yl, 3,5-dimethyl-isoxazol-4-yl, 5-tert-butyl-pyrazol-3-yl, and 2-methylbenzothiazol-5-yl.

The invention also relates to compounds of Formula III

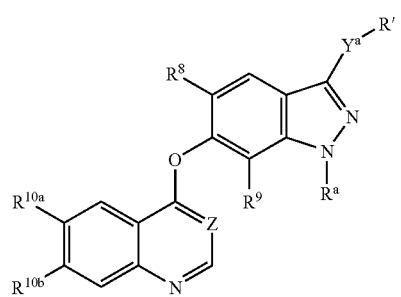

wherein $Y^a$ is selected from —NR$^z$(CH$_2$)$_p$—, —NHC(=O)(CH$_2$)$_p$—, —NHC(=O)(CH$_2$)$_p$O—, —CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—;
wherein p is 0, 1, 2, or 3;
wherein Z is CR$^x$ or N;
wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkylaminocarbonyl-$C_{1-5}$-alkyl, amino-$C_{1-5}$-alkyl, $C_{1-5}$-alkylamino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, 2,3-dihydro-1,4-benzodioxinyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, piperidinyl, 1-methyl-oxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^8$ is selected from H, fluoro, chloro and methyl;

wherein $R^9$ is selected from H, methyl and fluoro;

wherein $R^x$ is selected from H, CN, $NH_2$, F, alkylcarbonylamino, and alkylaminocarbonyl;

wherein $R^a$ is selected from H, benzyl and $C_{1-3}$ alkyl;

wherein $R^{10a}$ is H or methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

The invention also relates to compounds of wherein Z is CH; wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy.

The invention also relates to compounds of wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH($CH_3$)—, phenyl-CH($CH_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, $(CH_3)_3CCH_2$—, pentafluoroethyl, $CF_3CH_2CH_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N($CH_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl) methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ymethyl)phenyl, 2-(4-methylpiperazin-1-ymethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methyl-isothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

The invention also relates to compounds of wherein $Y^a$ is selected from —NHC(=O)—, —NH— and —NHC(=O)—NH—.

The invention also relates to compounds of wherein $Y^a$ is —NHC(=O)—, or —NHC(=O)—NH—. The invention also relates to compounds of wherein $R^8$ and $R^9$ is H.

The invention also relates to compounds of wherein $R^{10b}$ is methoxy; and pharmaceutically acceptable salts thereof.

The invention also relates to compounds of wherein $R^a$ is methyl.

The invention also relates to compounds of wherein Z is CH.

The invention also relates to compounds selected from
N-(6-((6,7-bis(methyloxy)-4-quinolinyl)oxy)-1-methyl-1H-indazol-3-yl)-4-chlorobenzamide;
N-(6-((6,7-bis(methyloxy)-4-quinolinyl)oxy)-1-methyl-1H-indazol-3-yl)-4-(trifluoromethyl)benzamide;
N-(6-((6,7-bis(methyloxy)-4-quinolinyl)oxy)-1-methyl-1H-indazol-3-yl)-4-(methyloxy)benzamide;
N-(6-((6,7-bis(methyloxy)-4-quinolinyl)oxy)-1-methyl-1H-indazol-3-yl)-3-chloro-4-fluorobenzamide;
N-(6-((6,7-bis(methyloxy)-4-quinolinyl)oxy)-1-methyl-1H-indazol-3-yl)-3,5-bis(trifluoromethyl)benzamide;
N-(6-((6,7-bis(methyloxy)-4-quinolinyl)oxy)-1-methyl-1H-indazol-3-yl)-4-chloro-2-pyridinecarboxamide;
N-(6-((6,7-bis(methyloxy)-4-quinolinyl)oxy)-1-methyl-1H-indazol-3-yl)-3-methylbenzamide;
N-(6-((6,7-bis(methyloxy)-4-quinolinyl)oxy)-1-methyl-1H-indazol-3-yl)-N'-(4-methylphenyl)urea;
N-(6-((6,7-bis(methyloxy)-4-quinolinyl)oxy)-1-methyl-1H-indazol-3-yl)-N'-phenylurea;
N-(6-((6,7-bis(methyloxy)-4-quinolinyl)oxy)-1-methyl-1H-indazol-3-yl)-3-(trifluoromethyl)benzamide; and
N-(6-((6,7-bis(methyloxy)-4-quinolinyl)oxy)-1-methyl-1H-indazol-3-yl)-N'-(4-(methyloxy)phenyl)urea.

Indications

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of this invention may also act as inhibitors of other protein kinases, e.g. tie-2, lck, src, fgf, KDR, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a sindle compound, salt and the like.

DEFINITIONS

"Angiogenesis" is defined as any alteration of an existing vascular bed or the formation of new vasculature which benefits tissue perfasion. This includes the formation of new vessels by sprouting of endothelial cells from existing blood vessels or the remodeling of existing vessels to alter size, maturity. direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—$CH_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated aromatic heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a] isoquinolyl, 3,4-dihydro-2H-benzo[1,4]oxazinyl, benzo[1,4] dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The terms "arylalkyl" and "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-III" includes any sub formulas.

The compounds of the invention are endowed with kinase inhibitory activity, such as c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of c-Met.

The present invention comprises a pharmaceutical composition comprising a therapeutically-effective amount of a compound of Formulas I-III in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I-III.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-192, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurprin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formula I-III.

Also included in the family of compounds of Formula I-III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-III. When a basic group and an acid group are present in the same molecule, a compound of Formula I-III may also form internal salts.

General Synthetic Procedures

The compounds of the invention can be synthesized according to the following procedures of Schemes 1-13, wherein the substituents are as defined for Formulas I-III, above, except where further noted.

The following abbreviations are used throughout the specification:
AcOH—acetic acid
BINAP—2,2'-bis(diphenylphosphino)-1,1'-binapthyl
BBr$_3$—boron tribromide
BH$_3$-THF—borane-tetrahydrofuran complex
BOC—t-butoxycarbonyl
BSA—bovine serum albumin
n-BuLi—n-butyl lithium
CO—carbon monoxide
C$_2$O$_2$Cl$_2$ or (COCl)$_2$—oxalyl chloride
Cs$_2$CO$_3$—cesium carbonate
CHCl$_3$—chloroform
Et$_2$O—diethyl ether
DCM, CH$_2$Cl$_2$—methylene chloride
DIBAL—diisobutylaluminum hydride
DIEA, DIPEA, Hunig's base—diisopropylethylamine
DMF—dimethylformamide
dppa—diphenylphosphoryl azide
DPPP—1,3-diphenylphosphino propane
DMAP—4-dimethylaminopyridine
EtOAc, EA—ethyl acetate
EtOH—ethanol
Et$_2$O—diethyl ether
EDC, EDCI—1-(3-dimethylaminopropyl)-3-ethylcarbodiimide hydrochloride
EtNH$_2$—ethyl amine
FBS—fetal bovine serum
g—gram
h—hour
HCl—hydrochloric acid
HOAt—1-hydroxy-7-azabenzotriazole
HOBt—1-hydroxybenzotriazole hydrate
H$_2$—hydrogen
H$_2$—hydrogen
H$_2$0—water
H$_2$O$_2$—hydrogen peroxide
HATU—O-(7-azabenzotriazol-1-yl-)N,N,N',N', tetramethyluronium hexafluorophosphate
KOH—potassium hydroxide
K$_2$CO$_3$—potassium carbonate
K$_3$PO$_4$—potassium phosphate
KMnO$_4$—potassium permanganate
LAH—lithium aluminum hydride
LiHMDS—lithium bis(trimethylsilyl)-amide
LiOH—lithium hydroxide
MgSO$_4$—magnesium sulfate
MCPBA—meta-chloroperbenzoic acid
MeOH, CH$_3$OH—methanol MeNH$_2$—methyl amine
NH$_4$Cl—ammonium chloride
NH$_4$OH—ammonium hydroxide
NMP—N-methylpyrrolidinone
NaHCO$_3$—sodium bicarbonate
NaN$_3$—sodium azide
Na$_2$SO—sodium sulfate
NaOH—sodium hydroxide
NaH—sodium hydride
Na$_2$SO$_4$—sodium sulfate
NaOt-Bu—sodium tert-butoxide
NaHB(OAc)$_3$—sodium triacetoxyborohydride
N$_2$—nitrogen
O/N—overnight
POCl$_3$—phosphorus oxychloride
Pd/C—palladium on carbon
Pd$_2$(dba)$_3$—bis(dibenzylideneacetone) palladium
Pd(OAC)$_2$—palladium (II) acetate
P(t-bu)$_3$—tri(tert-butyl)phosphine
PBS—phospate buffered saline
PyBop—Benzotriazol-1-yl-oxy-tripyrrolidino-phosphonium hexafluorophosphate
RT—room temperature
SOCl$_2$—thionyl chloride
TBTU—O-benzotriazol-1-yl-N,N,N',N'-tetramethyluronium tetrafluoroborate
TBAI—tetrabutylammonium iodide
TFA—trifluoroacetic acid
THF—tetrahydrofuran
TEA, Et$_3$N—triethylamine

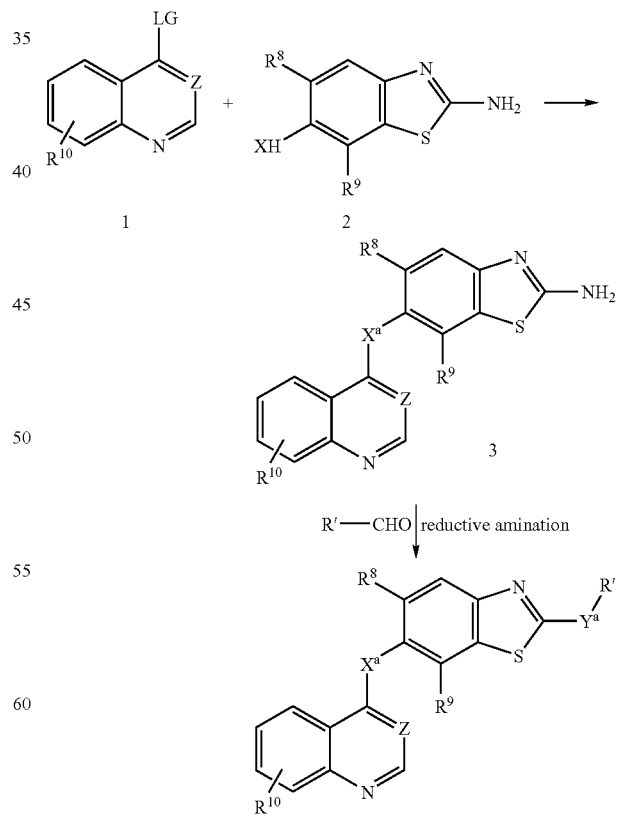

Scheme 1

Substituted bicyclic compounds 4 [where $Y^a$ is substituted amines or amides] can be prepared by the process outlined in Scheme 1. The amine 2 [where X is O] is coupled with a quinoline derivative 1 [where LG is halo, and the like] such as in the presence of KOH and Cu, in a solvent such as dry $CH_2Cl_2$ at a temperature above RT, preferably above about 70° C., more preferably at a temperature of about 100° C., to form the linked compound 3. Such heating is preferably heated by microwave. The amine 3 can be reductively aminated with aldehydes, such as in the presence of NaBH(OAc)$_3$, in a solvent such as dry $CH_2Cl_2$ at a temperature at about RT, to form amides 4 of the present invention.

Alternatively, the amine 3 can be coupled with compounds having an active acyl moiety, such as acid chlorides and carboxylic acids, such as in the presence of PyBOP and a base such as $K_2CO_3$, to form amides 4 of the present invention.

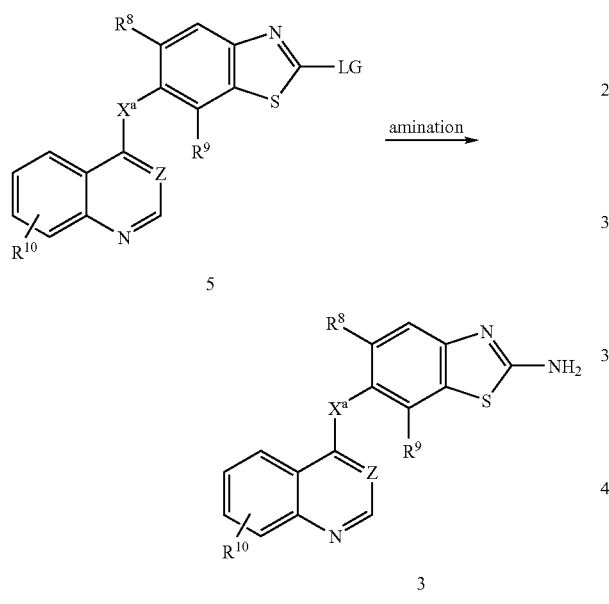

Scheme 2

Alternatively, amines 3 can be prepared via amination of a bromo-derivative 5 e.g. a halo derivative more preferably a bromo-derivative such as in the presence of Pd and a strong base, e.g. LiHMDS. Preferably Pd$_2$(dba)$_3$ in the presence of P(t-Bu)$_3$ is used. Preferably the reaction is kept at about RT.

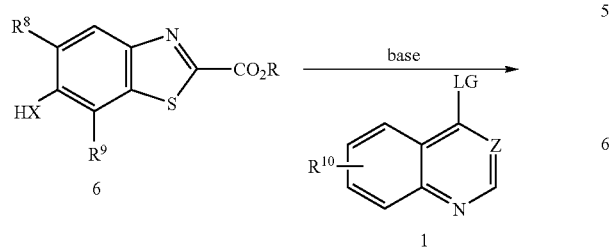

Scheme 3

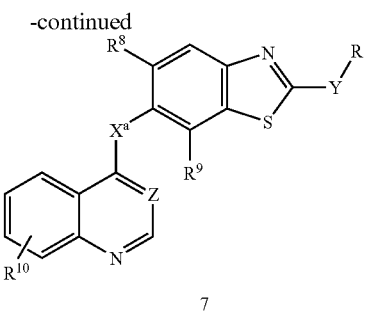

Alternatively, compounds where Y is —CO$_2$— 6 can be prepared as described in Scheme 3. A substituted carboxylic acid ester 6 is treated with strong base, such as NaH, preferably in a solvent such as DMF, to form the anion. Preferably the reaction temperature is at about RT. Substituted nitrogen containing heteroaryl compounds 1, such as substituted quinazolines or quinolines, are coupled to the anion to form the compounds of the present invention 7. The reaction temperature is above RT, preferably above about 50° C., more preferably at about 60° C.

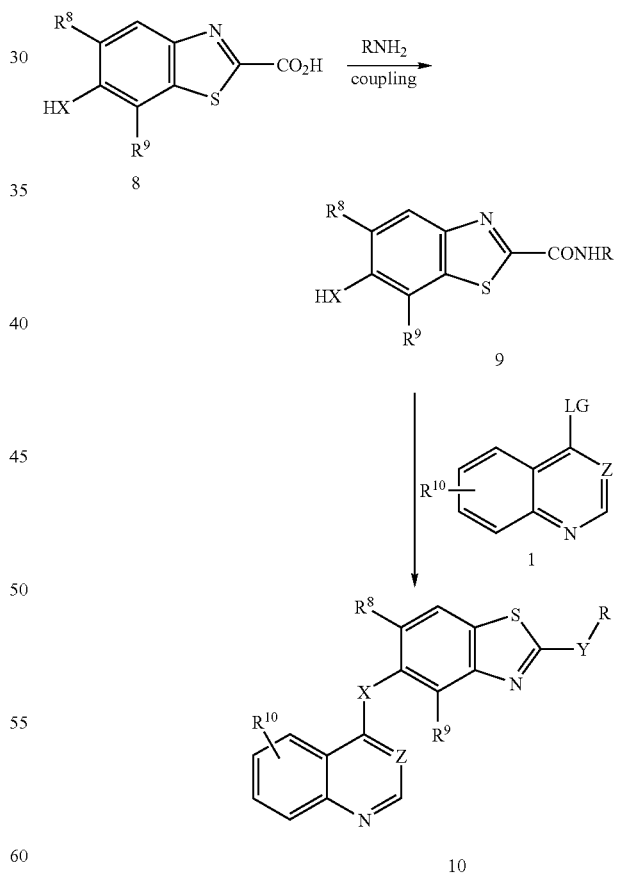

Scheme 4

Alternatively, compounds where Y is —C(=O)NH— 10 can be prepared as described in Scheme 4. A substituted carboxylic acid 8 can be coupled with an amine under standard coupling chemistry, such as with EDC in the presence of a solvent like DMF, to form amides 9. The reaction temperature is preferably kept at about RT. Coupling the amides 9 with nitrogen-containing heterocyclic compounds, such as quinolines and quinazolines 1, by the method described above in Scheme 1 provides compounds of the present invention 10 [where Y is —C(=O)NH—].

Scheme 5

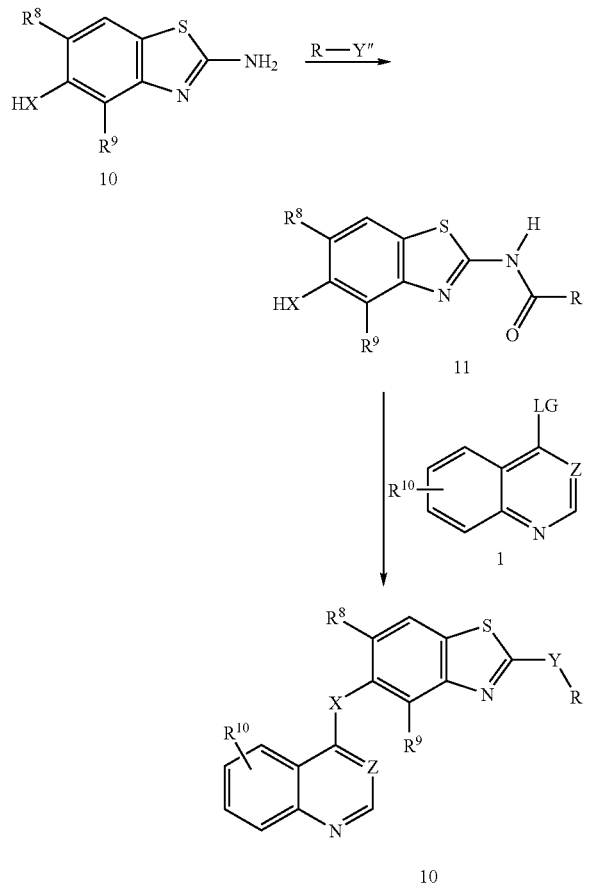

Alternatively, compounds where Y is —C(=O)NH— 10 can be prepared as described in Scheme 5. A substituted amine 11 can be coupled with an active carbonyl compound (Y"—R) as described in Scheme 1, to form amides 12. Coupling the amides 12 with nitrogen containing heterocyclic compounds, such as quinolines and quinazolines 1 by the method described in Scheme 4, provides compounds of the present invention 10 [where Y is —NHC(=O)—].

Scheme 6

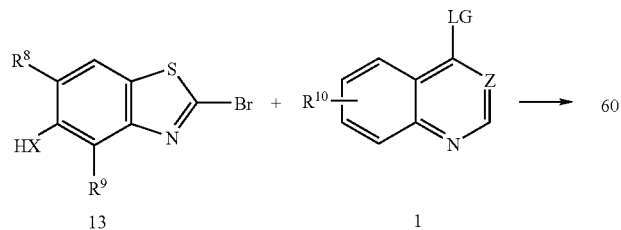

-continued

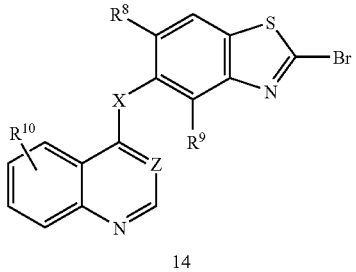

Bromonaphthyl intermediates 14 can be provided by the method described in Scheme 6. A mixture of substituted quinoline 1 [where LG is chloro], 6 bromo compound 13 and DMAP, in a solvent such as toluene, at a temperature above RT, preferably above about 100° C., more preferably at a temperature of about 180° C., to form the intermediates 14.

Scheme 7

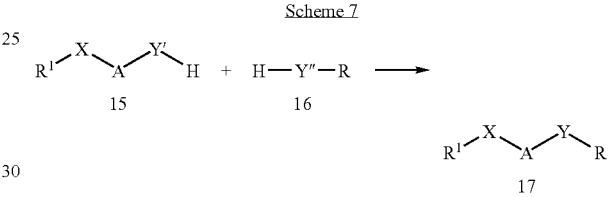

Substituted bicyclic compounds can be prepared by the process outlined in Scheme 7. Coupling of bicyclic compounds (where R is not H) 16 with intermediates 15 (where Y' is a portion of Y, such as NH, C(=O), etc.) yields compounds 17.

Scheme 8

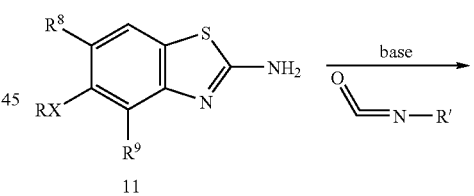

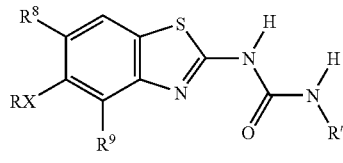

Ureas of the present invention 18 are prepared by the method outlined in Scheme 8. Amines 11 are treated with isocyantates, preferably an excess of isocyanate, in the presence of base, preferably an excess of base, in a solvent such as DMF to form the ureas 18. Preferably the reaction temperature is maintained at around RT.

Scheme 9

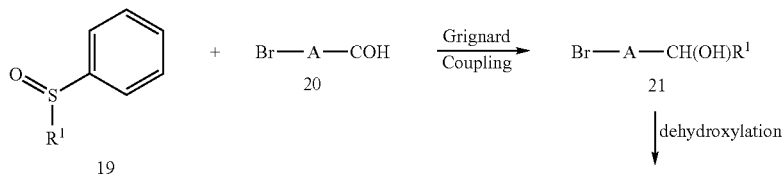

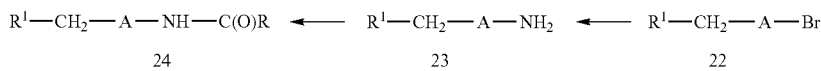

Substituted bicyclic compounds 24 [where Y is an amide] can be prepared by the process outlined in Scheme 9. 6-Bromo-2-hydroxymethyl compounds 21 are prepared such as by the coupling of 6-carbaldehydes 20 and activated $R^1$ containing compounds 19, such as phenylsulfinyl substituted compounds. Preferably the coupling occurs in the presence of a Grignard reagent, such as phenylmagnesium bromide, in an appropriate protic solvent such as THF. The temperature is preferably maintained at about RT. Preferably the Grignard is first added to the $R^1$ containing compound 19 prior to the addition of the carbaldehyde 20. The resulting hydroxymethyl compound 21 is dehydroxylated, such as in the presence of Zn and formic acid. The dehydroxylation preferably occurs at a temperature above RT, more preferably above about 50° C., and most preferably at about reflux temperature. The resulting 6-bromonaphtyl compound 22 is animated similar to that described in Scheme 2 to form naphthyl amine 23 and the amides 24 are consequently formed similar to that described in Scheme 1.

Scheme 10

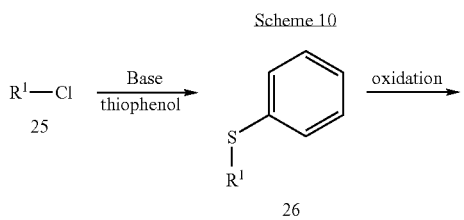

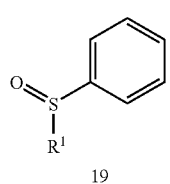

Activated $R^1$ containing compounds 19 can be prepared such as by the method identified in Scheme 10. Halosubstituted compounds 25 are dehalogenated, such as with aqueous base, e.g. KOH, then treated with a thiol compound, such as thiophenol, at a temperature above RT, preferably above 75° C., more preferably at about 100° C. The thio compound 26 is oxidized, such as with mCPBA, at a temperature below RT, preferably below –23° C., more preferably at about –78° C., to form the sulfinyl compounds 19.

Scheme 11

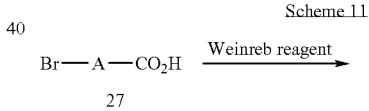

6-Bromonaphthyl-2-carbaldehydes 20 are prepared from the carboxylic acid 27 via reduction of the amide intermediate 28. The amide 28 is formed via peptide type coupling, such as in the presence of EDC, HOBt and base, of a substituted hydroxylamine, at a temperature preferably at about RT. Reduction of the amide 28, such as with DIBAL, in a solvent such as THF, at a temperature between –78° C. and RT, preferably at about RT, provides the desired 6-bromonaphthalene-2-carbaldehyde 20.

Other benzothiazoles and benzoxazoles can be prepared by methods described in the literature (e.g. J. Heterocycl. Chem., 17(4):817 (1980); Tetrahedron, 42(20):5739 (1986); and Chem. Pharm. Bull., 43(10):1614 (1995)).

Scheme 12

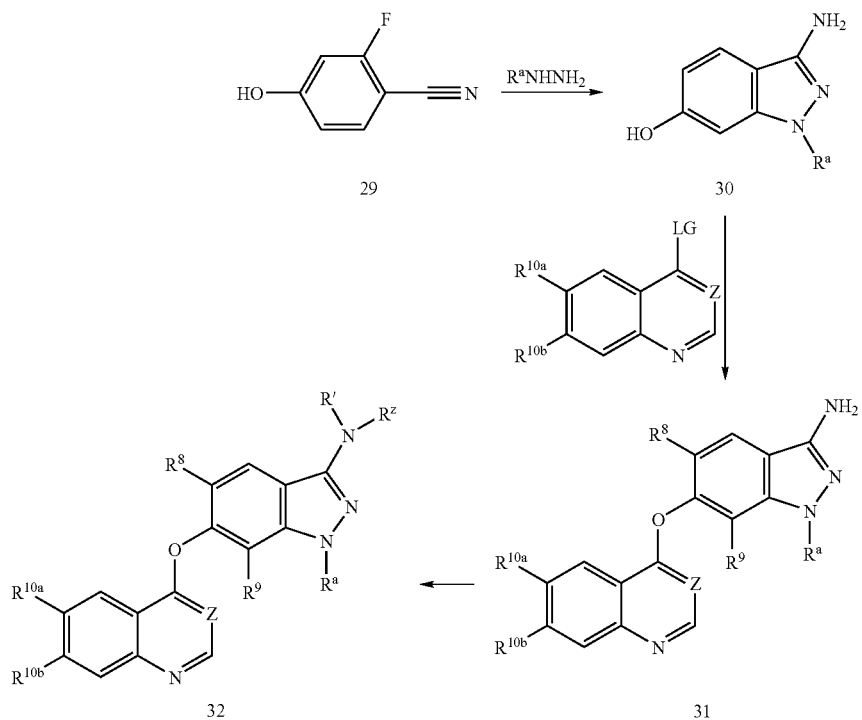

Alternatively, compounds (where A is indazoles) can be prepared as described in Scheme 12. A solution of 6-fluoro-4-hydroxy benzonitrile is reacted with a hydrazine, such as methyl hydrazine at a temperature above RT, preferably above about 50° C. and more preferably at about 80° C., to provide the 1H-indazol-6-ol 30. The alcohol 30 is coupled with the appropriately substituted quinolines or quinazolines (where LG is halo, and the like) in the presence of a base such as cesium carbonate, to form the ethers 31. The reaction temperature is above RT, preferably above about 50° C., more preferably at about 100° C. Other compounds of the invention 32 can be prepared by substituting the amine 31 using chemistry such as reductive amination of aldehydes such as using NaBH(OAc)$_3$ at a temperature of about RT.

Alternatively a solution/suspension of Pd$_2$dba$_3$, 2-(dicyclohexylphosphino)-2'-4'-6'-tri-i-propyl-1,1'-biphenyl, a base such as sodium tert-butoxide, the 1H-indazol-3-amine 31 and a halo compound, such as an aryl halide, in a solvent such as toluene can be used to form substituted amines 32. The reaction temperature is above RT, preferably above about 50° C., more preferably at about 100° C.

Alternatively, a solution of 1H-indazol-3-amine 31 in a solvent such as pyridine, is treated with an substituted acid chloride such as p-anisoyl chloride to form the substituted amides 32. The reaction is preferably maintained at a temperature of about RT.

Alternatively, a solution of 1H-indazol-3-amine in a solvent such as benzene is treated with a substituted isocyanate to form the substituted ureas 32. The reaction is preferably maintained at a temperature of about RT.

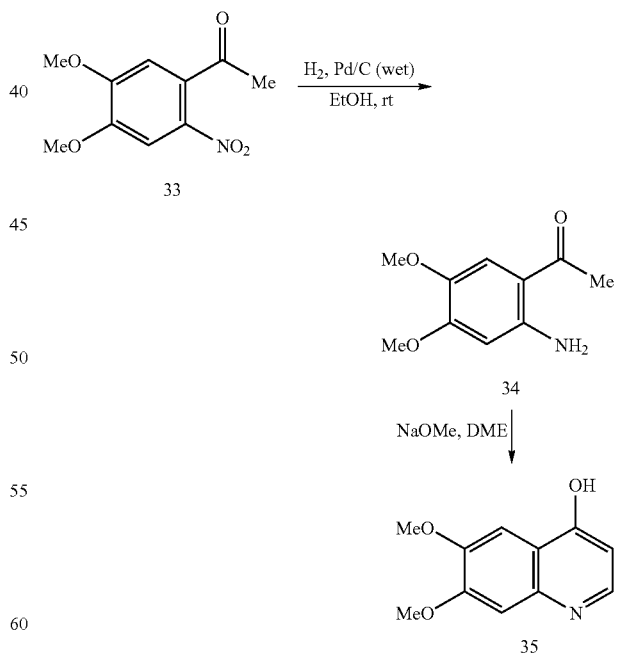

Dimethoxy-quinolines 35 can be prepared from the corresponding nitro 33 compounds via the method described in Scheme 13. Reduction of the nitro compound 33 to the amine 34, such as with H$_2$ in the presence of a catalyst, such as Pd, e.g. Pd/C, followed by treatment with base and dimethyl ether, yields the desired quinolines 35.

Various substituted quinolines and quinazolines can be prepared by the methods described in WO 98/13350.

The starting compounds defined in Schemes 1-13 may also be present with functional groups in protected form if necessary and/or in the form of salts, provided a salt-forming group is present and the reaction in salt form is possible. If so desired, one compound of Formula I can be converted into another compound of Formula I or a N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of Formula I with $H_2O_2$, Oxone, or a peracid, e.g. mCPBA, in an inert solvent, e.g. $CH_2Cl_2$, or a mixture of water and an alcohol such as MeOH or EtOH, at a temperature between about −10-35° C., such as about 0° C.—RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides", Volume 3, editors: E. Gross and J. Meienhofer, Academic Press, London and New York (1981), in "Methoden der organischen Chemie" (Methods of Organic Chemistry), Houben Weyl, $4^{th}$ edition, Volume 15/1, Georg Thieme Verlag, Stuttgart (1974), in H.-D. Jakubke and H. Jescheit, "Aminosäuren, Peptide, Proteine" (Amino Acids, Peptides, Proteins), Verlag Chemie, Weinheim, Deerfield Beach, and Basel (1982), and in Jochen Lehmann, "Chemie der Kohlenhydrate: Monosaccharide und Derivate" (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example, a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., EtOAc, ethers, typically aliphatic ethers, e.g., $Et_2O$, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

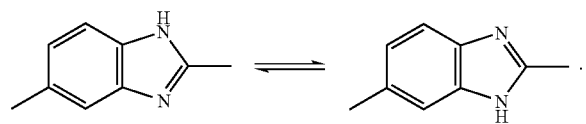

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, "Comprehensive Organic Transformations", VCH Publishers (1989); T. W. Greene and P. G. M. Wuts, "Protective Groups in Organic Synthesis", $3^{rd}$ edition, John Wiley and Sons (1999); L. Fieser and M. Fieser, "Fieser and Fieser's Reagents for Organic Synthesis", John Wiley and Sons (1994); A. Katritzky and A. Pozharski, "Handbook of Heterocyclic Chemistry", $2^{nd}$ edition (2001); M. Bodanszky, A. Bodanszky, "The Practice of Peptide Synthesis", Springer-Verlag, Berlin Heidelberg (1984); J. Seyden-Penne, "Reductions by the Alumino- and Borohydrides in Organic Synthesis", $2^{nd}$ edition, Wiley-VCH, (1997); and L. Paquette, editor, "Encyclopedia of Reagents for Organic Synthesis", John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification.

Anhydrous solvents such as DMF, THF, CH$_2$Cl$_2$ and toluene were obtained from the Aldrich Chemical Company.

Example 1

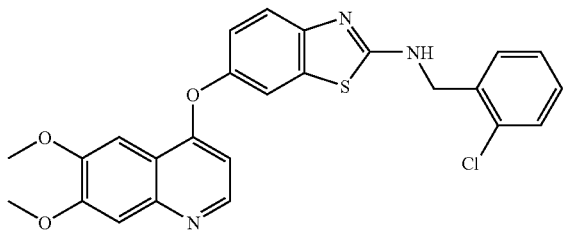

(2-Chlorobenzyl)-[6-(6,7-dimethoxy-quinolin-4-yloxy)-benzothiazol-2-yl-amine (a) 6-(6,7-Dimethoxy-quinolin-4-yloxy)-benzothiazol-2-ylamine. To a microwave vial was added 4-chloro-6,7-dimethoxy-quinoline prepared by the method of Miwa, et al., (WO 03/33472) (0.300 g, 1.3 mmol), 2-amino-benzothiazol-6-ol (0.334 g, 2.0 mmol) and KOH pellets (0.140 g, 2.6 mmol), followed by 4% by weight of Cu powder in 3 mL of dry CH$_2$Cl$_2$. The sealed vial was microwaved for 10 min at 100° C. and 60 W. (Powermax, CEM). The mixture was diluted with CH$_2$Cl$_2$ and transferred to a separation funnel. NaOH (40 mL) was added and the organic layer was extracted 3× with CH$_2$Cl$_2$. The organics were combined, dried over Na$_2$SO$_4$, filtered, and concentrated in-vacuo. The crude compound was purified by crystallization from 10% CH$_2$Cl$_2$/Hexanes to give the titled compound as a light purple powder. MS (ESI pos. ion) m/z: 354 (M+H). Calc'd Exact Mass for C$_{18}$H$_{15}$N$_3$O$_3$S: 353.08.

(b) (2-Chloro-benzyl)-[6-(6,7-dimethoxy-quinolin-4-yloxy)-benzothiazol-2-yl-amine. To a mixture of 6-(6,7-dimethoxy-quinolin-4-yloxy)-benzothiazol-2-ylamine (0.100 g, 0.28 mmol, Step a) in dry CH$_2$Cl$_2$ was added 2-chloro-benzaldehyde (1.5 mL, 0.4 mmol). The mixture was stirred for 10 min. NaBH(OAc)$_3$ (0.200 g, 0.8 mmol) was added and the mixture was stirred overnight at RT under an inert atmosphere. The mixture was quenched with water, diluted with CH$_2$Cl$_2$ and poured into a seperatory funnel. The organics were collected, dried over Na$_2$SO$_4$, filtered, and concentrated in-vacuo. The crude was purified by silica gel column chromatography (MeOH/CH$_2$Cl$_2$) to give the product as a light yellow solid. MS (ESI pos. ion) m/z: 479 (M+H). Calc'd Exact Mass for C$_{25}$H$_{20}$ClN$_3$O$_3$S: 477.09.

Example 2

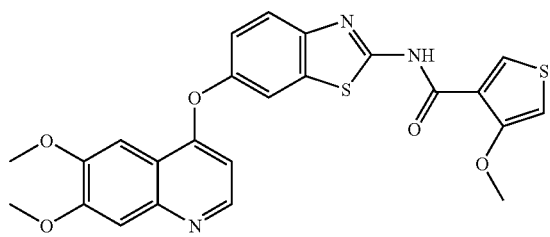

4-Methoxy-thiophene-3-carboxylic acid [6-(6,7-dimethoxy-quinolin-4-yloxy)-benzothiazol-2-yl]-amide To a mixture of 6-(6,7-dimethoxy-quinolin-4-yloxy)-benzothiazol-2-ylamine (0.100 g, 0.28 mmol (Example 1, Step a) in dry CH$_2$Cl$_2$ was added 4-methoxy-thiophene-3-carboxylic acid (0.063 g, 0.3 mmol), PyBOP (0.437 g, 1.2 mmol), and K$_2$CO$_3$ (0.116 g, 1.2 mmol). The mixture was stirred at RT overnight under an inert atmosphere. The mixture was quenched with water and diluted with CH$_2$Cl$_2$ and transferred to a separation funnel. The organics were collected, dried over Na$_2$SO$_4$, filtered, and concentrated in-vacuo. The crude was purified by silica gel column chromatography (MeOH/CH$_2$Cl$_2$) to give the product as a rust colored solid. MS (ESI pos. ion) m/z: 494 (M+H). Calc'd Exact Mass for C$_{24}$H$_{19}$N$_3$O$_5$S$_2$: 493.08.

Example 3

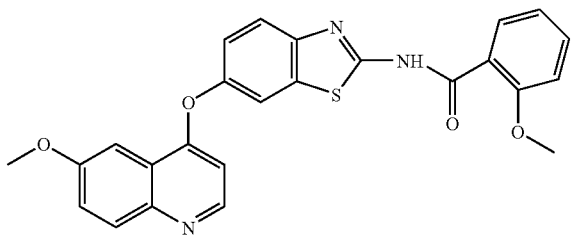

2-Methoxy-N-[6-(6-methoxy-quinolin-4-yloxy)-benzothiazol-2-yl]-benzamide (a) Preparation of 6-(6-Methoxy-quinolin-4-yloxy)-benzothiazol-2-ylamine. The title compound prepared according to Example 1, Step a, with 4-chloro-6-methoxy-quinoline prepared via the procedure of Krogstad et al (J. Med. Chem., 41:4918-4926 (1998)).

(b) Preparation of 2-Methoxy-N-[6-(6-methoxy-quinolin-4-yloxy)-benzothiazol-2-yl]-benzamide. The title compound was prepared from 6-(6-methoxy-quinolin-4-yloxy)-benzothiazol-2-ylamine according to a procedure similar to that described for Example 2.

The following Examples were prepared similar to that described in Example 2.

| Ex. No. | Structure & Name | Mol Formula | Mass | M + H |
|---|---|---|---|---|
| 4 | 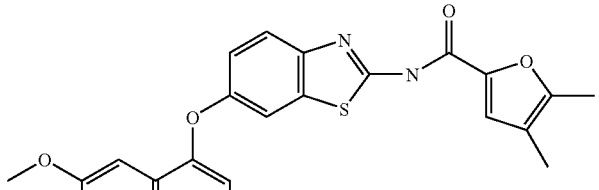<br>4,5-Dimethyl-furan-2-carboxylic acid [6-(6,7-dimethoxy-quinolin-4-yloxy)-benzothiazol-2-yl]-amide | $C_{25}H_{21}N_3O_5S$ | 475.12 | 475 |
| 5 | 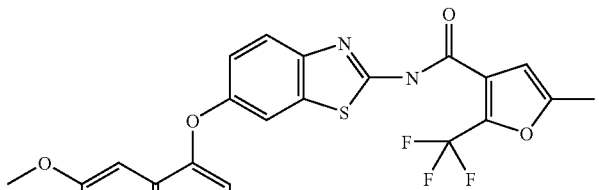<br>5-Methyl-2-trifluoromethyl-furan-3-carboxylic acid [6-(6,7-dimethoxy-quinolin-4-yloxy)-benzothiazol-2-yl]-amide | $C_{25}H_{18}F_3N_3O_5S$ | 529.09 | 529 |
| 6 | 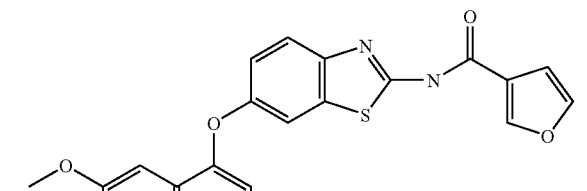<br>Furan-3-carboxylic acid [6-(6,7-dimethoxy-quinolin-4-yloxy)-benzothiazol-2-yl]-amide | $C_{23}H_{17}N_3O_5S$ | 447.09 | 447 |
| 7 | 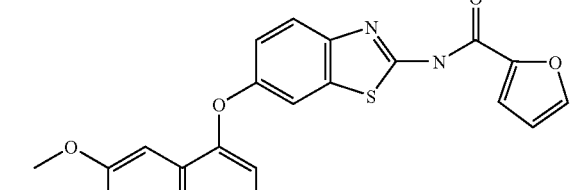<br>Furan-2-carboxylic acid [6-(6,7-dimethoxy-quinolin-4-yloxy)-benzothiazol-2-yl]-amide | $C_{23}H_{17}N_3O_5S$ | 447.09 | 447 |
| 8 | 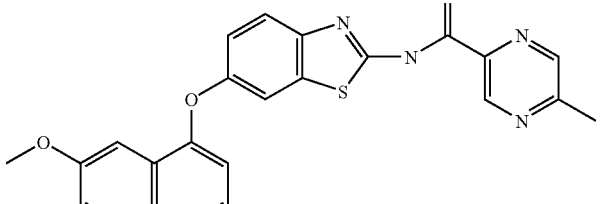<br>5-Methyl-pyrazine-2-carboxylic acid [6-(6,7-dimethoxy-quinolin-4-yloxy)-benzothiazol-2-yl]-amide | $C_{24}H_{19}N_5O_4S$ | 473.12 | 473 |

| Ex. No. | Structure & Name | Mol Formula | Mass | M + H |
|---|---|---|---|---|
| 9 | 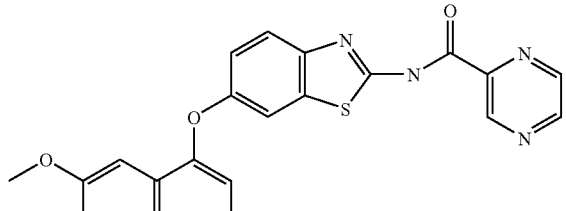<br>Pyrazine-2-carboxylic acid [6-(6,7-dimethoxy-quinolin-4-yloxy)-benzothiazol-2-yl]-amide | $C_{23}H_{17}N_5O_4S$ | 459.10 | 459 |
| 10 | 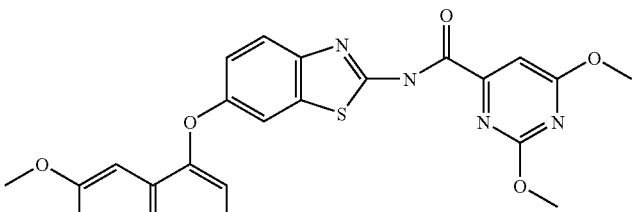<br>2,6-Dimethoxy-pyrimidine-4-carboxylic acid [6-(6,7-dimethoxy-quinolin-4-yloxy)-benzothiazol-2-yl]-amide | $C_{23}H_{21}N_5O_6S$ | 519.12 | 519 |
| 11 | 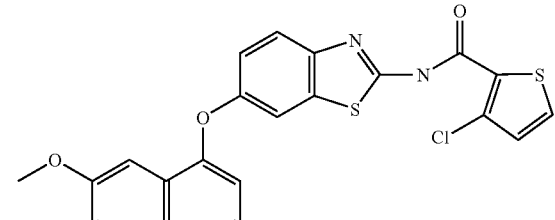<br>3-Chloro-thiophene-2-carboxylic acid [6-(6,7-dimethoxy-quinolin-4-yloxy)-benzothiazol-2-yl]-amide | $C_{23}H_{16}ClN_3O_4S_2$ | 497.03 | 497 |
| 12 | 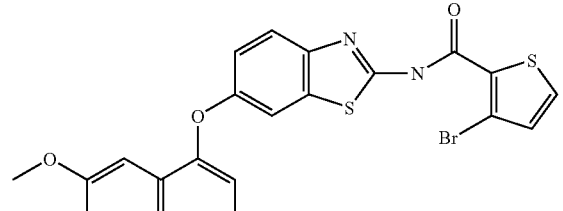<br>3-Bromo-thiophene-2-carboxylic acid [6-(6,7-dimethoxy-quinolin-4-yloxy)-benzothiazol-2-yl]-amide | $C_{23}H_{16}BrN_3O_4S_2$ | 540.98 | 542 |
| 13 | 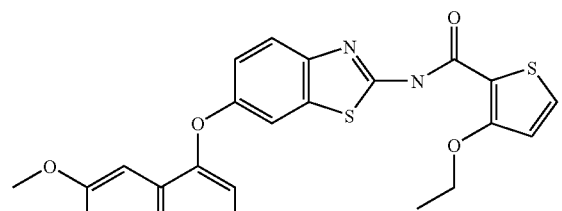<br>3-Ethoxy-thiophene-2-carboxylic acid [6-(6,7-dimethoxy-quinolin-4-yloxy)-benzothiazol-2-yl]-amide | $C_{25}H_{21}N_3O_5S_2$ | 507.09 | 507 |

-continued

| Ex. No. | Structure & Name | Mol Formula | Mass | M + H |
|---|---|---|---|---|
| 14 | 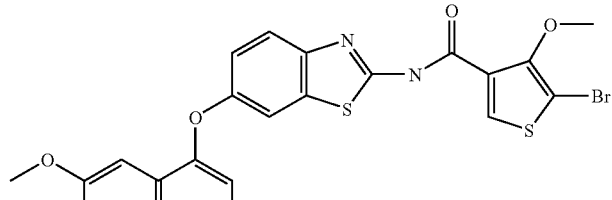<br>5-Bromo-4-methoxy-thiophene-3-carboxylic acid [6-(6,7-dimethoxy-quinolin-4-yloxy)-benzothiazol-2-yl]-amide | $C_{24}H_{18}BrN_3O_5S_2$ | 570.99 | 572 |
| 15 | 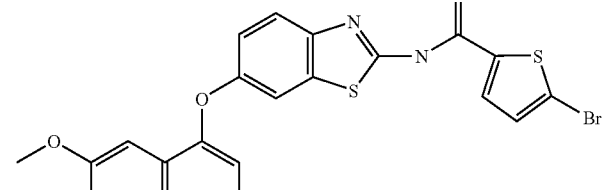<br>5-Bromo-thiophene-2-carboxylic acid [6-(6,7-dimethoxy-quinolin-4-yloxy)-benzothiazol-2-yl]-amide | $C_{23}H_{16}BrN_3O_4S_2$ | 540.98 | 542 |
| 16 | 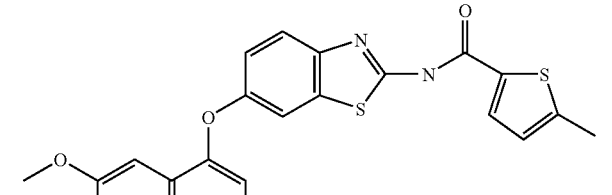<br>5-Methyl-thiophene-2-carboxylic acid [6-(6,7-dimethoxy-quinolin-4-yloxy)-benzothiazol-2-yl]-amide | $C_{24}H_{19}N_3O_4S_2$ | 477.08 | 477 |
| 17 | 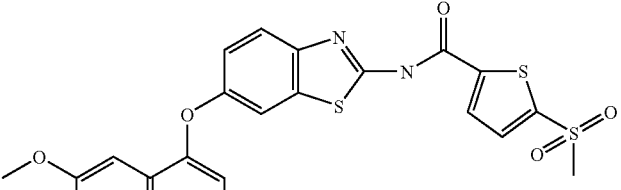<br>5-Methane sulfonyl-thiophene-2-carboxylic acid [6-(6,7-dimethoxy-quinolin-4-yloxy)-benzothiazol-2-yl]-amide | $C_{24}H_{19}N_3O_6S_2$ | 541.04 | 541 |
| 18 | 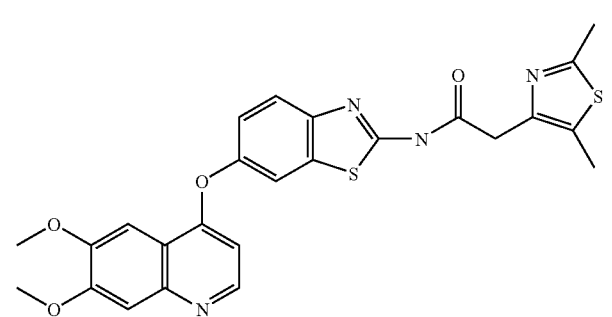 | $C_{25}H_{22}N_4O_4S_2$ | 506.605 | 506 |

| Ex. No. | Structure & Name | Mol Formula | Mass | M + H |
|---|---|---|---|---|
| | N-[6-(6,7-Dimethoxy-quinolin-4-yloxy)-benzothiazol-2-yl]-2-(2,5-dimethyl-thiazol-4-yl)-acetamide | | | |
| 19 | 5-Methylsulfanyl-thiophene-2-carboxylic acid [6-(6,7-dimethoxy-quinolin-4-yloxy)-benzothiazol-2-yl]-amide | $C_{24}H_{19}N_3O_4S_2$ | 509.629 | 509 |
| 20 | 3,5-Dimethyl-isoxazole-4-carboxylic acid [6-(6,7-dimethoxy-quinolin-4-yloxy)-benzothiazol-2-yl]-amide | $C_{24}H_{20}N_4O_5S$ | 476.511 | 476 |
| 21 | 5-Methyl-isoxazole-3-carboxylic acid [6-(6,7-dimethoxy-quinolin-4-yloxy)-benzothiazol-2-yl]-amide | $C_{23}H_{18}N_4O_5S$ | 462.484 | 462 |
| 22 | 4,5-Dichloro-isothiazole-3-carboxylic acid [6-(6,7-dimethoxy-quinolin-4-yloxy)-benzothiazol-2-yl]-amide | $C_{22}H_{14}Cl_2N_4O_4S_2$ | 533.415 | 533 |
| 23 | | $C_{22}H_{16}N_4O_5S$ | 448.457 | 448 |

-continued

| Ex. No. | Structure & Name | Mol Formula | Mass | M + H |
|---|---|---|---|---|
| | Oxazole-5-carboxylic acid [6-(6,7-dimethoxy-quinolin-4-yloxy)-benzothiazol-2-yl]-amide | | | |
| 24 | 2,4-Dimethyl-thiazole-5-carboxylic acid [6-(6,7-dimethoxy-quinolin-4-yloxy)-benzothiazol-2-yl]-amide | $C_{24}H_{20}N_4O_4S_2$ | 492.578 | 492 |
| 25 | 2-Methyl-thiazole-4-carboxylic acid [6-(6,7-dimethoxy-quinolin-4-yloxy)-benzothiazol-2-yl]-amide | $C_{23}H_{18}N_4O_4S$ | 478.551 | 478 |
| 26 | 2-Methoxy-N-[6-(7-methoxy-quinolin-4-yloxy)-benzothiazol-2-yl]-benzamide | $C_{25}H_{19}N_3O_4S$ | 457.508 | 458 (M = 1) |
| 27 | 1-Methyl-pyrrolidine-2-carboxylic acid [6-(6,7-dimethoxy-quinolin-4-yloxy)-benzothiazol-2-yl]-amide | $C_{24}H_{18}ClN_3O_5S$ | 528.007 | 464 |
| 28 | | $C_{23}H_{16}ClN_3O_4S_2$ | 497.981 | 497.5 |

-continued

| Ex. No. | Structure & Name | Mol Formula | Mass | M + H |
|---|---|---|---|---|
| | 5-Chloro-thiophene-2-carboxylic acid [6-(6,7-dimethoxy-quinolin-4-yloxy)-benzothiazol-2-yl]-amide | | | |
| 29 | 3-Methyl-thiophene-2-carboxylic acid [6-(6,7-dimethoxy-quinolin-4-yloxy)-benzothiazol-2-yl]-amide | $C_{24}H_{19}N_3O_4S_2$ | 477.563 | 477 |
| 30 | 1-Methyl-1H-pyrrole-2-carboxylic acid [6-(6,7-dimethoxy-quinolin-4-yloxy)-benzothiazol-2-yl]-amide | $C_{24}H_{20}N_4O_4S$ | 460.512 | 460 |
| 31 | 2-Chloro-N-[6-(6,7-dimethoxy-quinolin-4-yloxy)-benzothiazol-2-yl]-nicotinamide | $C_{24}H_{17}ClN_4O_4S$ | 492.941 | 492.5 |
| 32 | 6-Chloro-N-[6-(6,7-dimethoxy-quinolin-4-yloxy)-benzothiazol-2-yl]-nicotinamide | $C_{24}H_{17}ClN_4O_4S$ | 492.941 | 492.5 |
| 33 | | $C_{24}H_{17}ClN_4O_4S$ | 492.941 | 492.5 |

-continued

| Ex. No. | Structure & Name | Mol Formula | Mass | M + H |
|---|---|---|---|---|
| | 2-Chloro-N-[6-(6,7-dimethoxy-quinolin-4-yloxy)-benzothiazol-2-yl]-isonicotinamide | | | |
| 34 | N-[6-(6,7-Dimethoxy-quinolin-4-yloxy)-benzothiazol-2-yl]-nicotinamide | $C_{24}H_{18}N_4O_4S$ | 458.496 | 458 |
| 35 | N-[6-(6,7-Dimethoxy-quinolin-4-yloxy)-benzothiazol-2-yl]-4-methyl-benzamide | $C_{26}H_{21}N_3O_4S$ | 471.535 | 471 |
| 36 | N-[6-(6,7-Dimethoxy-quinolin-4-yloxy)-benzothiazol-2-yl]-3-methyl-benzamide | $C_{26}H_{21}N_3O_4S$ | 471.535 | 471 |
| 37 | N-[6-(6,7-Dimethoxy-quinolin-4-yloxy)-benzothiazol-2-yl]-2-methyl-benzamide | $C_{26}H_{21}N_3O_4S$ | 471.535 | 471 |
| 38 | | $C_{29}H_{27}N_3O_4S$ | 513.615 | 513 |

| Ex. No. | Structure & Name | Mol Formula | Mass | M + H |
|---|---|---|---|---|
| | 4-tert-Butyl-N-[6-(6,7-dimethoxy-quinolin-4-yloxy)-benzothiazol-2-yl]-benzamide | | | |
| 39 | N-[6-(6,7-Dimethoxy-quinolin-4-yloxy)-benzothiazol-2-yl]-4-trifluoromethyl-benzamide | $C_{26}H_{18}F_3N_3O_4S$ | 525.505 | 525 |
| 40 | N-[6-(6,7-Dimethoxy-quinolin-4-yloxy)-benzothiazol-2-yl]-2-trifluoromethyl-benzamide | $C_{26}H_{18}F_3N_3O_4S$ | 525.505 | 525 |
| 41 | 2-Chloro-N-[6-(6,7-dimethoxy-quinolin-4-yloxy)-benzothiazol-2-yl]-benzamide | $C_{25}H_{18}ClN_3O_4S$ | 491.953 | 491.5 |
| 42 | N-[6-(6,7-Dimethoxy-quinolin-4-yloxy)-benzothiazol-2-yl]-3-fluoro-benzamide | $C_{25}H_{18}FN_3O_4S$ | 475.498 | 475 |
| 43 | | $C_{25}H_{18}FN_3O_4S$ | 475.498 | 475 |

| Ex. No. | Structure & Name | Mol Formula | Mass | M + H |
|---|---|---|---|---|
| | N-[6-(6,7-Dimethoxy-quinolin-4-yloxy)-benzothiazol-2-yl]-2-fluoro-benzamide | | | |
| 44 | 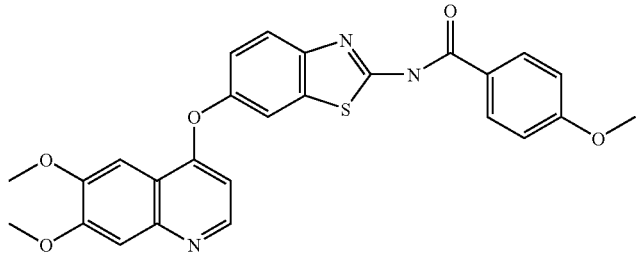<br>N-[6-(6,7-Dimethoxy-quinolin-4-yloxy)-benzothiazol-2-yl]-4-methoxy-benzamide | $C_{26}H_{21}N_3O_5S$ | 487.534 | 487 |
| 45 | 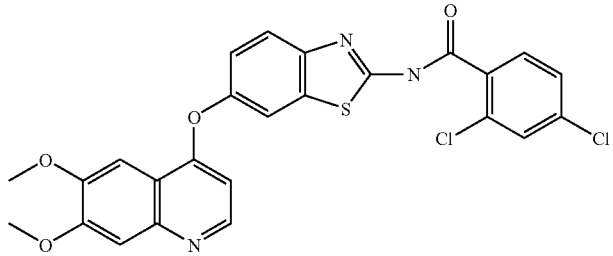<br>2,4-Dichloro-N-[6-(6,7-dimethoxy-quinolin-4-yloxy)-benzothiazol-2-yl]-benzamide | $C_{25}H_{17}Cl_2N_3O_4S$ | 526.398 | 526 |
| 46 | 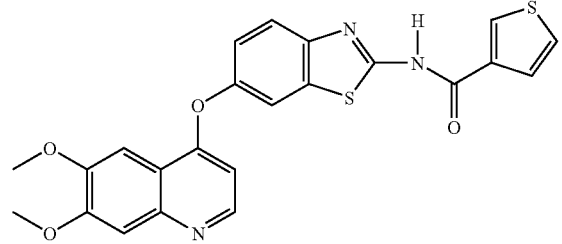<br>Thiophene-3-carboxylic acid [6-(6,7-dimethoxy-quinolin-4-yloxy)-benzothiazol-2-yl]-amide | $C_{23}H_{17}N_3O_4S_2$ | 463.536 | 463 |
| 47 | 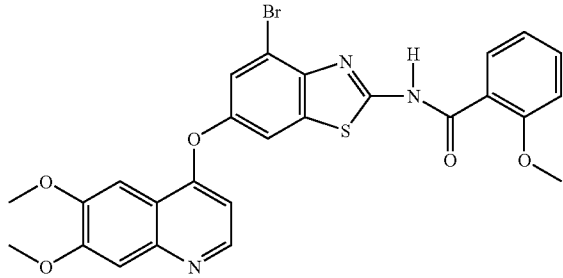<br>N-[4-Bromo-6-(6,7-dimethoxy-quinolin-4-yloxy)-benzothiazol-2-yl]-2-methoxy-benzamide | $C_{26}H_{20}BrN_3O_5S$ | 566.430 | 567 (M + 1) |

The following were prepared similar to that described in Example 1.

| Ex. No. | Structure & Name | Mol Formula | MW | M + H |
|---|---|---|---|---|
| 48 | 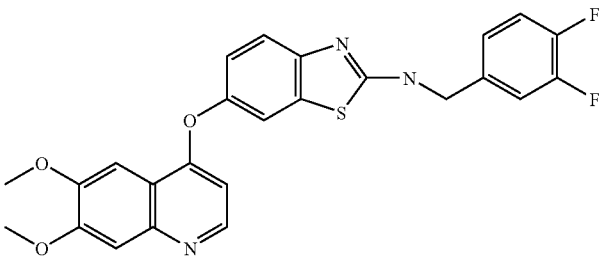<br>(3,4-Difluoro-benzyl)-[6-(6,7-dimethoxy-quinolin-4-yloxy)-benzothiazol-2-yl]-amine | $C_{25}H_{19}F_2N_3O_3S$ | 479.505 | 479 |
| 49 | 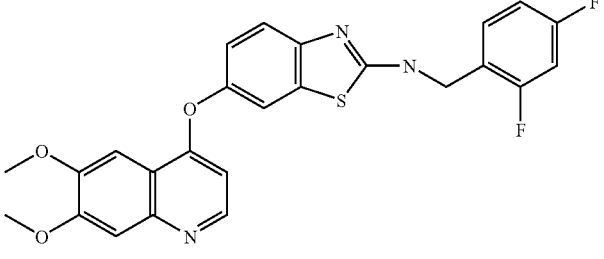<br>(2,4-Difluoro-benzyl)-[6-(6,7-dimethoxy-quinolin-4-yloxy)-benzothiazol-2-yl]-amine | $C_{25}H_{19}F_2N_3O_3S$ | 479.505 | 479 |
| 50 | 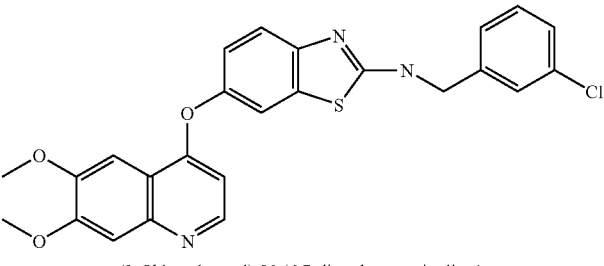<br>(3-Chloro-benzyl)-[6-(6,7-dimethoxy-quinolin-4-yloxy)-benzothiazol-2-yl]-amine | $C_{25}H_{20}ClN_3O_3S$ | 477.970 | 477.5 |
| 51 | 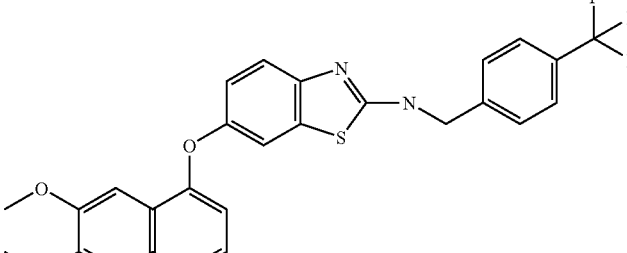<br>[6-(6,7-Dimethoxy-quinolin-4-yloxy)-benzothiazol-2-yl]-(4-trifluoromethyl-benzyl)-amine | $C_{26}H_{20}F_3N_3O_3S$ | 511.522 | 511 |

| Ex. No. | Structure & Name | Mol Formula | MW | M + H |
|---|---|---|---|---|
| 52 | 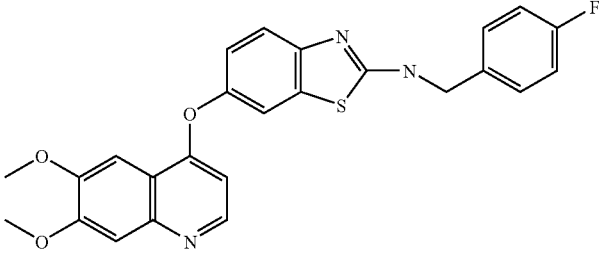<br>[6-(6,7-Dimethoxy-quinolin-4-yloxy)-benzothiazol-2-yl]-(4-fluoro-benzyl)-amine | $C_{25}H_{20}FN_3O_3S$ | 461.515 | 461 |
| 53 | 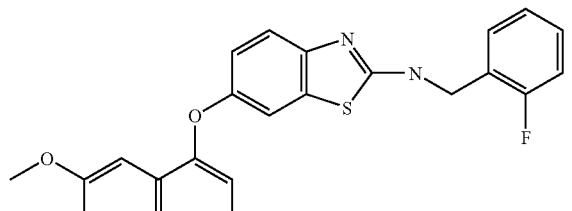<br>[6-(6,7-Dimethoxy-quinolin-4-yloxy)-benzothiazol-2-yl]-(2-fluoro-benzyl)-amine | $C_{25}H_{20}FN_3O_3S$ | 461.515 | 461 |
| 54 | 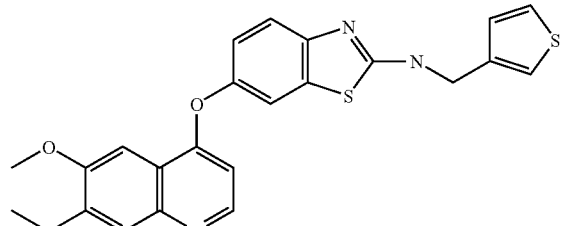<br>[6-(6,7-Dimethoxy-quinolin-4-yloxy)-benzothiazol-2-yl]-thiophen-3-ylmethyl-amine | $C_{23}H_{19}N_3O_3S_2$ | 449.553 | 449 |
| 55 | 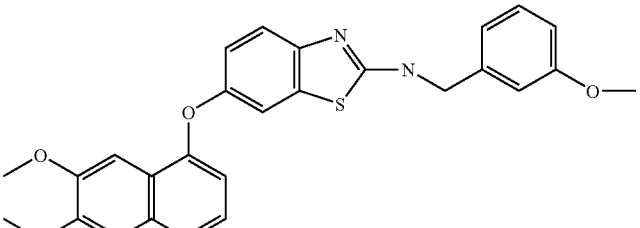<br>[6-(6,7-Dimethoxy-quinolin-4-yloxy)-benzothiazol-2-yl]-(3-methoxy-benzyl)-amine | $C_{26}H_{23}N_3O_4S$ | 473.551 | 473 |
| 56 | 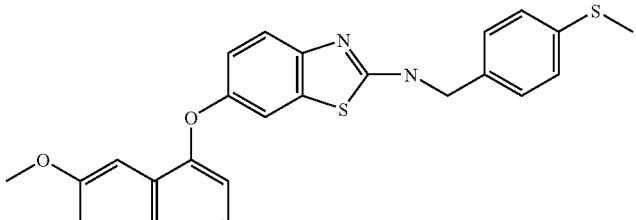<br>[6-(6,7-Dimethoxy-quinolin-4-yloxy)-benzothiazol-2-yl]-(4-methylsulfanyl-benzyl)-amine | $C_{26}H_{23}N_3O_3S_2$ | 489.618 | 489 |

| Ex. No. | Structure & Name | Mol Formula | MW | M + H |
|---|---|---|---|---|
| 57 | 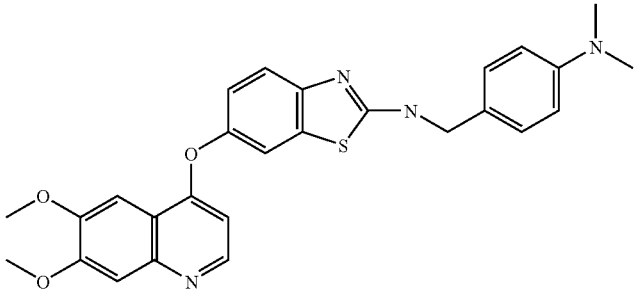<br>[6-(6,7-Dimethoxy-quinolin-4-yloxy)-benzothiazol-2-yl]-(4-dimethylamino-benzyl)-amine | $C_{27}H_{26}N_4O_3S$ | 486.593 | 486 |
| 58 | 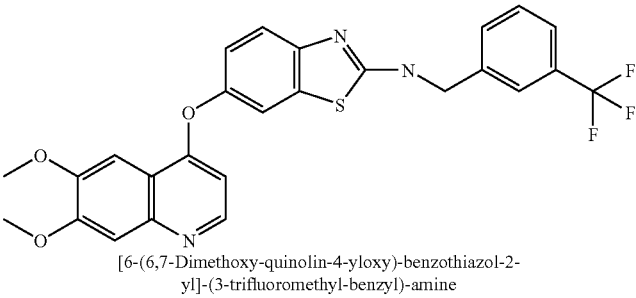<br>[6-(6,7-Dimethoxy-quinolin-4-yloxy)-benzothiazol-2-yl]-(3-trifluoromethyl-benzyl)-amine | $C_{26}H_{20}F_3N_3O_3S$ | 511.522 | 511 |
| 59 | 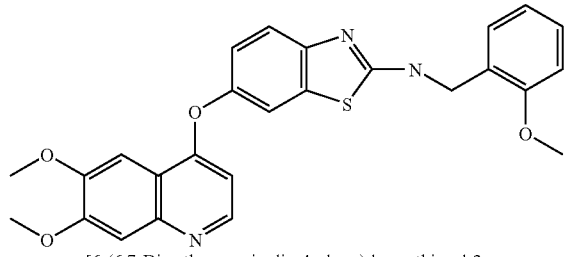<br>[6-(6,7-Dimethoxy-quinolin-4-yloxy)-benzothiazol-2-yl]-(2-methoxy-benzyl)-amine | $C_{26}H_{23}N_3O_4S$ | 473.551 | 473 |
| 60 | 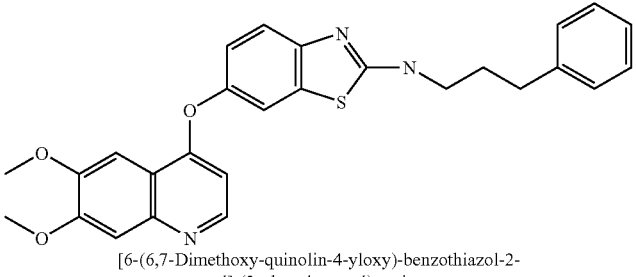<br>[6-(6,7-Dimethoxy-quinolin-4-yloxy)-benzothiazol-2-yl]-(3-phenyl-propyl)-amine | $C_{27}H_{25}N_3O_3S$ | 471.578 | 471 |
| 61 | 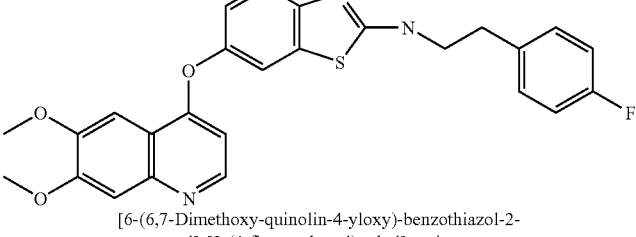<br>[6-(6,7-Dimethoxy-quinolin-4-yloxy)-benzothiazol-2-yl]-[2-(4-fluoro-phenyl)-ethyl]-amine | $C_{26}H_{22}FN_3O_3S$ | 475.542 | 475 |

-continued

| Ex. No. | Structure & Name | Mol Formula | MW | M + H |
|---|---|---|---|---|
| 62 | 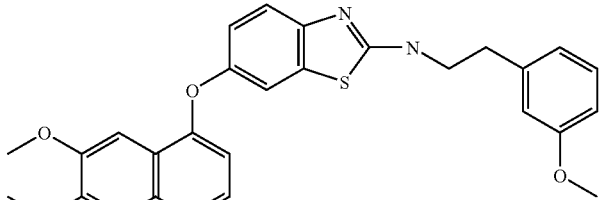 [6-(6,7-Dimethoxy-quinolin-4-yloxy)-benzothiazol-2-yl]-[2-(3-niethoxy-phenyl)-ethyl]-amine | $C_{27}H_{25}N_3O_4S$ | 487.578 | 487 |
| 63 | 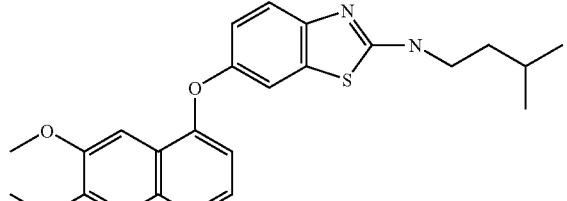 [6-(6,7-Dimethoxy-quinolin-4-yloxy)-benzothiazol-2-yl]-(3-methyl-butyl)-amine | $C_{23}H_{25}N_3O_3S$ | 423.534 | 423 |
| 64 | 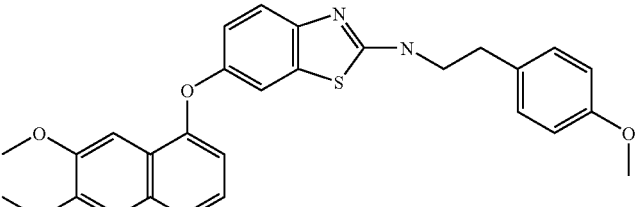 [6-(6,7-Dimethoxy-quinolin-4-yloxy)-benzothiazol-2-yl]-[2-(4-methoxy-phenyl)-ethyl]-amine | $C_{27}H_{25}N_3O_4S$ | 487.578 | 487 |

The following compounds were prepared similar to that described in Example 1 or 2.

| Ex. No. | Structure & Name | Formula | MW | M + H | Proc. No. |
|---|---|---|---|---|---|
| 65 | 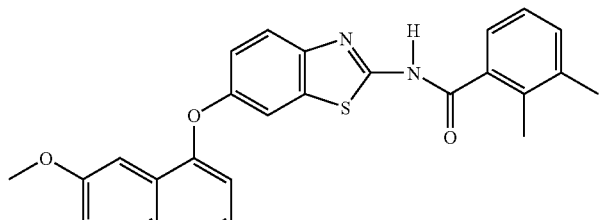 N-[6-(6,7-Dimethoxy-quinolin-4-yloxy)-benzothiazol-2-yl]-2,3-dimethyl-benzamide | $C_{27}H_{23}N_3O_4S$ | 485.562 | 486 | 2 |

-continued

| Ex. No. | Structure & Name | Formula | MW | M + H | Proc. No. |
|---|---|---|---|---|---|
| 66 | 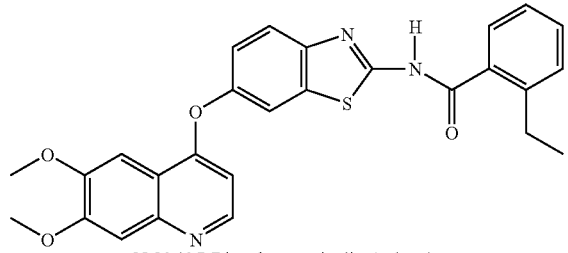<br>N-[6-(6,7-Dimethoxy-quinolin-4-yloxy)-benzothiazol-2-yl]-2-ethyl-benzamide | $C_{27}H_{23}N_3O_4S$ | 485.562 | 486 | 2 |
| 67 | 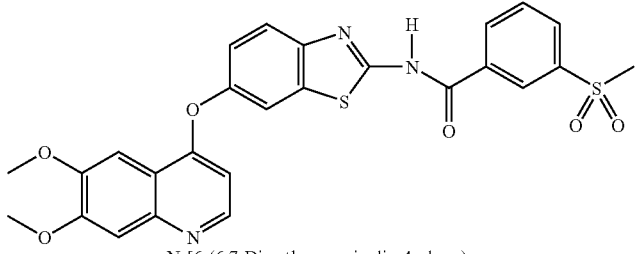<br>N-[6-(6,7-Dimethoxy-quinolin-4-yloxy)-benzothiazol-2-yl]-3-methanesulfonyl-benzamide | $C_{26}H_{21}N_3O_6S_2$ | 535.599 | 536 | 2 |
| 68 | 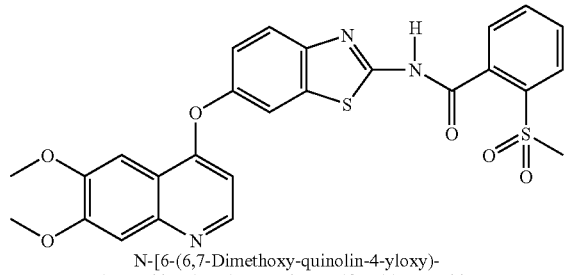<br>N-[6-(6,7-Dimethoxy-quinolin-4-yloxy)-benzothiazol-2-yl]-2-methanesulfonyl-benzamide | $C_{26}H_{21}N_3O_6S_2$ | 535.599 | 536 | 2 |
| 69 | 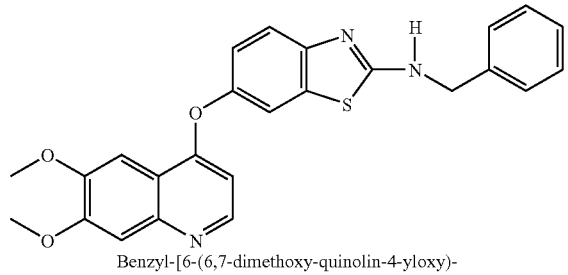<br>Benzyl-[6-(6,7-dimethoxy-quinolin-4-yloxy)-benzothiazol-2-yl]-amine | $C_{25}H_{21}N_3O_3S$ | 443.525 | 444 | 1 |
| 70 | 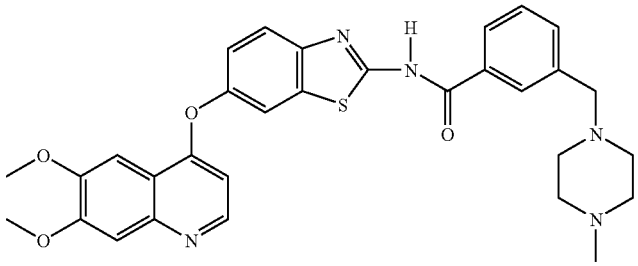<br>N-[6-(6,7-Dimethoxy-quinolin-4-yloxy)-benzothiazol-2-yl]-3-(4-methyl-piperazin-1-ylmethyl)-benzamide | $C_{31}H_{31}N_5O_4S$ | 569.683 | 570 | 2 |

| Ex. No. | Structure & Name | Formula | MW | M + H | Proc. No. |
|---|---|---|---|---|---|
| 71 | 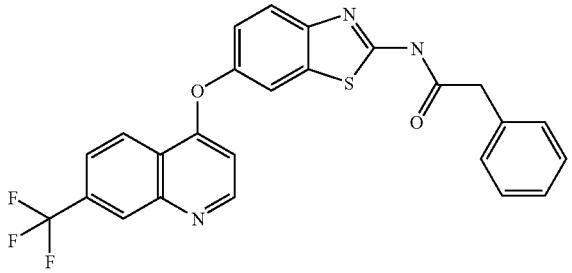<br>2-Phenyl-N-[6-(7-trifluoromethyl-quinolin-4-yloxy)-benzothiazol-2-yl]-acetamide | $C_{25}H_{16}F_3N_3O_2S$ | 479.480 | 480.2 | 2 |
| 72 | 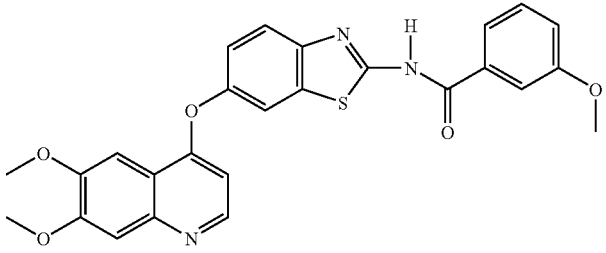<br>n-[6-(6,7-Dimethoxy-quinolin-4-yloxy)-benzothiazol-2-yl]-3-methoxy-benzamide | $C_{26}H_{21}N_3O_5S$ | 487.534 | 488 | 2 |
| 73 | 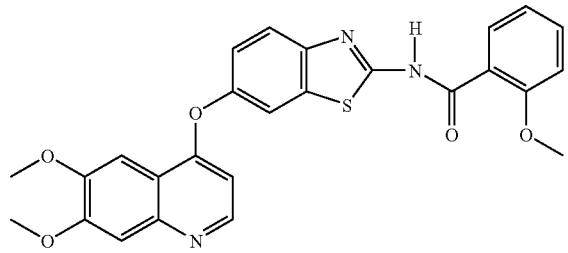<br>N-[6-(6,7-Dimethoxy-quinolin-4-yloxy)-benzothiazol-2-yl]-2-methoxy-benzamide | $C_{26}H_{21}N_3O_5S$ | 487.534 | 488 | 2 |
| 74 | 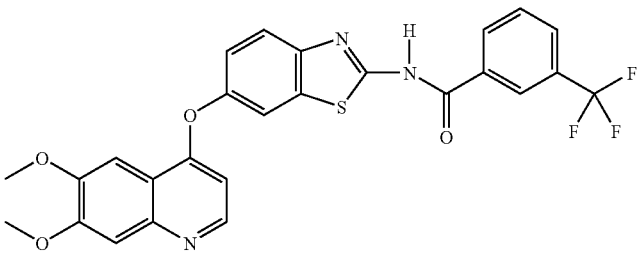<br>N-[6-(6,7-Dimethoxy-quinolin-4-yloxy)-benzothiazol-2-yl]-3-trifluoromethyl-benzamide | $C_{26}H_{18}F_3N_3O_4S$ | 525.505 | 526 | 2 |
| 75 | 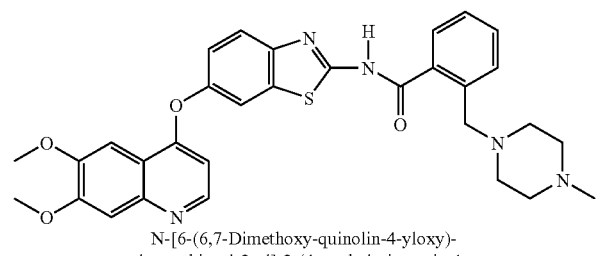<br>N-[6-(6,7-Dimethoxy-quinolin-4-yloxy)-benzothiazol-2-yl]-2-(4-methyl-piperazin-1-ylmethyl)-benzamide | $C_{31}H_{31}N_5O_4S$ | 569.683 | 570 | 2 |

-continued

| Ex. No. | Structure & Name | Formula | MW | M + H | Proc. No. |
|---|---|---|---|---|---|
| 76 | 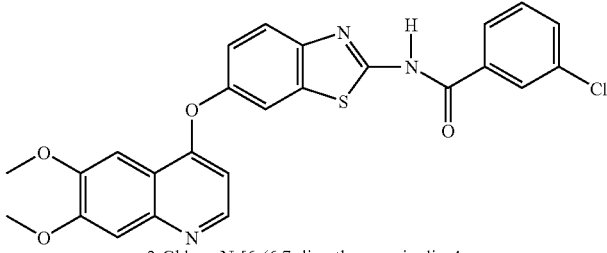<br>3-Chloro-N-[6-(6,7-dimethoxy-quinolin-4-yloxy)-benzothiazol-2-yl]-benzamide | $C_{25}H_{18}ClN_3O_4S$ | 491.953 | 492 | 2 |
| 77 | 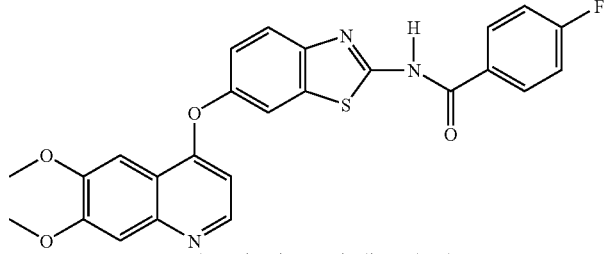<br>N-[6-(6,7-Dimethoxy-quinolin-4-yloxy)-benzothiazol-2-yl]-4-fluoro-benzamide | $C_{25}H_{18}FN_3O_4S$ | 475.498 | 476 | 2 |
| 78 | 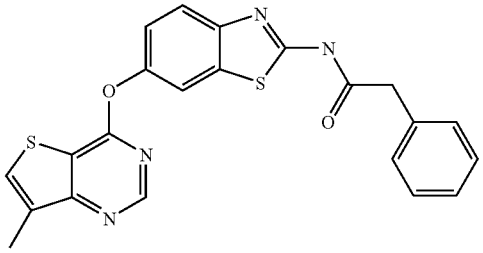<br>N-[6-(7-Methyl-thieno[3,2-d]pyrimidin-4-yloxy)-benzothiazol-2-yl]-2-phenyl-acetamide | $C_{22}H_{16}N_4O_2S_2$ | 432.526 | 433.1 | 2 |
| 79 | 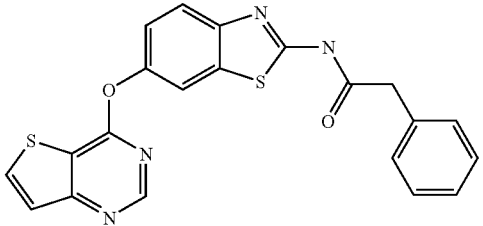<br>2-Phenyl-N-[6-(thieno[3,2-d]pyrimidin-4-yloxy)-benzothiazol-2-yl]-acetamide | $C_{21}H_{14}N_4O_2S_2$ | 418.500 | 419.1 | 2 |
| 80 | 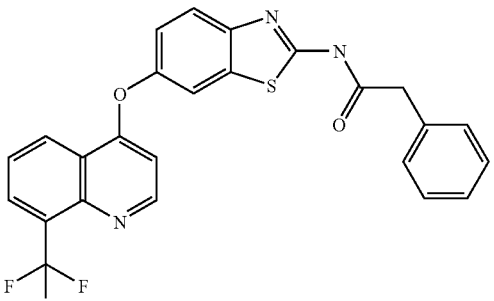<br>2-Phenyl-N-[6-(8-trifluoromethyl-quinolin-4-yloxy)-benzothiazol-2-yl]-acetamide | $C_{25}H_{16}F_3N_3O_2S$ | 479.480 | 480.3 | 2 |

-continued

| Ex. No. | Structure & Name | Formula | MW | M + H | Proc. No. |
|---|---|---|---|---|---|
| 81 | 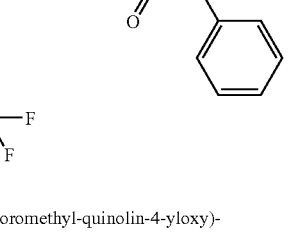<br>N-[6-(2,8-Bis-trifluoromethyl-quinolin-4-yloxy)-benzothiazol-2-yl]-2-phenyl-acetamide | $C_{26}H_{15}F_6N_3O_2S$ | 547.477 | 548.2 | 2 |
| 82 | 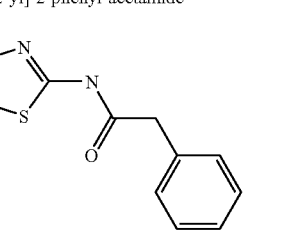<br>N-[6-(2-Methyl-pyridin-4-yloxy)-benzothiazol-2-yl]-2-phenyl-acetamide | $C_{21}H_{17}N_3O_2S$ | 375.450 | 376.1 | 2 |
| 83 | 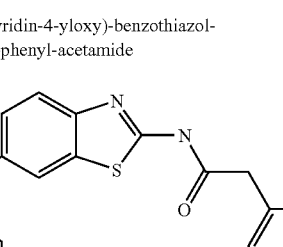<br>N-{6-[5-(3-Methoxy-phenyl)-pyrimidin-4-yloxy]-benzothiazol-2-yl}-2-phenyl-acetamide | $C_{26}H_{20}N_4O_3S$ | 468.535 | 469.2 | 2 |
| 84 | 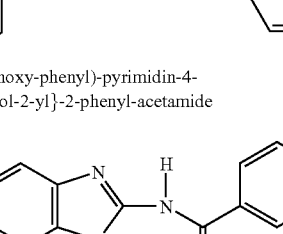<br>N-[6-(6,7-Dimethoxy-quinolin-4-yloxy)-benzothiazol-2-yl]-benzamide | $C_{25}H_{19}N_3O_4S$ | 457.508 | 458 | 2 |
| 85 | 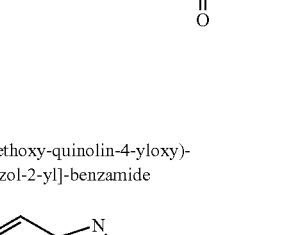<br>N-[6-(6,7-Dimethoxy-quinazolin-4-yloxy)-benzothiazol-2-yl]-2-phenyl-acetamide | $C_{25}H_{20}N_4O_4S$ | 472.523 | 473 | 2 |

-continued
| Ex. No. | Structure & Name | Formula | MW | M + H | Proc. No. |
|---|---|---|---|---|---|
| 86 | 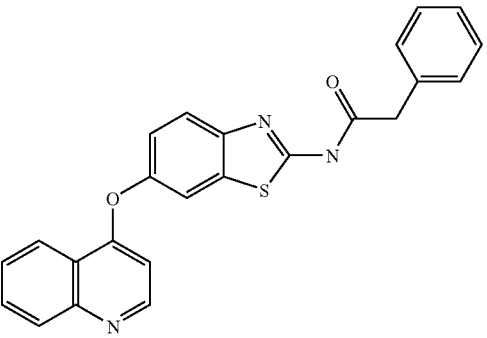<br>2-Phenyl-N-[6-(quinolin-4-yloxy)-benzothiazol-2-yl]-acetamide | $C_{24}H_{17}N_3O_2S$ | 411.483 | 412.0 | 2 |
| 87 | 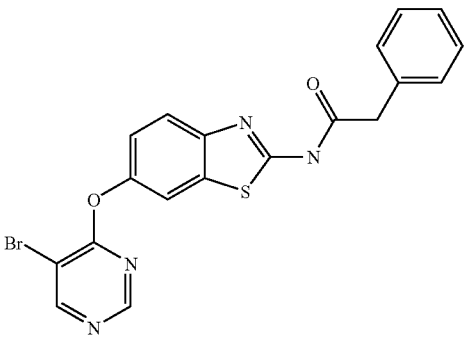<br>N-[6-(5-Bromo-pyrimidin-4-yloxy)-benzothiazol-2-yl]-2-phenyl-acetamide | $C_{19}H_{13}BrN_4O_2S$ | 441.308 | 443.3 | 2 |
| 88 | 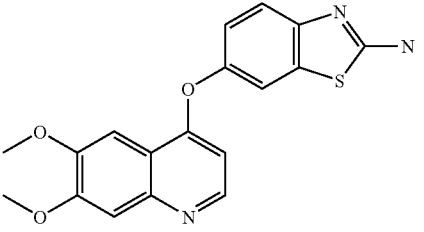<br>6-(6,7-Dimethoxy-quinolin-4-yloxy)-benzothiazol-2-ylamine | $C_{18}H_{15}N_3O_3S$ | 353.401 | 354 | 1a |
| 89 | 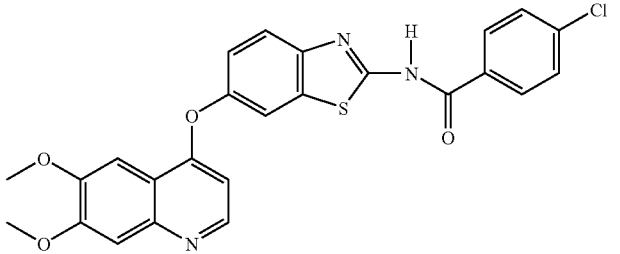<br>4-Chloro-N-[6-(6,7-dimethoxy-quinolin-4-yloxy)-benzothiazol-2-yl]-benzamide | $C_{25}H_{18}ClN_3O_4S$ | 491.953 | 492 | 2 |
| 90 | 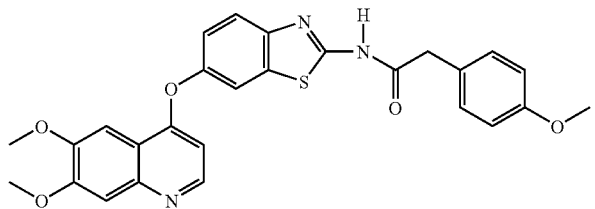 | $C_{27}H_{23}N_3O_5S$ | 501.561 | 502 | 2 |

| Ex. No. | Structure & Name | Formula | MW | M + H | Proc. No. |
|---|---|---|---|---|---|
| | N-[6-(6,7-Dimethoxy-quinolin-4-yloxy)-benzothiazol-2-yl]-2-(4-methoxy-phenyl)-acetamide | | | | |
| 91 | Thiophene-2-carboxylic acid [6-(6,7-dimethoxy-quinolin-4-yloxy)-benzothiazol-2-yl]-amide | $C_{23}H_{17}N_3O_4S_2$ | 463.536 | 463 | 2 |
| 92 | N-[6-(6,7-Dimethoxy-quinolin-4-yloxy)-benzothiazol-2-yl]-2-thiophen-2-yl-acetamide | $C_{24}H_{19}N_3O_4S_2$ | 477.563 | 477 | 2 |
| 93 | N-[6-(6,7-Dimethoxy-quinolin-4-yloxy)-benzothiazol-2-yl]-2-phenyl-acetamide | $C_{26}H_{21}N_3O_4S$ | 471.535 | 472 | 2 |
| 94 | 5-Chloro-4-methoxy-thiophene-3-carboxylic acid [6-(6,7-dimethoxy-quinolin-4-yloxy)-benzothiazol-2-yl]-amide | $C_{24}H_{18}ClN_3O_5S_2$ | 527.04 | 527.5 | 2 |
| 95 | | $C_{25}H_{19}N_3O_4S$ | 457.508 | 458 | 3 |

| Ex. No. | Structure & Name | Formula | MW | M + H | Proc. No. |
|---|---|---|---|---|---|
| | 2-Methoxy-N-[6-(6-methoxy-quinolin-4-yloxy)-benzothiazol-2-yl]-benzamide | | | | |
| 96 | 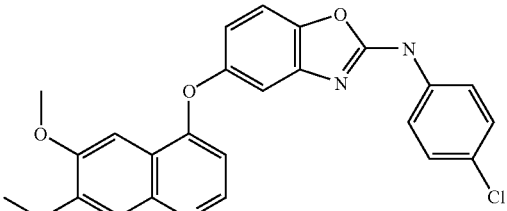<br>5-((6,7-bis(methoxy)-4-quinolinyl)oxy)-N-(4-chlorophenyl)-1,3-benzoxazol-2-amine | $C_{24}H_{18}ClN_3O_4$ | 447.10 | 448 | 2 |
| 97 | 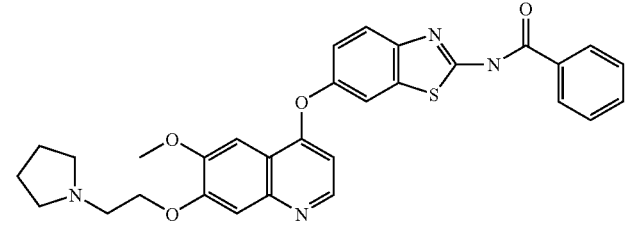<br>N-(6-((6-(methoxy)-7-((2-(1-pyrrolidinyl)ethyl)oxy)-4-quinolinyl)oxy)-1,3-benzothiazol-2-yl)benzamide | $C_{30}H_{28}N_4O_4S$ | 540.18 | 541 | 2 |
| 98 | 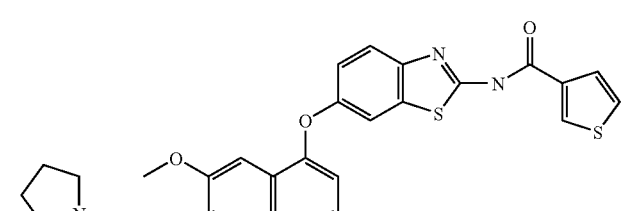<br>N-(6-((6-(methoxy)-7-((2-(1-pyrrolidinyl)ethyl)oxy)-4-quinolinyl)oxy)-1,3-benzothiazol-2-yl)-3-thiophenecarboxamide | $C_{28}H_{26}N_4O_4S_2$ | 546.14 | 547 | 2 |
| 99 | 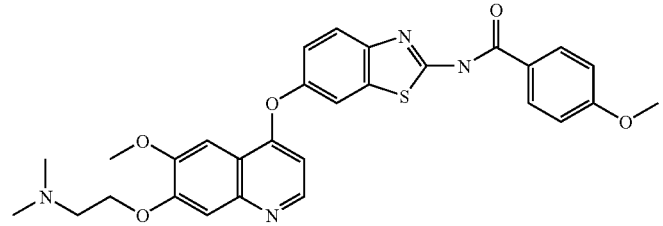<br>N-(6-((7-((2-(dimethylamino)ethyl)oxy)-6-(methoxy)-4-quinolinyl)oxy)-1,3-benzothiazol-2-yl)-4-(methylenyl)benzamide | $C_{29}H_{28}N_4O_5S$ | 544.18 | 545 | 2 |
| 100 | 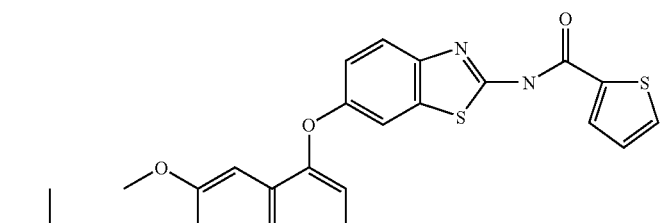<br>N-(6-((7-((2-(dimethylamino)ethyl)oxy)-6-(methoxy)-4-quinolinyl)oxy)-1,3-benzothiazol-2-yl)-2-thiophenecarboxamide | $C_{26}H_{24}N_4O_4S_2$ | 520.12 | 521 | 2 |

-continued

| Ex. No. | Structure & Name | Formula | MW | M + H | Proc. No. |
|---|---|---|---|---|---|
| 101 | 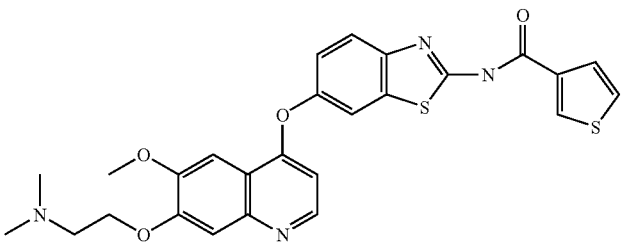<br>N-(6-((7-((2-(dimethylamino)ethyl)oxy)-6-(methoxy)-4-quinolinyl)oxy)-1,3-benzothiazol-2-yl)-3-thiophenecarboxamide | $C_{26}H_{24}N_4O_4S_2$ | 520.12 | 521 | 2 |
| 102 | 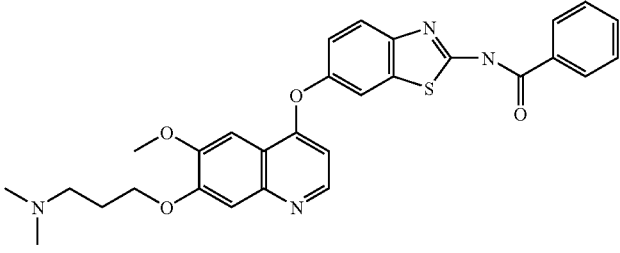<br>N-(6-((7-((3-(dimethylamino)propyl)oxy)-6-(methoxy)-4-quinolinyl)oxy)-1,3-benzothiazol-2-yl)benzamide | $C_{29}H_{28}N_4O_4S$ | 528.18 | 529 | 2 |
| 103 | 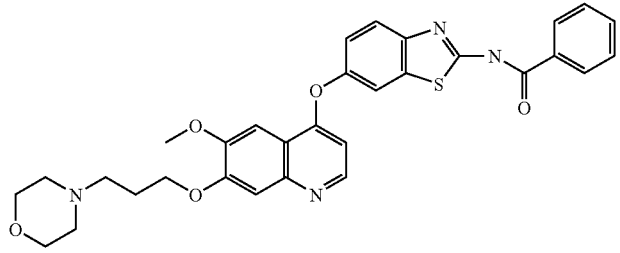<br>N-(6-((6-(methoxy)-7-((3-(4-morpholinyl)propyl)oxy)-4-quinolinyl)oxy)-1,3-benzothiazol-2-yl)benzamide | $C_{31}H_{30}N_4O_5S$ | 570.19 | 571 | 2 |
| 104 | 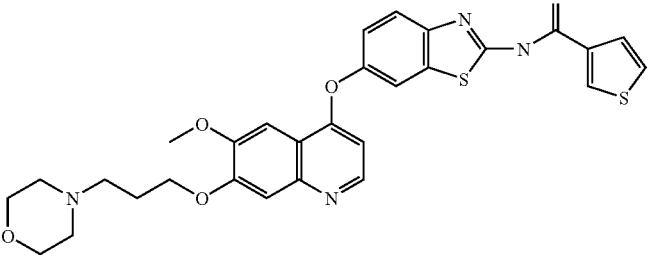<br>N-(6-((6-(methoxy)-7-((3-(4-morpholinyl)propyl)oxy)-4-quinolinyl)oxy)-1,3-benzothiazol-2-yl)-1-3-thiohenecarboxamide | $C_{29}H_{28}N_4O_5S_2$ | 576.15 | 577 | 2 |

Example 105

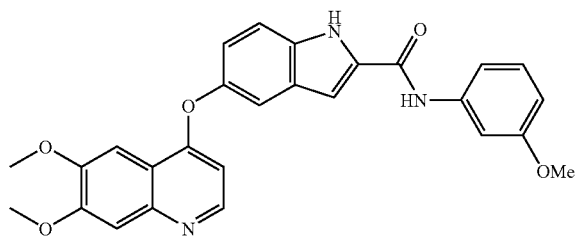

5-(6,7-Dimethoxy-quinolin-4-yloxy)-1H-indole-2-carboxylic acid (3-methoxy-phenyl)-amide (a) 5-(6,7-Dimethoxy-quinolin-4-yloxy)-1H-indole-2-carboxylic acid ethyl ester A mixture of 4-chloro-6,7-dimethoxy-quinoline (0.4 g, 1.8 mmol), 5-hydroxy-1H-indole-2-carboxylic acid ethyl ester (0.37 g, 1.8 mmol, Biosynth AG) and DMAP (0.22 g, 1.8 mmol, Aldrich) in toluene (in a microwave tube) was heated in a microwave (Personal Chemistry, Emrys Optimizer) at 180° C. for 2 h. The mixture was cooled to RT and diluted with 30 mL of EtOAc. The solution was washed with 10 mL of brine twice, dried over $Na_2SO_4$ and concentrated in vacuo. The residue was further purified with silica gel column chromatography (50% to 100% EtOAc in hexanes) to provide a white foam as the desired compound. MS (ESI pos. ion) m/z: 393 (M+H). Calc'd Exact Mass for $C_{22}H_{20}N_2O_5$: 392.40.

(b) 5-(6,7-Dimethoxy-quinolin-4-yloxy)-1H-indole-2-carboxylic acid

To a solution of 5-(6,7-dimethoxy-quinolin-4-yloxy)-1H-indole-2-carboxylic acid ethyl ester (0.2 g, 0.51 mmol, from step a) in 1:1 THF/MeOH (4 mL) was added 1.53 mL of 1N NaOH. The reaction was stirred at RT for 16 h then concentrated in vacuo. The remaining solution was acidified with 10% HCl to pH ~5. The white precipitate was collected, dried in vacuo to afford white solid as desired acid. MS (ESI pos. ion) m/z: 365 (M+H). Calc'd Exact Mass for $C_{20}H_{16}N_2O_5$: 364.35.

(c) 5-(6,7-Dimethoxy-quinolin-4-yloxy)-1H-indole-2-carboxylic acid (3-methoxy-phenyl)-amide To a solution of 5-(6,7-dimethoxy-quinolin-4-yloxy)-1H-indole-2-carboxylic acid (0.1 g, 0.27 mmol, from step b), 3-methoxy-phenylamine (68 mg, 0.55 mmol) and DIEA (0.1 mL, 0.55 mmol) in 3 mL of DMF was added PyBOP (0.29, 0.55 mmol, Aldrich) at RT. The reaction was stirred at RT for 16 h. The mixture was diluted with 50 mL of EtOAc, and the resulted solution was washed with 30 mL of satd. $NaHCO_3$ followed by 30 mL of brine. The organic phase was dried over $Na_2SO_4$ and concentrated in vacuo. The crude residue was purified by silica gel column chromatography (50% to 100% EtOAc/hexane) to afford off-white solid as desired product. MS (ESI pos. ion) m/z: 470 (M+H). Calc'd Exact Mass for $C_{27}H_{23}N_3O_5$: 469.49.

Example 106

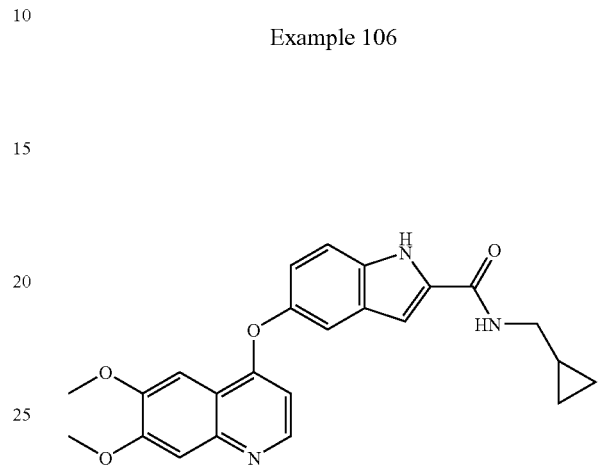

5-(6,7-Dimethoxy-quinolin-4-yloxy)-1H-indole-2-carboxylic acid cyclopropylmethyl-amide To a solution of 5-(6,7-dimethoxy-quinolin-4-yloxy)-1H-indole-2-carboxylic acid (1.2 g, 3.3 mmol, from Example 105, Step b), pentafluorophenol (1.21 g, 6.6 mmol, Aldrich) in 25 mL of EtOAc was added EDC (1.36 g, 6.6 mmol, Aldrich) at RT. The reaction was stirred at RT for 16 h. The mixture was diluted with 25 mL of EtOAc and filtered to remove the white solid. The filtrate was concentrated in vacuo to afford light yellow oil. This ester was used without further purification.

To a solution of 5-(6,7-dimethoxy-quinolin-4-yloxy)-1H-indole-2-carboxylic acid pentafluorophenyl ester (0.5 g, above) in 5 mL of THF was added cyclopropylmethylamine (0.175 g, 2.46 mmol, Aldrich) and resulting solution was stirred at RT for 8 h. The mixture was concentrated in vacuo. The residue was diluted with 50 mL of EtOAc and washed with 20 mL of satd. $NaHCO_3$ followed by 20 mL of brine. The organic phase was dried over $Na_2SO_4$ and concentrated in vacuo. The crude residue was purified by silica gel column chromatography (30% to 100% EtOAc/hexane) to afford white solid as desired product. MS (ESI pos. ion) m/z: 418 (M+H). Calc'd Exact Mass for $C_{24}H_{23}N_3O_4$: 417.46.

The following Examples were prepared similar to that described in Example 105.

| Example No. | Structure & Name | Mol Formula | MW | M + H |
|---|---|---|---|---|
| 107 | 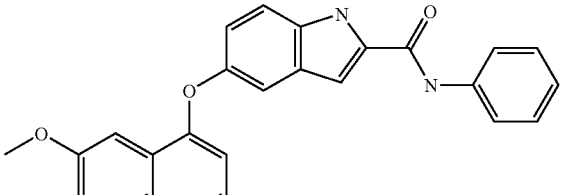<br>5-(6,7-Dimethoxy-quinolin-4-yloxy)-1H-indole-2-carboxylic acid phenylamide | $C_{26}H_{21}N_3O_4$ | 439.46 | 440 |
| 108 | 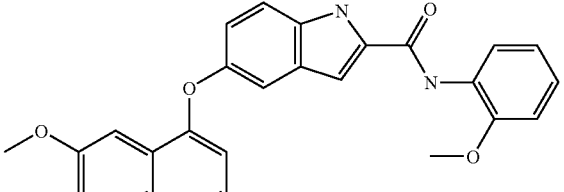<br>5-(6,7-Dimethoxy-quinolin-4-yloxy)-1H-indole-2-carboxylic acid (2-methoxy-phenyl)-amide | $C_{27}H_{23}N_3O_5$ | 469.49 | 470 |
| 109 | 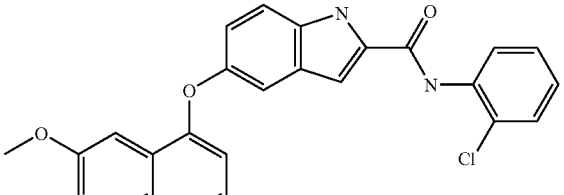<br>5-(6,7-Dimethoxy-quinolin-4-yloxy)-1H-indole-2-carboxylic acid (2-chloro-phenyl)-amide | $C_{26}H_{20}ClN_3O_4$ | 473.91 | 474 |
| 110 | 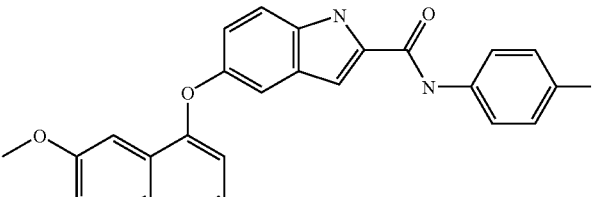<br>5-(6,7-Dimethoxy-quinolin-4-yloxy)-1H-indole-2-carboxylic acid (4-chlorophenyl)amide | $C_{26}H_{20}ClN_3O_4$ | 473.91 | 474 |
| 111 | 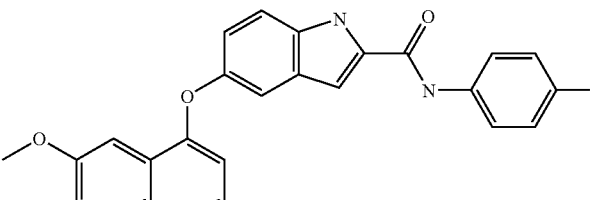<br>5-(6,7-Dimethoxy-quinolin-4-yloxy)-1H-indole-2-carboxylic acid (4-methoxy-phenyl)-amide | $C_{27}H_{25}N_3O_5$ | 469.49 | 470 |

-continued

| Example No. | Structure & Name | Mol Formula | MW | M + H |
|---|---|---|---|---|
| 112 | 5-(6,7-Dimethoxy-quinolin-4-yloxy)-1H-indole-2-carboxylic acid (6-methoxy-pyridin-3-yl)-amide | $C_{26}H_{22}N_4O_5$ | 470.48 | 471 |
| 113 | 5-(6,7-Dimethoxy-quinolin-4-yloxy)-1H-indole-2-carboxylic acid (3-fluoro-phenyl)-amide | $C_{26}H_{20}FN_3O_4$ | 457.45 | 458 |
| 114 | 5-(6,7-Dimethoxy-quinolin-4-yloxy)-1H-indole-2-carboxylic acid pyridin-2-ylamide | $C_{25}H_{20}N_4O_4$ | 440.45 | 441 |
| 115 | 5-(6,7-Dimethoxy-quinolin-4-yloxy)-1H-indole-2-carboxylic acid thiazol-2-ylamide | $C_{23}H_{18}N_4O_4S$ | 446.48 | 447 |
| 116 | 5-(6,7-Dimethoxy-quinolin-4-yloxy)-1H-indole-2-carboxylic acid (1H-pyrazol-3-yl)-amide | $C_{23}H_{19}N_5O_4$ | 429.43 | 430 |

The following Examples were prepared similar to that described in Example 106.

| Example No. | Structure & Name | Mol Formula | MW | M + H |
|---|---|---|---|---|
| 117 | 5-(6,7-Dimethoxy-quinolin-4-yloxy)-1H-indole 2-carboxylic acid isobutyl-amide | $C_{24}H_{25}N_3O_4$ | 419.47 | 420 |
| 118 | 5-(6,7-Dimethoxy-quinolin-4-yloxy)-1H-indole-2-carboxylic acid cyclopentylamide | $C_{25}H_{25}N_3O_4$ | 431.48 | 432 |
| 119 | [5-(6,7-Dimethoxy-quinolin-4-yloxy)-1H-indol-2-yl]-(4-methyl-piperazin-1-yl)-methanone | $C_{25}H_{26}N_4O_4$ | 446.50 | 447 |

Example 120

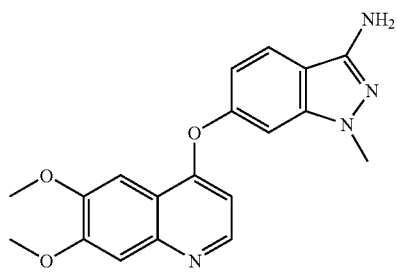

6-((6,7-bis(methyloxy)-4-quinolinyl)oxy)-1-methyl-1H-indazol-3-amine

Step (a) Preparation of 3-amino-1-methyl-1H-indazol-6-ol

A solution of 6-fluoro-4-hydroxy benzonitrile (Aldrich, 10.1 g, 73.9 mmol) in methyl hydrazine (Aldrich, 20.0 mL, 379 mmol) was stirred at 80° C. for 16 h. After cooling to RT, the volatile portion was removed in vacuo. The residue was triturated with DCM and MeOH. The title compound was obtained by filtration as an off-white solid. The filtrate was concentrated in vacuo and purified by silica gel chromatography (DCM/MeOH: 100/0 to 95/5) to give an additional amount of the title compound as a white solid.

Step (b) Preparation of 6-((6,7-bis(methyloxy)-4-quinolinyl)oxy)-1-methyl-1H-indazol-3-amine 4-Chloro-6,7-dimethoxyquinoline (2.60 g, 11.7 mmol), 3-amino-1-methyl-1H-indazol-6-ol (Step a, 2.72 g, 16.7 mmol) and cesium carbonate (Aldrich, 16.3 g, 50.1 mmol) in DMSO (16.7 mL, Aldrich) were stirred at 100° C. for 16 h. After cooling to RT, water was added. The aqueous layer was extracted with DCM. The organic phase was washed with water, dried with $MgSO_4$, filtered and concentrated in vacuo. Purification by silica gel chromatography using 0-100% of a 90:10:1 ($CH_2Cl_2$:MeOH:$NH_4OH$) solution as the eluant afforded the title compound as a white solid. MS (ESI, pos. ion) m/z: 351.1 (M+1). Mass Calc'd for $C_{19}H_{18}N_4O_3$: 350.38.

Example 121

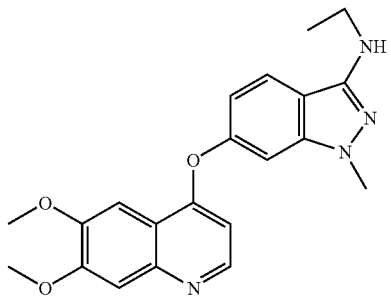

6-((6,7-bis(Methoxy)-4-quinolinyl)oxy)-N-ethyl-1-methyl-1H-indazol-3-amine

To a stirred solution of 6-((6,7-bis(methyloxy)-4-quinolinyl)oxy)-1-methyl-1H-indazol-3-amine (Example 120, 140 mg, 0.40 mmol) in dry DCM (Aldrich, 4.0 mL) at RT were added acetaldehyde (Aldrich, 21.1 mg, 0.48 mmol) followed by $NaHB(OAc)_3$ (Aldrich, 102 mg, 0.48 mmol). After being stirred for 4 h at RT, the reaction was quenched by addition of water. The aqueous layer was extracted with DCM. The organic layer was dried with $MgSO_4$, filtered and concentrated in vacuo. Purification by silica gel chromatography (DCM/acetone: 100/0 to 60/40) afforded the title compound. MS (ESI, pos. ion) m/z: 379.3 (M+1). Mass Calc'd for $C_{21}H_{22}N_4O_3$: 378.43.

The following compound was also isolated from the reaction mixture:

| Example No. | Structure & Name | Mol Formula | Mass | M + H |
|---|---|---|---|---|
| 122 | 6-((6,7-bis(methoxy)-4-quinolinyl)oxy)-N,N-diethyl-1-methyl-1H-indazol-3-amine | $C_{23}H_{26}N_4O_3$ | 406.48 | 407.3 |

The following compounds were prepared similarly to the procedure outlined above:

| Example No. | Structure & Name | Mol Formula | Mass | M + H |
|---|---|---|---|---|
| 123 | 6-((6,7-bis(methyloxy)-4-quinolinyl)oxy)-1-methyl-N-propyl-1H-indazol-3-amine | $C_{22}H_{24}N_4O_3$ | 392.46 | 393.3 |

-continued

| Example No. | Structure & Name | Mol Formula | Mass | M + H |
|---|---|---|---|---|
| 124 | 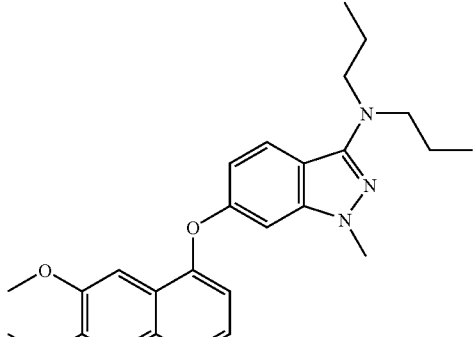<br>6-((6,7-bis(methyloxy)-4-quinolinyl)oxy)-1-methyl-N,N-dipropyl-1H-indazol-3-amine | $C_{25}H_{30}N_4O_3$ | 434.54 | 435.4 |
| 125 | 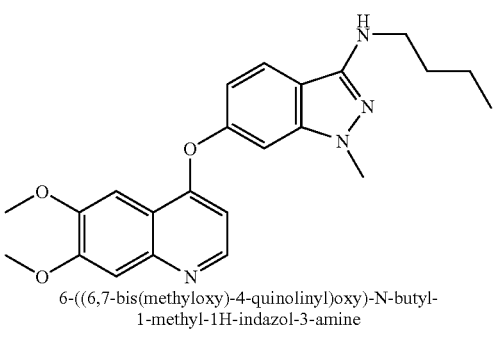<br>6-((6,7-bis(methyloxy)-4-quinolinyl)oxy)-N-butyl-1-methyl-1H-indazol-3-amine | $C_{23}H_{26}N_4O_3$ | 406.48 | 407.3 |
| 126 | 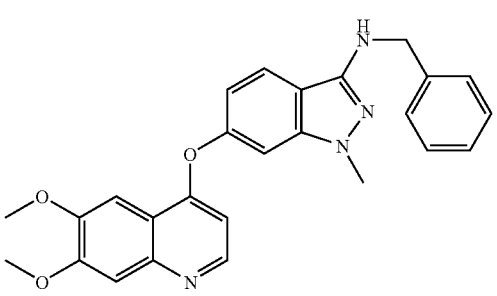<br>6-((6,7-bis(methyloxy)-4-quinolinyl)oxy)-1-methyl-N-(phenylmethyl)-1H-indazol-3-amine | $C_{26}H_{24}N_4O_3$ | 440.50 | 441.3 |
| 127 | 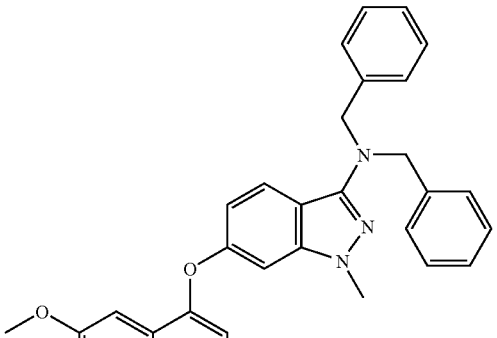<br>6-((6,7-bis(methyloxy)-4-quinolinyl)oxy)-1-methyl-N,N-bis(phenylmethyl)-1H-indazol-3-amine | $C_{33}H_{30}N_4O_3$ | 530.63 | 531.4 |

Example 128

6-((6,7-bis(Methoxy)-4-quinolinyl)oxy)-1-methyl-N-phenyl-1H-indazol-3-amine

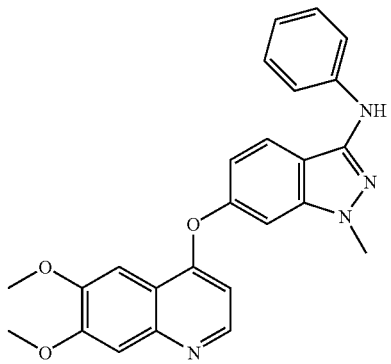

A solution/suspension of $Pd_2dba_3$ (9.30 mg, 0.01 mmol), 2-(dicyclohexylphosphino)-2'-4'-6'-tri-i-propyl-1,1'-biphenyl (19.5 mg, 0.04 mmol), sodium tert-butoxide (46.0 mg, 0.48 mmol), 6-((6,7-bis(methyloxy)-4-quinolinyl)oxy)-1-methyl-1H-indazol-3-amine (Example 120, 119 mg, 0.34 mmol) and bromobenzene (53.4 mg, 0.34 mmol) in toluene (1 mL) was stirred at 100° C. for 16 h. After cooling to RT, the mixture was purified by silica gel chromatography (DCM/acetone: 100/0 to 70/30) to give the title compound as a white solid. MS (ESI, pos. ion) m/z: 427.3 (M+1). Mass Calc'd for $C_{25}H_{22}N_4O_3$: 426.47.

The following compounds were prepared similarly to the procedure outlined above:

| Example No. | Structure & Name | Mol Formula | Mass | M + H |
|---|---|---|---|---|
| 129 | 6-((6,7-bis(methyloxy)-4-quinolinyl)oxy)-1-methyl-N-(4-(methyloxy)phenyl)-1H-indazol-3-amine | $C_{26}H_{24}N_4O_4$ | 456.50 | 457.1 |
| 130 | 6-((6,7-bis(methyloxy)-4-quinolinyl)oxy)-1-methyl-N-(3-(methyloxy)phenyl)-1H-indazol-3-amine | $C_{26}H_{24}N_4O_4$ | 456.50 | 457.1 |

-continued

| Example No. | Structure & Name | Mol Formula | Mass | M + H |
|---|---|---|---|---|
| 131 | 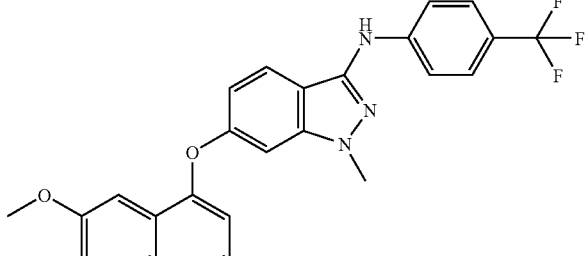<br>6-((6,7-bis(methyloxy)-4-quinolinyl)oxy)-1-methyl-N-(4-(trifluoromethyl)phenyl)-1H-indazol 3-amine | $C_{26}H_{21}F_3N_4O_3$ | 494.47 | 495.1 |

Example 132

N-(6-((6,7-bis(methyloxy)-4-quinolinyl)oxy)-1-methyl-1H-indazol-3-yl)-4-(methyloxy)benzamide

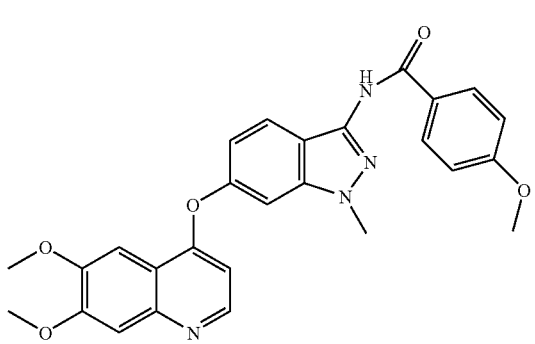

To a solution of 6-((6,7-bis(methyloxy)-4-quinolinyl)oxy)-1-methyl-1H-indazol-3-amine (Example 120, 119 mg, 0.34 mmol) in pyridine (1 mL), p-anisoyl chloride (116 mg, 0.68 mmol) was added. The reaction was stirred at RT for 16 h. The mixture was concentrated in vacuo. Trituration with MeOH and filtration afforded the title compound. MS (ESI, pos. ion) m/z: 485.1 (M+1). Mass Calc'd for $C_{25}H_{22}N_3$: 484.51.

The following compounds were prepared similarly to Example 132 and isolated after purification by silica gel chromatography and/or crystallization:

| Example No. | Structure & Name | Mol Formula | Mass | M + H |
|---|---|---|---|---|
| 133 | 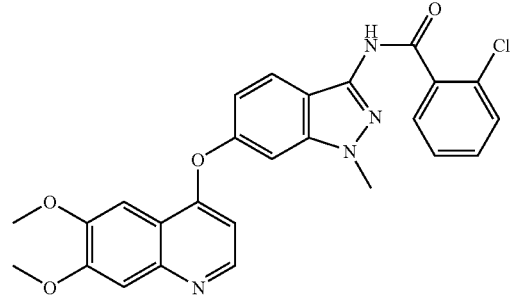<br>N-(6-((6,7-bis(methyloxy)-4-quinolinyl)oxy)-1-methyl-1H-indazol-3-yl)-2-chlorobenzamide | $C_{26}H_{21}ClN_4O_4$ | 488.93 | 489.1 |

-continued

| Example No. | Structure & Name | Mol Formula | Mass | M + H |
|---|---|---|---|---|
| 134 | 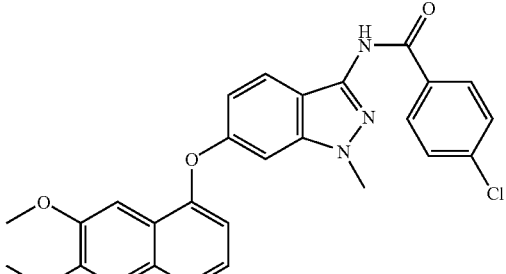<br>N-(6-((6,7-bis(methoxy)-4-quinolinyl)oxy)-1-methyl-1H-indazol-3-yl)-4-chlorobenzamide | $C_{26}H_{21}ClN_4O_4$ | 488.93 | 489.0 |
| 135 | 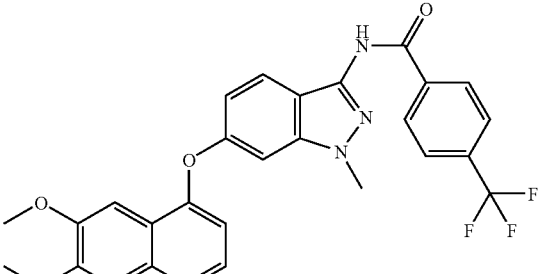<br>N-(6-((6,7-bis(methoxy)-4-quinolinyl)oxy)-1-methyl-1H-indazol-3-yl)-4-(trifluoromethyl)benzamide | $C_{27}H_{21}F_3N_4O_4$ | 522.48 | 523.0 |
| 136 | 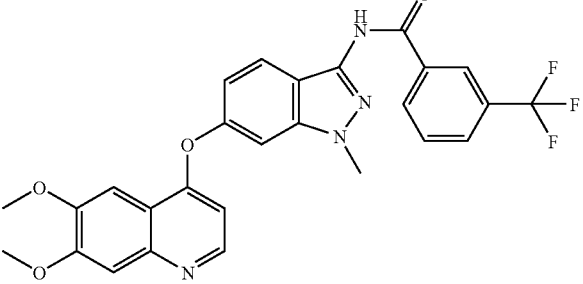<br>N-(6-((6,7-bis(methoxy)-4-quinolinyl)oxy)-1-methyl-1H-indazol-3-yl)-4-(trifluoromethyl)benzamide | $C_{27}H_{21}F_3N_4O_4$ | 522.48 | 523.0 |
| 137 | 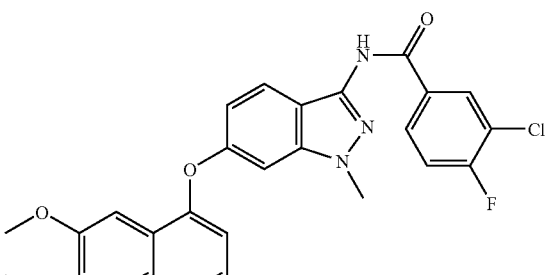<br>N-(6-((6,7-bis(methoxy)-4-quinolinyl)oxy)-1-methyl-1H-indazol-3-yl)-3-chloro-4-fluorobenzamide | $C_{26}H_{20}ClFN_4O_4$ | 506.92 | 507.0 |

-continued

| Example No. | Structure & Name | Mol Formula | Mass | M + H |
|---|---|---|---|---|
| 138 | 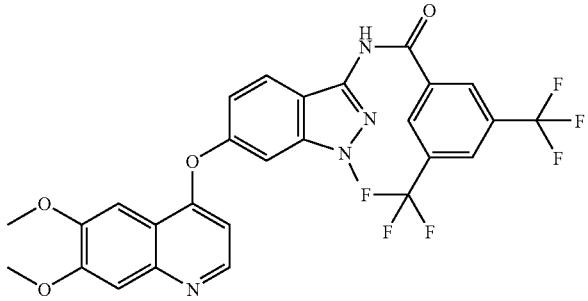<br>N-(6-((6,7-bis(methoxy)-4-quinolinyl)oxy)-1-methyl-1H-indazol-3-yl)-3,5-bis(trifluoromethyl)benzamide | $C_{28}H_{20}F_6N_4O_4$ | 590.48 | 591.0 |
| 139 | 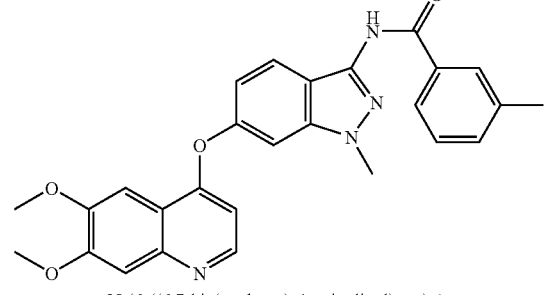<br>N-(6-((6,7-bis(methoxy)-4-quinolinyl)oxy)-1-methyl-1H-indazol-3-yl)-3-methylbenzamide | $C_{27}H_{24}N_4O_4$ | 468.51 | 469.0 |
| 140 | 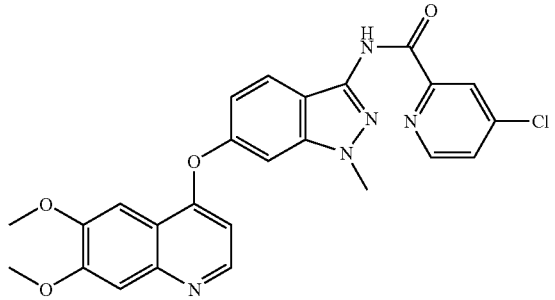<br>N-(6-((6,7-bis(methoxy)-4-quinolinyl)oxy)-1-methyl-1H-indazol-3-yl)-4-chloro-2-pyridinecarboxamide | $C_{25}H_{20}ClN_5O_4$ | 489.92 | 490.1 |
| 141 | 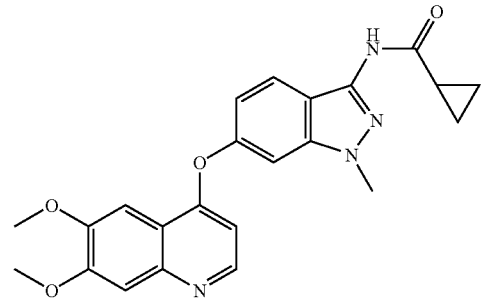<br>N-(6-((6,7-bis(methoxy)-4-quinolinyl)oxy)-1-methyl-1H-indazol-3-yl)cyclopropanecarboxamide | $C_{23}H_{22}N_4O_4$ | 418.45 | 419.2 |

Example 142

N-(6-(((6,7-bis(methoxy) quinolinyl) oxy)-1-methyl-1H-indazol-3-yl)-N'-(4-methylphenyl)urea

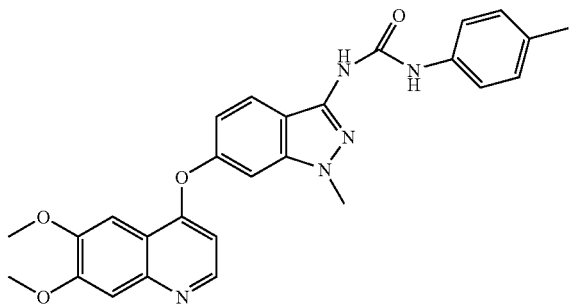

To a solution of 6-(((6,7-bis(methoxy)-4-quinolinyl)oxy)-1-methyl-1H-indazol-3-amine (Example 120, 115 mg, 0.33 mmol) in benzene (1 mL) was added p-tolyl isocyanate (87.6 mg, 0.66 mmol). The reaction was stirred at RT for 16 h. The mixture was concentrated in vacuo. Trituration with MeOH/EtOAc (1/1) and filtration afforded the title compound. MS (ESI, pos. ion) m/z: 484.0 (M+1). Mass Calc'd for $C_{27}H_{25}N_5O_4$: 483.53.

The following compounds were prepared similarly to Example 142 and isolated after purification by silica gel chromatography and/or crystallization:

| Example No. | Structure & Name | Mol Formula | Mass | M + H |
|---|---|---|---|---|
| 143 | N-(6-(((6,7-bis(methoxy)-4-quinolinyl)oxy)-1-methyl-1H-indazol-3-yl)-N'-(2-chloro-4-(trifluoromethyl)phenyl)urea | $C_{27}H_{21}ClF_3N_5O_4$ | 571.94 | 572.0 |
| 144 | N-(6-(((6,7-bis(methoxy)-4-quinolinyl)oxy)-1-methyl-1H-indazol-3-yl)-N'-phenylurea | $C_{26}H_{23}N_5O_4$ | 469.50 | 470.2 |
| 145 | N-(6-(((6,7-bis(methoxy)-4-quinolinyl)oxy)-1-methyl-1H-indazol-3-yl)-N'-(4-(methyloxy)phenyl)urea | $C_{27}H_{25}N_5O_5$ | 499.52 | 500.1 |

Example 146

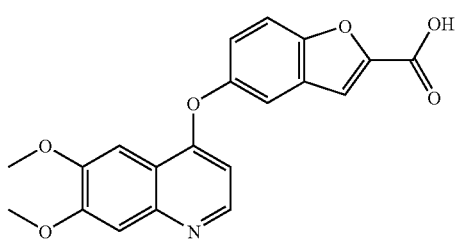

5-(6,7-Dimethoxyquinolin-4-yloxy)
benzofuran-2-carboxylic acid

Step (a) Preparation of 5-hydroxybenzofuran-2-carboxylic acid

A mixture of pyridine hydrochloride (15.1 g, 130 mmol) and 5-hydroxybenzofuran-2-carboxylic acid was heated at 150° C. for 24 h. After cooling at RT, water was added. The aqueous phase was acidified until pH=1 using 6M aqueous HCl and then extracted with EtOAc. The organic phase was dried over $MgSO_4$, filtered and concentrated in vacuo to give the title compound.

Step (b) Preparation of 5-(6,7-dimethoxyquinolin-4-yloxy)benzofuran-2-carboxylic acid To a stirred solution of 5-hydroxybenzofuran-2-carboxylic acid (Step a, 2.00 g, 11.23 mmol) in DMSO (23 mL) at RT was added cesium carbonate (11.0 g, 33.7 mmol). The reaction was stirred for 10 min followed by the addition of 4-chloro-6,7-dimethoxyquinoline (prepared by the method described in WO 03/33472) (1.75 g, 7.86 mmol). The reaction was stirred at 100° C. for 16 h. After cooling to RT, water was added. The aqueous layer was acidified with a 6M aqueous hydrochloric acid solution until pH=5, filtered and the solid was suspended in EtOAc. The organic phase was extracted with a 3M sodium hydroxide aqueous solution. After acidification of the aqueous layer, the title compound was isolated by filtration and dried under high vacuum.

The following compounds were prepared according to Example 146:

| No. | Structure & Name | Formula | Mass | M + H |
|---|---|---|---|---|
| 147 | 5-(6,7-dimethoxyquinolin-4-yloxy)-N-(3-fluorophenyl)benzofuran-2-carboxamide | $C_{26}H_{19}FN_2O_5$ | 458.44 | 459.0 |
| 148 | 5-(6,7-dimethoxyquinolin-4-yloxy)-N-(3-methoxyphenyl)benzofuran-2-carboxamide | $C_{27}H_{22}N_2O_6$ | 470.78 | 471.1 |
| 149 | 5-(6,7-dimethoxyquinolin-4-yloxy)-N-(4-fluorophenyl)benzofuran-2-carboxamide | $C_{26}H_{19}FN_2O_5$ | 458.44 | 459.0 |

-continued

| No. | Structure & Name | Formula | Mass | M + H |
|---|---|---|---|---|
| 150 | 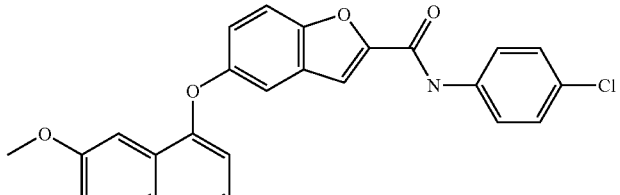<br>N-(4-chlorophenyl)-5-(6,7-dimethoxyquinolin-4-yloxy)benzofuran-2-carboxamide | C$_{26}$H$_{19}$ClN$_2$O$_5$ | 474.90 | 475.0 |

Example 151

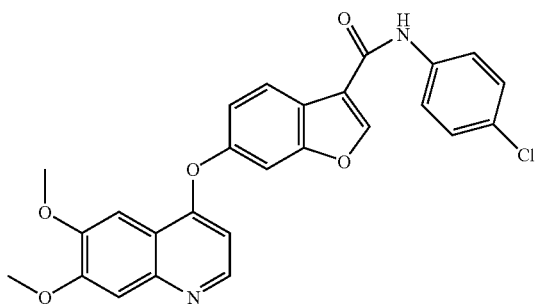

6-((6,7-bis(Methoxy)-4-quinolinyl) oxy)-N-(4-chlorophenyl)-1-benzofuran-3-carboxamide Step (a) Preparation of 6-methoxybenzofuran-3(2H)-one 6-Hydroxybenzofuran-3(2H)-one (6 g, 40.0 mmol) was dissolved in DMF (80 mL), then added potassium carbonate (6.07 g, 43.97 mmol) and methyl iodide (4.12 mL, 65.95 mmol). The reaction was stirred at RT for 2 days. The mixture was filtered and the filtrate was concentrated in vacuo. The remaining oil was dissolved in EtOAc and washed with water. The aqueous layer was back-extracted with EtOAc (2×). The organic layers were washed with brine, dried over sodium sulfate and concentrated in vacuo. The remaining orange-red solid was purified by silica gel chromatography (1:4 EtOAc/hexane) to afford 6-methoxybenzofuran-3(2H)-one as a bright yellow crystalline solid. MS (ESI, pos. ion) m/z: 165.1 (M+1).

Step (b) Preparation of 6-methoxybenzofuran-3-yl trifluoromethane sulfonate

6-Methoxybenzofuran-3(2H)-one (5.6 g, 34.15 mmol) was dissolved in dichloromethane (100 mL) then cooled to −65 C. N,N-diisopropylethylamine (6.84 mL, 39.27 mmol) was added dropwise via syringe, followed by addition of trifluoromethane sulfonic anhydride (6.88 mL, 40.97 mmol). The mixture was slowly warmed from −65 C to 0 C over 2.5 h. The reaction mixture was diluted with dichloromethane then washed with water and brine. The organic layer was dried over sodium sulfate and concentrated in vacuo. The remaining orange-brown liquid was purified by silica gel chromatography (5% ethyl acetate/hexane) to afford 6-methoxybenzofuran-3-yl trifluoromethane sulfonate as a light orange liquid. MS (ESI, pos. ion) m/z: 296.9 (M+1).

Step (c) Preparation of methyl 6-methoxybenzofuran-3-carboxylate

6-Methoxybenzofuran-3-yl trifluoromethane sulfonate (500 mg, 1.69 mmol) was added to a stainless steel high-pressure reaction vessel then dissolved in N,N-dimethylformamide (6.5 mL). Carbon monoxide gas was bubbled through the solution for 10 minutes. 1,3-Bis(diphenylphosphino)propane (21 mg, 0.051 mmol), methanol (1.8 mL), triethylamine (342 mg, 3.38 mmol) and palladium acetate (11 mg, 0.051 mmol) were added to the reaction mixture, while continuing to bubble carbon monoxide gas through the mixture. The reaction vessel was sealed and charged with carbon monoxide (30 psi). The reaction mixture was heated at 80 C for 4.5 hours. The mixture was concentrated in vacuo. The remaining orange mixture was purified by silica gel chromatography (5% ethyl acetate/hexane) to afford methyl 6-methoxybenzofuran-3-carboxylate as a light yellow solid. MS (ESI, pos. ion) m/z: 207.1 (M+1).

Step (d) Preparation of methyl 6-hydroxybenzofuran-3-carboxylate

Methyl 6-methoxybenzofuran-3-carboxylate (498 mg, 2.42 mmol) was dissolved in dichloromethane (100 mL) then cooled to −10 C. A solution of 1M boron tribromide in dichloromethane (9.67 mL, 9.67 mmol) was added slowly via syringe. The dark purple reaction mixture was warmed to RT over 3 h then continued stirring at RT for an additional 4 h. The mixture was slowly quenched with aqueous 1N hydrochloric acid until it became colorless. The mixture was diluted with dichloromethane and washed with water (2×) and brine. The organic layer was dried over sodium sulfate and concentrated in vacuo. The remaining orange-brown solid was purified by silica gel chromatography (1:4 EtOAc/hexane) to afford methyl 6-hydroxybenzofuran-3-carboxylate as an off-white solid. MS (ESI, neg. ion) m/z: 191.1 (M−1).

Step (e) Preparation of methyl 6-(6,7-dimethoxyquinolin-4-yloxy)benzofuran-3-carboxylate Methyl 6-hydroxybenzofuran-3-carboxylate (312 mg, 1.62 mmol) was dissolved in N,N-dimethylformamide (5 mL) then added 4-chloro-6,7-dimethoxyquinoline (451 mg, 2.02 mmol), 2-(dicyclohexylphosphino)-2',4',6'-triisopropyl-1,1'-biphenyl (77 mg, 0.162 mmol), palladium acetate (36 mg, 0.162 mmol) and potassium phosphate (687 mg, 3.24 mmol). The reaction mixture was stirred at 100° C. overnight. Additional palladium acetate (36 mg, 0.162 mmol) was added to the mixture and the heating was continued at 100° C. for 4 h. Additional 4-chloro-6,7-dimethoxyquinoline (181 mg, 0.812 mmol) and 2-(dicyclohexylphosphino)-2',4',6'-triisopropyl-1,1'-biphenyl (77 mg, 0.162 mmol) were added to the mixture and heating at 100° C. was continued for 2 days. The reaction mixture was filtered and the filtrate was concentrated in vacuo. The remaining orange oil was redissolved in toluene (5 mL) and DMF (1 mL) then added 4-chloro-6,7-dimethoxyquinoline (225 mg, 1.01 mmol), 2-(dicyclohexylphosphino)-2',4',6'-triisopropyl-1,1'-biphenyl (38 mg, 0.080 mmol), palladium acetate (18 mg, 0.080 mmol) and potassium phosphate (343 mg, 1.62 mmol). The reaction mixture was heated at 100° C. overnight and concentrated in vacuo. The remaining orange-black oil was purified by silica gel chromatography (1% to 2% methanol in dichloromethane) to afford methyl 6-(6,7-dimethoxyquinolin-4-yloxy)benzofuran-3-carboxylate as a light yellow solid. MS (ESI, pos. ion) m/z: 380.1 (M+1).

Step (f) Preparation of 6-(6,7-dimethoxyquinolin-4-yloxy)benzofuran-3-carboxylic acid Methyl 6-(6,7-dimethoxyquinolin-4-yloxy)benzofuran-3-carboxylate (102 mg, 0.269 mmol) was dissolved in dioxane (1.6 mL) and water (0.5 mL), then added 2N aqueous sodium hydroxide (141 □L). The reaction mixture was stirred at room temperature overnight. The mixture was concentrated in vacuo then diluted with water. The aqueous layer was extracted with ethyl acetate. The aqueous layer was acidified with aqueous 1N hydrochloric acid (282 µL) and the precipitate was collected, washed with water and dried under high vacuum to give 6-(6,7-dimethoxyquinolin-4-yloxy)benzofuran-3-carboxylic acid as a light yellow solid (65 mg). MS (ESI, pos. ion) m/z: 366.1 (M+1).

Step (g) Preparation of N-(4-chlorophenyl)-6-(6,7-dimethoxyquinolin-4-yloxy)benzofuran-3-carboxamide 6-(6,7-Dimethoxyquinolin-4-yloxy)benzofuran-3-carboxylic acid (31 mg, 0.085 mmol) and 2-(1H-benzotriazole-1-yl)-1,1,3,3-tetramethyluronium tetrafluoroborate (41 mg, 0.127 mmol) were added to a reaction tube then dissolved in DMF (0.6 mL). 4-chloroaniline (13 mg, 0.102 mmol) was added to the reaction mixture, followed by N,N-diisopropylethylamine (22 mg, 0.17 mmol) and stirring was continued for 2 days. The mixture was concentrated in vacuo. The remaining orange oil was purified by silica gel chromatography (1% to 2% methanol in dichloromethane) to afford N-(4-chlorophenyl)-6-(6,7-dimethoxyquinolin-4-yloxy)benzofuran-3-carboxamide as a yellow solid (5 mg). MS (ESI, pos. ion) m/z: 475.1 (M+1). Mass calc'd for $C_{26}H_{19}ClN_2O_5$: 474.89.

Example 152

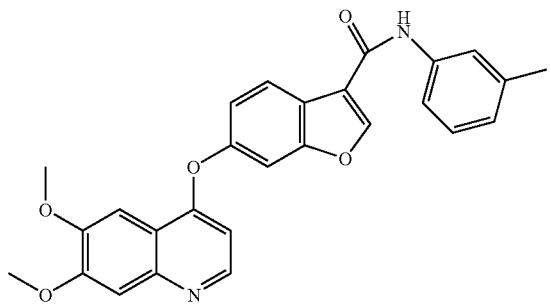

6-((6,7-bis(Methoxy)-4-quinolinyl)oxy)-N-(3-methylphenyl)-1-benzofuran-3-carboxamide Prepared as described above for example 151. MS (ESI, pos. ion) m/z: 455.1 (M+1). Mass calc'd for $C_{27}H_{22}N_2O_5$: 454.48.

TABLE 1

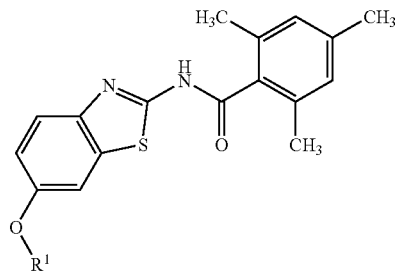

| # | $R^1$ |
|---|---|
| 153. | pyridin-4-yl |
| 154. | 4-pyrimidinyl |
| 155. | quinazolin-4-yl |
| 156. | 6,7-dimethoxyquinazolin-4-yl |

TABLE 2

[Structure: quinoline with 6,7-dimethoxy substituents, at 4-position O-A-NH-C(=O)- linked to 2,6-dimethyl-4-methylphenyl (showing CH3, CH3, CH2 labels)]

| # | A |
|---|---|
| 157. | [6-methyl-benzoxazol-2-yl] |
| 158. | [5-methyl-indol-2-yl] |
| 159. | [benzimidazol-2,6-diyl (NH)] |
| 160. | [1-methyl-benzimidazol-2,6-diyl] |

Although the pharmacological properties of the compounds of Formulas I-III vary with structural change, in general, activity possessed by compounds of Formulas I-III may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of c-Met kinase at doses less than 20 μM.

Biological Testing

The efficacy of the compounds of the invention as inhibitors of VEGF and/or GF related activity are demonstrated as follows.

c-Met Receptor Assay

Cloning, Expression and Purification of c-Met Kinase Domain

A PCR product covering residues 1058-1365 of c-Met (c-Met kinase domain) is generated from Human Liver QuickClone™ cDNA (Invitrogen) using forward primer 5'-ATTGACGGATCCATGCT AAATCCAGAGCTGGTC-CAGGCA-3' (SEQ ID NO. 1) and reverse primer 5'-ACAA-CAGAATTCAA TACGGAGCGACACATTTTACGTT-3' (SEQ ID NO. 2). The PCR product is cloned into a modified pFastBac1 expression vector (harboring the gene for *S. japonicum* glutathione S-transferase immediately upstream of the multiple cloning site) using standard molecular biological techniques. The GST-c-Met kinase domain fusion (GST-Met) gene is transposed into full-length baculovirus DNA using the BacToBac™ system (Invitrogen). High5 cells are infected with the recombinant baculovirus for 72 h at 27° C. The infected cells are harvested by centrifugation and the pellet is stored at −80° C. The pellet is resuspended in buffer A (50 mM HEPES, pH 8.0, 0.25 M NaCl, 10 mM 2-mercaptoethanol, 10% (w/v) glycerol, 0.5% (v/v) protease inhibitor cocktail (Sigma P8340), stirred at 4° C. to homogeneity, and the cells are disrupted by microfluidization (Microfluidics) at 10,000 psi. The resulting lysate is centrifuged at 50,000×g for 90 min at 4° C., and the supernatant is adsorbed onto 10 mL of glutathione Sepharose™ 4B (Amersham) by batch method. The slurry is rocked gently overnight at 4° C. The glutathione resin is harvested by centrifugation and washed three times with 40 mL buffer A by batch method. The resin is washed three times with buffer B (buffer A adjusted to 0.1 M NaCl, less protease inhibitors). The protein is eluted with buffer B containing 25 mM reduced glutathione. Eluted fractions are analyzed by SDS-PAGE and concentrated to <10 mL (~10 mg/mL total protein). The concentrated protein is separated by Superdex™ 200 (Amersham) size exclusion chromatography in buffer C (25 mM Tris, pH 7.5, 0.1 M NaCl, 10 mM 2-mercaptoethanol, 10% glycerol). The fractions are analyzed by SDS-PAGE and the appropriate fractions are pooled and concentrated to ~1 mg/mL. The protein is aliquotted and stored at −80° C.

Alternative Purification of Human GST-cMET from Baculovirus Cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche #10019600), 1 tablet per 50 mL buffer). The lysed cell suspension is centrifuged at 100,000×g (29,300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10,00 MW cutoff) to a final volume less than 2.0 mL. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

|   | Final concentration | |
|---|---|---|
| a) | 100 mM ATP (Sigma #A7699) | 25 mM |
| b) | 1.0 M MgCl$_2$(Sigma #M-0250) | 100 mM |
| c) | 200 mM Sodium Orthovanadate (Sigma #S-6508) | 15 mM |
| d) | 1.0 M Tris-HCl, pH 7.00 (in house) | 50 mM |
| e) | H$_2$0 | |
| f) | GST-cMET | 0.2-0.5 mg/mL |

After incubation, the solution is concentrated in a Vivaspin 20 mL Concentrator to a volume less than 2.00 mL. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the OD$_{280}$ is read with the column buffer used as the blank.

A Kinase reaction Buffer is prepared as follows:

|   |   |   | Per 1 L |
|---|---|---|---|
| 60 mM HEPES $_p$H 7.4 | 1 M stock | 16.7× | 60 mL |
| 50 mM NaCl | 5 M stock | 100× | 10 mL |
| 20 mM MgCl$_2$ | 1 M stock | 50× | 20 mL |
| 5 mM MnCl$_2$ | 1 M stock | 200× | 5 mL |

When the assay is carried out, freshly add:

| 2 mM DTT | 1 M stock | 500× |
|---|---|---|
| 0.05% BSA | 5% stock | 100× |
| 0.1 mM Na$_3$OV$_4$ | 0.1 M stock | 1000× |

The HTRF buffer contains:

50 mM Tris-HCl ($_p$H 7.5), 100 mM NaCl, 0.1% BSA, 0.05% Tween 20.5 mM EDTA

Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:
  0.1 nM final Eu-PT66
  11 nM final SA-APC Methods:

1. Dilute GST-cMet (P) Enzyme in Kinase Buffer as Follows:

Prepare 8 nM GST-cMet (P) working solution (7.32 µM to 8 nM, 915×, 10 µL to 9.15 mL). In a 96 well clear plate [Costar #3365] add 100 µL in eleven columns, in one column add 100 µL kinase reaction buffer alone.

2. Assay Plate Preparation:

Use Biomek FX to transfer 10 µL 8 nM GST-cMet (P) enzyme, 48.4 µL kinase reaction buffer, 1.6 µL compound (in DMSO) (Start concentration at 10 mM, 1 mM and 0.1 mM, sequential dilution 1:3 to reach 10 test points) in a 96 well costar clear plate [Costar # 3365], mix several times. Then incubate the plate at RT for 30 min.

3. Prepare Gastrin and ATP Working Solution in Kinase Reaction Buffer as Follows:

| Prepare 4 µM Gastrin and 16 µM ATP working solution | | |
|---|---|---|
|   |   | Per 10 mL |
| Gastrin 4 µM stock | (500 µM to 4 µM, 125×) | 80 µL |
| ATP 16 µM stock | (1000 µM to 16 µM, 62.5×) | 160 µL |

Use Biomek FX to add 20 µl ATP and Gastrin working solution to the assay plate to start reaction, incubate the plate at RT for 1 h.

4. Transfer 5 µL reaction product at the end of 1 h into 80 µL HTRF buffer in black plate [Costar #3356], read on Discover after 30 min incubation.

| Assay condition summary: | |
|---|---|
| K$_M$ATP* | 6 µM |
| [ATP] | 4 µM |
| K$_M$Gastrin/p(EY) | 3.8 µM |
| [gastrin] | 1 µM |
| [enzyme] | 1 nM |

K$_M$ATP, K$_M$ gastrin for various enzymes were determined by HTRF/$^{33}$P labeling and HTRF methods.

Examples 1, 2, 4-31, 90-93 and 96 exhibited activity with IC$_{50}$ values less than 0.5 µM.

c-Met Cell-Based Autophosphorylation Assay

Human PC3 and mouse CT26 cells are available obtained from ATCC. The cells were cultured in a growth medium containing RPMI 1640, penicillin/streptomycin/glutamine (1×) and 5% FBS. 2×10$^4$ cells in medium were plated per well in a 96 well plate and incubated at 37° C. overnight. The cells were serum-starved by replacing the growth media with basic medium (DMEM low glucose+0.1 BSA, 120 µL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 µL per well) were diluted with basic medium (240 µL) in a 96 well plate. The cells were washed once with basic medium (GIBCO, DMEM 11885-076) then compound solution was added (100 µL). The cells were incubated at 37° C. for 1 h. A (2 mg/mL) solution of CHO-HGF (7.5 µL) was diluted with 30 mL basic medium to provide a final concentration of 500 ng/mL. This HGF-containing media (120 µL) was transferred to a 96 well plate. Compounds (1.2 µL) was added to the HGF-containing media and mixed well. The mixture of media/HGF/compound (100 µL) was added to the cells (final HGF concentration—250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 µL, Roche Protease inhibitor (Complete, # 1-697-498) 2 tablets, Phosphatase Inhibitor II (Sigma, #P-5726) 200 µL, and a sodium vanadate solution (containing 900 µL PBS, 100 µL 300 mM NaVO$_3$, 6 µl H$_2$O$_2$ (30% stock) and stirred at RT for 15 min) (90 µL). The cells were washed once with ice cold 1×PBS (GIBCO, #14190-136), then lysis buffer (60 µL) was added and the cells were incubated on ice for 20 min.

The IGEN assay was performed as follows: Dynabeads M-280 streptavidin beads were pre-incubated with biotinylated anti-human HGFR (240 µL anti-human-HGFR (R&D system, BAF527 or BAF328) @ 100 µg/mL+360 µL Beads (IGEN #10029+5.4 µL buffer–PBS/1% BSA/0.1% Tween20) by rotating for 30 min at RT. Antibody beads (25 µL) were transferred to a 96 well plate. Cell lysate solution (25 µL) was transferred added and the plate was shaken at RT for 1 h. Anti-phosphotyrosine 4G10 (Upstate 05-321) (19.7 µL antibody+6 mL 1×PBS) (12.5 µL) was added to each well, then incubated for 1 h at RT. Anti-mouse IgG ORI-Tag (ORIGEN #110087) (24 µL Antibody+6 mL buffer) (12.5 µL) was added to each well, then incubated at RT for 30 min. 1×PBS (175 µL) was added to each well and the electrochemiluminescence was read by an IGEN M8. Raw data was analyzed using a 4-parameter fit equation in XLFit. $IC_{50}$ values are then determined using Grafit software.

Examples 46, 82, 96, 102 and 104 exhibited activity in PC3 cells with $IC_{50}$ values less than 1.0 µM. Examples 36, 46, 71, 82, 89, 96, 100-102 and 104 exhibited activity in CT26 cells with $IC_{50}$ values less than 1.0 µM.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+ antibiotics, and spun at 1000 rpm for 10 min. Prior to centrifugation of the cells, a small amount is collected for a cell count. After centrifugation, the medium is discarded, and the cells are resuspended in the appropriate volume of DMEM+ 10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+ 10% FBS+antibiotics (400× dilution). Medium containing 0.25% DMSO is also prepared for the 10 µM compound sample. At the 22 h timepoint, the medium is removed from the cells, and 100 µL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Examples 132, 134-140, 142 144 and 145 inhibited VEGF-stimulated HUVEC proliferation at a level below 500 nM.

Tumor Model

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at doses less than 100 mpk.

Formulations

Also embraced within this invention is a class of pharmaceutical compositions comprising the active compounds of Formula I-II in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferrer to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

g) substituted or unsubstituted alkenyl,
h) substituted or unsubstituted alkynyl,
i) alkylaminocarbonyl,
j) aminocarbonyl, and
k) cyano;
wherein $R^1$ is

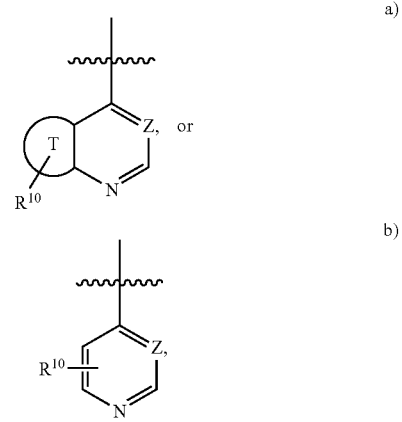

What is claimed is:
1. A compound of Formula I'

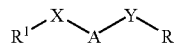

wherein R is selected from
a) substituted or unsubstituted aryl,
b) substituted or unsubstituted heterocyclyl,
c) substituted or unsubstituted cycloalkyl,
d) substituted or unsubstituted cycloalkenyl,
e) H,
f) substituted or unsubstituted alkyl, wherein ring T is selected from phenyl and 5-6-membered heteroaryl; wherein Z is selected from N or $CR^x$; wherein $R^x$ is selected from H, CN, $NH_2$, F, alkylcarbonylamino, and alkylaminocarbonyl; wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;

wherein A is selected from the following:

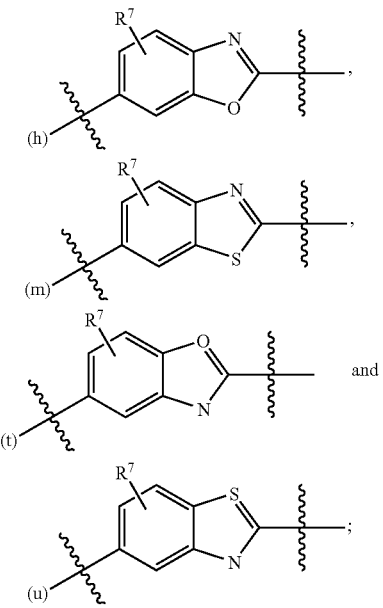

wherein X is selected from O and S;
wherein Y is selected from NR$^b$(CR$^3$R$^4$)$_p$—, —NR$^b$C(=O)(CR$^3$R$^4$)$_p$—, —NR$^b$C(=O)NR$^b$(CR$^3$R$^4$)$_p$—, —NR$^b$C(=O)NR$^b$(CR$^3$R$^4$)$_p$O—, —NR$^b$C(=O)O(CR$^3$R$^4$)$_p$—, —NR$^b$C(=S)(CR$^3$R$^4$)$_p$—, —NR$^b$C(=NR$^a$)(CR$^3$R$^4$)$_p$—, —NR$^b$SO$_2$—(CR$^3$R$^4$)$_p$—, —OC(=O)(CR$^3$R$^4$)$_p$—, —O(CR$^3$R$^4$)$_p$—, —(CR$^3$R$^4$)$_p$—S(=O)$_t$—, —(CR$^3$R$^4$)$_p$—, —S(=O)$_t$NR$^b$(CR$^3$R$^4$)$_p$—, —S(=O)$_t$(CR$^3$R$^4$)$_p$—, —C(=O)(CR$^3$R$^4$)$_p$—, —C(=NR$^a$)NH(CR$^3$R$^4$)$_p$—, C(=S)NH(CR$^3$R$^4$)$_p$— and —C(=O)NH(CR$^3$R$^4$)$_p$—; wherein Y is in either direction;
wherein R$^a$ and R$^b$ is each independently selected from H, alkyl, heterocyclyl, aryl, arylalkyl, heterocyclylalkyl, cycloalkyl, cycloalkylalkyl, alkenyl, alkynyl, R$^5$R$^5$N—(C=O)—, and R$^5$—(=O)—; wherein each of R$^a$ and R$^b$ is optionally substituted;
wherein R$^2$ is selected from H, alkyl, haloalkyl, aryl, heterocyclyl, arylalkyl, heterocyclylalkyl, cycloalkyl, cycloalkylalkyl, alkenyl, alkynyl and R$^5$-carbonyl;
wherein R$^3$ and R$^4$ is each independently selected from H, alkyl, aryl, heterocyclyl, arylalkyl, heterocyclylalkyl, haloalkyl, cycloalkyl, cycloalkylalkyl, R$^6$ and alkyl substituted with R$^6$;
wherein R$^5$ is selected from H, alkyl, haloalkyl, arylalkyl, heterocyclylalkyl, cycloalkylalkyl, aryl, heterocyclyl, alkenyl, alkynyl and cycloalkyl;
wherein R$^6$ is selected from cyano, —OR$^2$, —SR$^2$, halo, —SO$_2$R$^2$, —C(O)R$^2$, —SO$_2$NR$^2$R$^5$, —NR$^5$C(=O)OR$^2$, —NR$^5$C(=O)NR$^5$R$^2$, —NR$^5$C(=O)R$^2$, —CO$_2$R$^2$, —C(=O)NR$^2$R$^5$ and —NR$^2$R$^5$;
wherein p is 0, 1, 2, or 3; and
wherein t is 0, 1 or 2;
and pharmaceutically acceptable derivatives thereof;
provided R is not 4-chloro-3-(1-methylpyrrolidin-2-yl)phenyl when Y is NH and A is 2,5-benzoxazolyl and when R$^1$ is 6,7-dimethoxyquinolinyl; further provided R is not 4-chloro-3-(1-methylpyrrolidin-2-yl)phenyl when Y is NH and A is 2,5-benzoxazolyl and when R$^1$ is 6,7-dimethoxyquinazolinyl; further provided R is not phenyl when Y is CH$_2$ and A is 2,5-benzimidazolyl and when R$^1$ is 6,7-dimethoxyquinolinyl; further provided Y is not —NH— or —NMe— when X is O, S, CH$_2$ or NH, and A is benzimidazolyl, benzoxazolyl or benzothiazolyl; and further provided R is not methyl when Y is —(CR$^3$R$^4$)$_p$—, when p is 0, and A is 2,5-indolyl.

2. Compound of claim 1 wherein R is optionally substituted phenyl or optionally substituted naphthyl.

3. Compound of claim 1 wherein R is a substituted or unsubstituted heterocyclyl ring selected from pyrrolidinyl, pyrrolyl, imidazolyl, pyrazolyl, pyrazinyl, pyrimidinyl, pyridyl, quinolinyl, isoquinolinyl, tetrahydrofuryl, 2,3-dihydrothiazolyl, 2,3-dihydrobenzofuryl, 2,3-dihydro-1,4-benzodioxinyl, 1,3-benzodioxolyl, benzisoxazolyl, benzthiazolyl, benzimidazolyl, benzothiadiazolyl, indolinyl, imidazo[1,2-a]pyridyl, isoxazolyl, isothiazolyl, oxazolyl, thiazolyl, thiadiazolyl, furanyl, and thienyl.

4. Compound of claim 1 wherein R is an unsubstituted or substituted ring selected from 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isoxazolyl, 3-isothiazolyl, 5-oxazolyl, 4-thiazolyl, 5-thiazolyl, 2-furanyl, 3-furanyl, 3-thienyl and 2-thienyl.

5. Compound of claim 1 wherein A is selected from

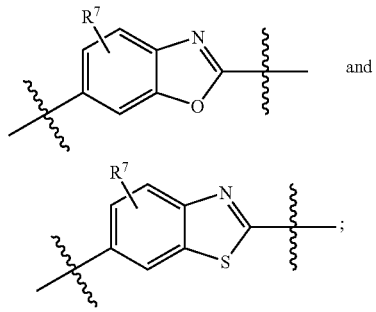

wherein R$^7$ selected from H, halo and methyl;
and pharmaceutically acceptable derivatives thereof.

6. Compound of claim 1 wherein A is

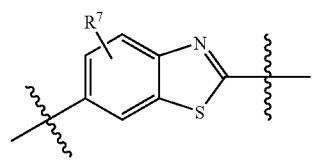

7. Compound of claim 1 wherein

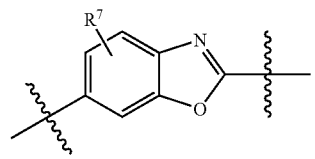

8. Compound of claim 1 wherein $R^1$ is

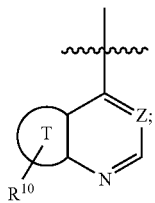

wherein ring T is selected from phenyl and 5-6-membered heteroaryl; wherein Z is selected from N or CH; wherein $R^{10}$ is one or more substituents selected from $R^8O$—; and wherein $R^8$ is selected from $C_{1-6}$-alkyl, $C_{1-6}$-haloalkyl, $C_{1-6}$-alkylamino-$C_{1-6}$-alkyl, aryl-$C_{1-6}$-alkyl, heterocyclyl-$C_{1-6}$-alkyl, cycloalkyl-$C_{1-6}$-alkyl, heterocyclyl-$C_{1-6}$-(hydroxyalkyl), cycloalkyl-$C_{1-6}$-(hydroxyalkyl), aryl-$C_{1-6}$-(hydroxyalkyl), $C_{1-6}$-alkoxyalkyl, aryloxy-$C_{1-6}$-alkyl, heterocyclyloxy-$C_{1-6}$-alkyl, cycloalkyloxy-$C_{1-6}$-alkyl, aryl, heterocyclyl, and cycloalkyl.

9. Compound of claim 1 wherein $R^1$ is selected from

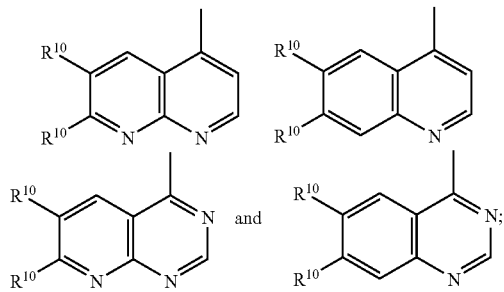

and wherein $R^{10}$ is selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkoxy-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), phenyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy.

10. Compound of claim 1 wherein $R^1$ is selected from 6,7-dimethoxy-4-quinolinyl, 6-methoxy-7-(dimethylaminopropoxy)-4-quinolinyl, 6-methoxy-7-(4-morpholinylpropoxy)-4-quinolinyl, 6,7-dimethoxy-4-quinazolinyl, and 6-methoxy-7-(dimethylaminopropoxy)-4-quinazolinyl.

11. Compound of claim 1 wherein Y is selected from —NH$(CH_2)_p$—, —NHC(=O)$(CH_2)_p$—, —NHC(=O)$(CH_2)_p$O—, —NHC(=O)O$(CH_2)_p$—, —$(CH_2)_p$—NHC(=O)—, —NHC(=O)NH—, —C(=O)O—, —NHSO$_2$—, and C(=O)NH$(CH_2)_p$—; and wherein p is 0, 1, or 2.

12. Compound of claim 1 wherein Y is selected from —NH—, —NHCH$_2$—, —NH$(CH_2)_2$—, —NH$(CH_2)_3$—, —NHC(=O)CH$_2$—, —NHC(=O)$(CH_2)_2$—, —NHC(=O)—, —NHC(=O)CH$_2$O—, —NHC(=O)OCH$_2$—, —NHC(=O)NH—, —$(CH_2)$NHC(=O)—, —C(=O)O—, —NHSO$_2$—, and —C(=O)NHCH$_2$—.

13. Compound of claim 1 wherein R is selected from cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH$_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ymethyl)phenyl, 2-(4-methylpiperazin-1-ymethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl; and pharmaceutically acceptable derivatives thereof.

14. Compound of claim 1 wherein X is O.

15. Compound of claim 1 and pharmaceutically acceptable salts thereof selected from:

N-[6-(6,7-Dimethoxy-quinolin-4-yloxy)-benzothiazol-2-yl]-3-methyl-benzamide;

Thiophene-3-carboxylic acid [6-(6,7-dimethoxy-quinolin-4-yloxy)-benzothiazol-2-yl]-amide;

2-Phenyl-N-[6-(7-trifluoromethyl-quinolin-4-yloxy)-benzothiazol-2-yl]-acetamide;

N-[6-(2-Methyl-pyridin-4-yloxy)-benzothiazol-2-yl]-2-phenyl-acetamide;

4-Chloro-N-[6-(6,7-dimethoxy-quinolin-4-yloxy)-benzothiazol-2-yl]-benzamide;

5-((6,7-bis(methoxy)-4-quinolinyl)oxy)-N-(4-chlorophenyl)-1,3-benzoxazol-2-amine;

N-(6-((7-((2-(dimethylamino)ethyl)oxy)-6-(methoxy)-4-quinolinyl)oxy)-1,3-benzothiazol-2-yl)-2-thiophenecarboxamide;

N-(6-((7-((2-(dimethylamino)ethyl)oxy)-6-(methoxy)-4-quinolinyl)oxy)-1,3-benzothiazol-2-yl)-3-thiophenecarboxamide;

N-(6-((7-((3-(dimethylamino)propyl)oxy)-6-(methoxy)-4-quinolinyl)oxy)-1,3-benzothiazol-2-yl)benzamide; and N-(6-((6-(methoxy)-7-((3-(4-morpholinyl)propyl)oxy)-4-quinolinyl)oxy)-1,3-benzothiazol-2-yl)-3-thiophenecarboxamide.

16. A compound of claim 1 having the following formula II'

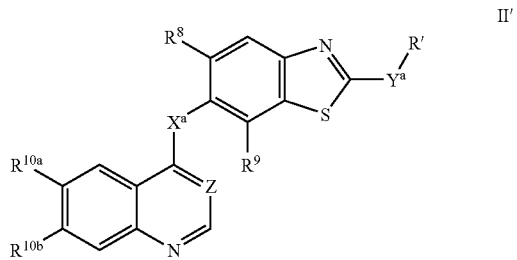

wherein $X^a$ is O;

wherein $Y^a$ is selected from —NH(CH$_2$)$_{1-3}$—, —NHC(=O)(CH$_2$)$_p$—, —NHC(=O)(CH$_2$)$_p$O—, —(CH$_2$)$_p$—NHC(=O)—, —NHC(=O)NH—, —NHC(=O)O(CH$_2$)$_p$—, and —C(=O)O—;

wherein Z is CH or N;

wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkyl-aminocarbonyl-$C_{1-5}$-alkyl, amino-$C_{1-5}$-alkyl, $C_{1-5}$-alkyl-amino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, 2,3-dihydro-1,4-benzodioxinyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, piperidinyl, 1-methyloxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^8$ is selected from H, fluoro, chloro and methyl;

wherein $R^9$ is selected from H, methyl and fluoro;

wherein $R^{10a}$ is H or methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

17. Compound of claim 16 wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH(CH$_3$)—, phenyl-CH(CH$_3$)—, 5-methylisoxazol-3-ylmethyl, pyrrolidin-1-ylethyl, tetrahydrofur-2-ylmethyl, 4-methyl-2-oxo-oxazolidin- 5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, $(CH_3)_3CCH_2$—, pentafluoroethyl, $CF_3CH_2CH_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N (CH$_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ymethyl)phenyl, 2-(4-methylpiperazin-1-ymethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methyl-isothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl; and pharmaceutically acceptable derivatives thereof.

18. Compound of claim 16 wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy; and pharmaceutically acceptable derivatives thereof.

19. Compound of claim 16 wherein $R^8$ is H; and wherein $R^9$ is H, methyl or fluoro; and pharmaceutically acceptable derivatives thereof.

20. Compound of claim 16 wherein $Y^a$ is selected from $NHC(=O)(CH_2)_p$—, —$NHC(=O)(CH_2)_pO$—, —$(CH_2)_p$ —NHC(=O)—, —NHC(=O)NH—, —NHC(=O)O(CH$_2$)$_p$—, —NHSO$_2$—, and —C(=O)NH(CH$_2$)$_p$—; wherein p is 0, 1, 2, or 3; and pharmaceutically acceptable derivatives thereof.

21. Compound of claim 16 wherein Y$^a$ is selected from NHC(=O)—, —NHC(=O)(CH$_2$)—, —NHC(=O)(CH$_2$)$_2$—, —(CH$_2$)$_p$—NHC(=O)—, —NHC(=O)NH— and —NHSO$_2$—; and pharmaceutically acceptable derivatives thereof.

22. Compound of claim 16 wherein Y$^a$ is —NHC(=O)— and —NHC(=O)CH$_2$—; and pharmaceutically acceptable derivatives thereof.

23. Compound of claim 16 wherein X is O; and pharmaceutically acceptable derivatives thereof.

24. Compound of claim 16 wherein R' is selected from cyclopropyl, cyclobutyl, cyclopentyl, cyclohexyl, phenyl, 4-methylphenyl, 3-methylphenyl, 2-methylphenyl, 2-ethylphenyl, 3-isopropylphenyl, 4-tert-butyl-phenyl, 2,3-dimethylphenyl, 4-isopropyl-3-methylphenyl, 3-chloro-4-methylphenyl, 4-fluorophenyl, 3-fluorophenyl, 2-fluorophenyl, 2,4-difluorophenyl, 3,4-difluorophenyl, 4-bromophenyl, 4-chlorophenyl, 3-chlorophenyl, 2-chlorophenyl, 2,4-dichlorophenyl, 3,4-dichlorophenyl, 3-chloro-4-fluorophenyl, 2-methoxyphenyl, 3-methoxyphenyl, 4-methoxyphenyl, 4-methylthiophenyl, 3-methylsulfonylphenyl, 2-methylsulfonylphenyl, 4-trifluoromethoxyphenyl, 3-trifluoromethoxyphenyl, 4-trifluoromethylphenyl, 3-trifluoromethylphenyl, 2-trifluoromethylphenyl, 4-chloro-3-trifluoromethylphenyl, 2-chloro-4-trifluoromethylphenyl, 3,5-di(trifluoromethyl)phenyl, 4-dimethylaminophenyl, 3-(4-methylpiperazin-1-ymethyl)phenyl, 2-(4-methylpiperazin-1-ymethyl)phenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 2-[methyl-(1-methylpyrrolidin-3-yl)amino]-5-trifluoromethylphenyl, biphenyl, 2-pyrrolidinyl, 1-methyl-2-pyrrolidinyl, 4-piperazinyl, 2-pyrrolyl, 1-methyl-2-pyrrolyl, 5-imidazolyl, 3-pyrazolyl, 2-pyrazinyl, 5-methyl-2-pyrazinyl, 4-pyrimidinyl, 2,6-dimethoxy-4-pyrimidinyl, 2-pyridyl, 3-pyridyl, 2-chloro-3-pyridyl, 2-chloro-5-pyridyl, 4-chloro-2-pyridyl, 4-trifluoromethyl-2-pyridyl, 4-methoxy-5-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 4,5-dichloro-3-isothiazolyl, 5-oxazolyl, 4-thiazolyl, 2-methyl-4-thiazolyl, 2,5-dimethyl-4-thiazolyl, 2-thiazolyl, 2-furanyl, 4,5-dimethyl-2-furyl, 5-methyl-2-trifluoromethyl-3-furyl, 3-furanyl, 3-thienyl, 4-methoxy-5-chloro-3-thienyl, 2-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 5-tert-butyl-isoxazol-3-yl, 5-methyl-isoxazol-3-yl, 3,5-dimethyl-isoxazol-4-yl, 5-tert-butyl-pyrazol-3-yl, and 2-methylbenzothiazol-5-yl.

25. A pharmaceutical composition comprising a pharmaceutically-acceptable carrier and a compound of claim 1.

* * * * *

SEQUENCE LISTING

<160> NUMBER OF SEQ ID NOS: 2

<210> SEQ ID NO 1
<211> LENGTH: 39
<212> TYPE: DNA
<213> ORGANISM: Homo sapiens

<400> SEQUENCE: 1
attgacggat ccatgctaaa tccagagctg gtccaggca                    39

<210> SEQ ID NO 2
<211> LENGTH: 37
<212> TYPE: DNA
<213> ORGANISM: Homo sapiens

<400> SEQUENCE: 2
acaacagaat tcaatacgga gcgacacatt ttacgtt                      37